(12) United States Patent
Braddock et al.

(10) Patent No.: US 10,064,917 B2
(45) Date of Patent: *Sep. 4, 2018

(54) COMPOSITIONS FOR TREATING PATHOLOGICAL CALCIFICATION CONDITIONS, AND METHODS USING SAME

(71) Applicant: YALE UNIVERSITY, New Haven, CT (US)

(72) Inventors: Demetrios Braddock, Guilford, CT (US); Ronald Albright, Hamden, CT (US)

(73) Assignee: Yale Unviersity, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/672,791

(22) Filed: Aug. 9, 2017

(65) Prior Publication Data

US 2017/0340713 A1 Nov. 30, 2017

Related U.S. Application Data

(63) Continuation of application No. PCT/US2016/033236, filed on May 19, 2016.

(60) Provisional application No. 62/163,500, filed on May 19, 2015.

(51) Int. Cl.

| | |
|---|---|
| *A61K 38/46* | (2006.01) |
| *A61K 38/17* | (2006.01) |
| *A01K 67/027* | (2006.01) |
| *C07K 14/745* | (2006.01) |
| *A61K 38/04* | (2006.01) |
| *A61K 48/00* | (2006.01) |
| *C07K 7/06* | (2006.01) |
| *C12N 9/96* | (2006.01) |
| *C12N 15/52* | (2006.01) |
| *C12N 15/62* | (2006.01) |
| *C12N 15/85* | (2006.01) |
| *C12Q 1/6883* | (2018.01) |
| *A61K 38/02* | (2006.01) |

(52) U.S. Cl.
CPC ...... *A61K 38/1741* (2013.01); *A01K 67/0271* (2013.01); *A61K 38/02* (2013.01); *A61K 38/04* (2013.01); *A61K 38/46* (2013.01); *A61K 38/465* (2013.01); *A61K 48/0058* (2013.01); *C07K 7/06* (2013.01); *C07K 14/745* (2013.01); *C12N 9/96* (2013.01); *C12N 15/52* (2013.01); *C12N 15/625* (2013.01); *C12N 15/85* (2013.01); *C12Q 1/6883* (2013.01); *C12Y 301/04001* (2013.01); *C12Y 306/01009* (2013.01); *A01K 2207/15* (2013.01); *A01K 2207/20* (2013.01); *A01K 2227/105* (2013.01); *A01K 2267/0387* (2013.01); *C07K 2319/01* (2013.01); *C07K 2319/30* (2013.01); *C07K 2319/31* (2013.01); *C07K 2319/33* (2013.01); *C07K 2319/70* (2013.01); *C12N 2840/007* (2013.01); *H05K 999/99* (2013.01)

(58) Field of Classification Search
None
See application file for complete search history.

(56) References Cited

U.S. PATENT DOCUMENTS

| | | | |
|---|---|---|---|
| 7,323,542 B2 | 1/2008 | Balian et al. | |
| 7,888,372 B2 | 2/2011 | Millan et al. | |
| 8,846,603 B2 | 9/2014 | Quinn et al. | |
| 9,744,219 B2 | 8/2017 | Braddock et al. | |
| 2007/0015145 A1 | 1/2007 | Woolf et al. | |
| 2014/0154774 A1 | 6/2014 | Quinn et al. | |
| 2014/0377859 A1 | 12/2014 | Quinn et al. | |
| 2015/0024460 A1 | 1/2015 | Quinn et al. | |

FOREIGN PATENT DOCUMENTS

| | | |
|---|---|---|
| WO | 02092020 A2 | 11/2002 |
| WO | 2011113027 A2 | 9/2011 |
| WO | 2012125182 A1 | 9/2012 |
| WO | 2016100803 A2 | 6/2016 |

OTHER PUBLICATIONS

PCT International Search Report and Written Opinion for PCT International Application No. PCT/US2016/033236 dated Oct. 27, 2016.
Jansen, et al., "Structure of NPP1, an ectonucleotide pyrophosphatase/phosphodiesterase involved in tissue calcification", Structure. 20(11), 2012, 1948-1959.
Shankar, et al., "Progeria—A Brief Review", International Journal of Pharma and Bio Sciences 2, 2010, 1-14.
Albright, et al., "Molecular basis of purinergic signal metabolism by ectonucleotide pyrophosphatase/phosphodiesterases 4 and 1 and implications in stroke", J Biol Chem. 289(6), 2014, 3294-3306.
Albright, et al., "NPP4 is a procoagulant enzyme on the surface of vascular endothelium", Blood. 120(22), 2012, 4432-4440.
Cimpean, et al., "Substrate-specifying determinants of the nucleotide pyrophosphatases/phosphodiesterases NPP1 and NPP2", Biochem J. 381(Pt 1), 2004, 71-77.

(Continued)

*Primary Examiner* — Kagnew H Gebreyesus
(74) *Attorney, Agent, or Firm* — Saul Ewing Arnstein & Lehr LLP; Kathryn Doyle; Domingos J. Silva

(57) ABSTRACT

The present invention includes compositions and methods for treating diseases or disorders associated with pathological calcification or pathological ossification. In certain embodiments, the diseases or disorders are selected from the group consisting of Generalized Arterial Calcification of Infancy (GACI), Idiopathic Infantile Arterial Calcification (IIAC), Ossification of the Posterior Longitudinal Ligament (OPLL), hypophosphatemic rickets, osteoarthritis, calcification of atherosclerotic plaques, PXE, hereditary and non-hereditary forms of osteoarthritis, ankylosing spondylitis, hardening of the arteries occurring with aging, calciphylaxis resulting from end stage renal disease and progeria.

22 Claims, 23 Drawing Sheets

Specification includes a Sequence Listing.

(56) References Cited

OTHER PUBLICATIONS

Gijsbers, et al., "Functional characterization of the non-catalytic ectodomains of the nucleotide pyrophosphatase/phosphodiesterase NPP1", Biochem J. 371(Pt 2), Apr. 15, 2003, 321-330.

Goding, et al., "Physiological and pathophysiological functions of the ecto-nucleotide pyrophosphatase/phosphodiesterase family", Biochim Biophys Acta. 1638(1), 2003, 1-19.

Jansen, et al., "Proteolytic maturation and activation of autotaxin (NPP2), a secreted metastasis-enhancing lysophospholipase D", J Cell Sci. 118(Pt 14), 2005, 3081-3089.

Johnson, et al., "Linked deficiencies in extracellular PP(i) and osteopontin mediate pathologic calcification associated with defective PC-1 and ANK expression", J Bone Miner Res. 18(6), 2003, 994-1004.

Schetter, et al., "Nucleoporins NPP-1, NPP-3, NPP-4, NPP-11 and NPP-13 are required for proper spindle orientation in C. elegans", Dev Biol. 289(2), Jan. 15, 2006, 360-371.

Stefan, et al., "NPP-type ectophosphodiesterases: unity in diversity.", Trends Biochem Sci. 30(10), Oct. 2005, 542-550.

Terkeltaub, "Physiologic and pathologic functions of the NPP nucleotide pyrophosphatase/phosphodiesterase family focusing on NPP1 in calcification.", Purinergic Signal. 2(2), Jun. 2, 2006, 371-377.

Zhang, et al., "The interaction of cationic polymers and their bisphosphonate derivatives with hydroxyapatite", Macromol Biosci 7(5), May 10, 2007, 656-670 (Abstract Only).

Johnson, et al., Differential mechanisms of inorganic pyrophosphate production by plasma cell membrane glycoprotein-1 and B10 in chondrocytes, Arthritis Rheum. 42(9), 1999, 1986-1997.

Lee, et al., Cloning, chromosomal localization, and tissue expression of autotaxin from human teratocarcinoma cells, Biochem Biophys Res Commun. 218(3, 1996, 714-719.

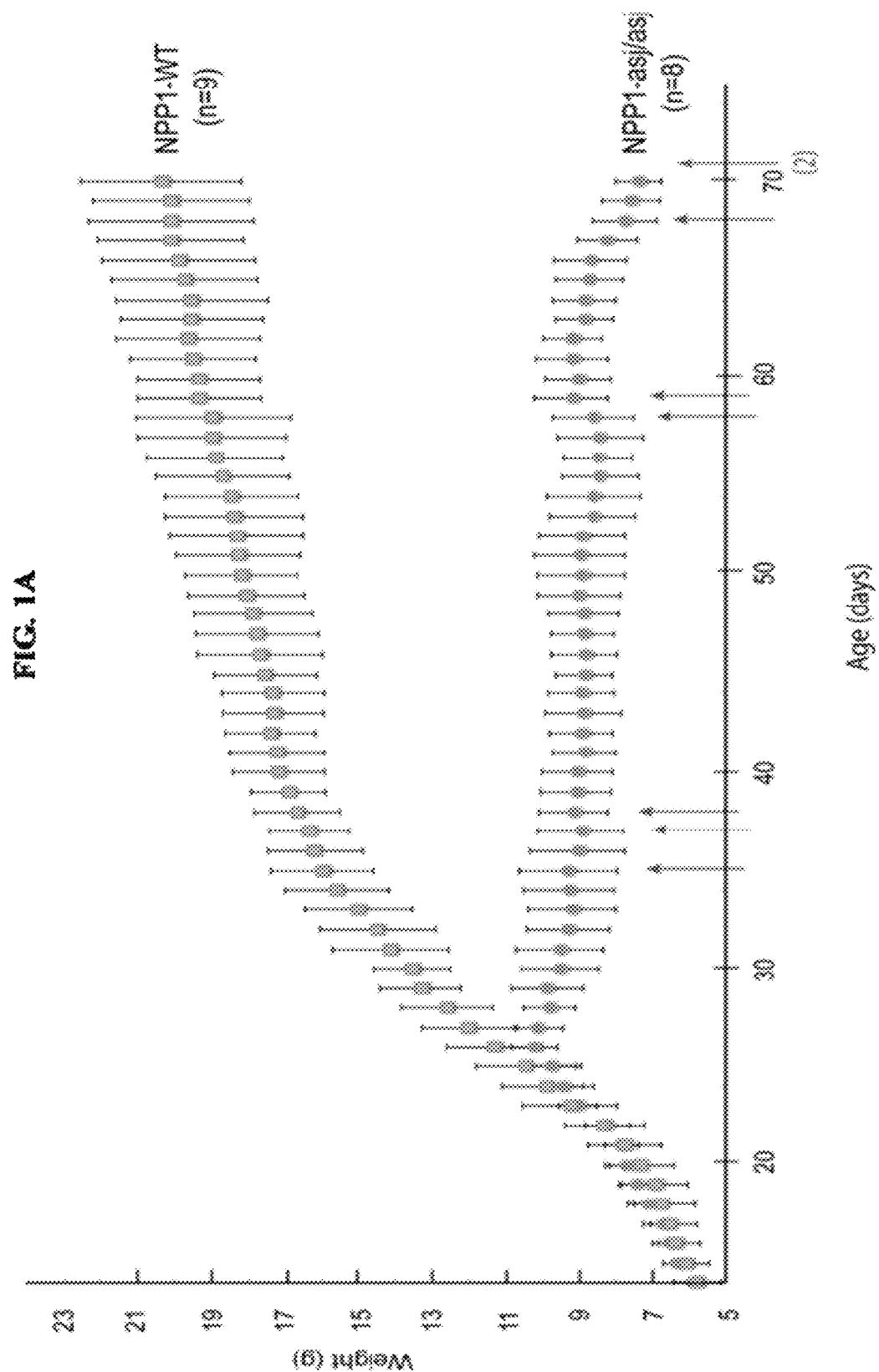

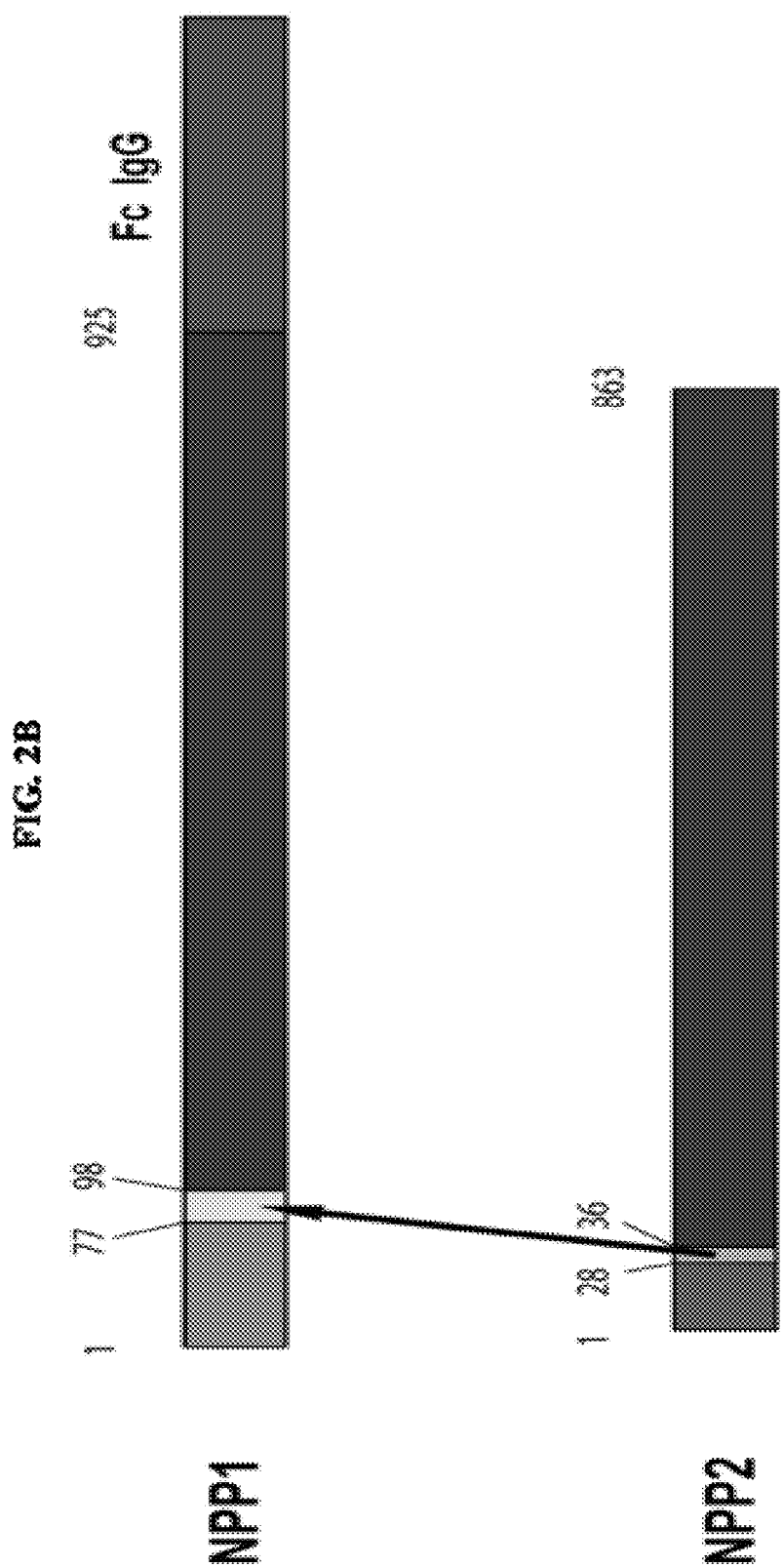

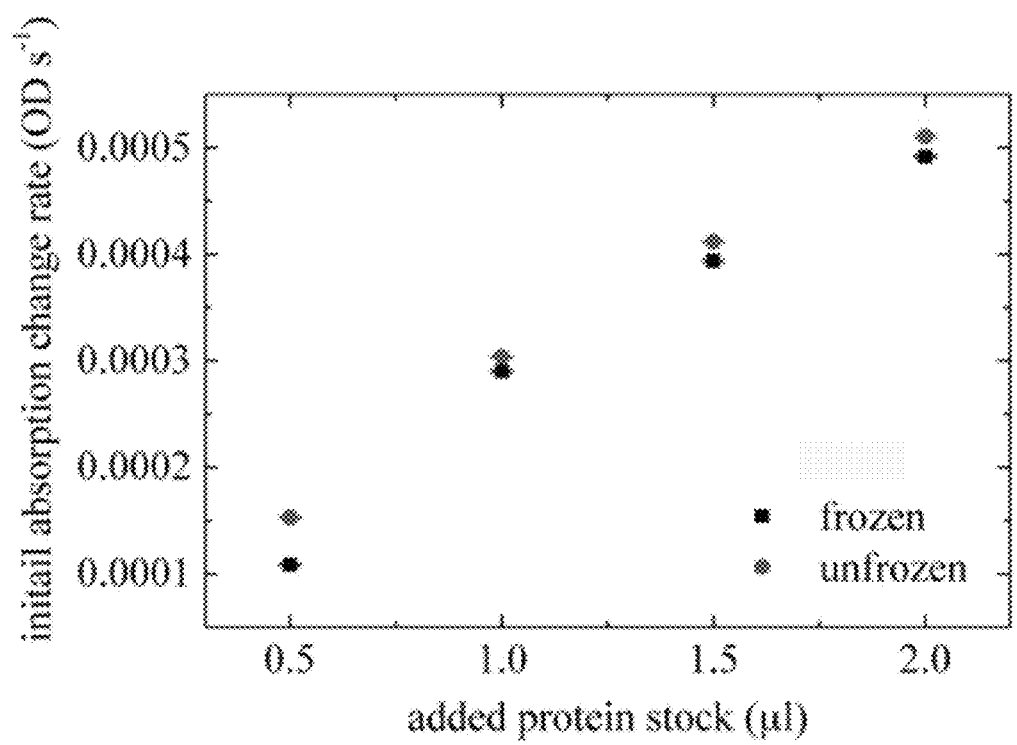

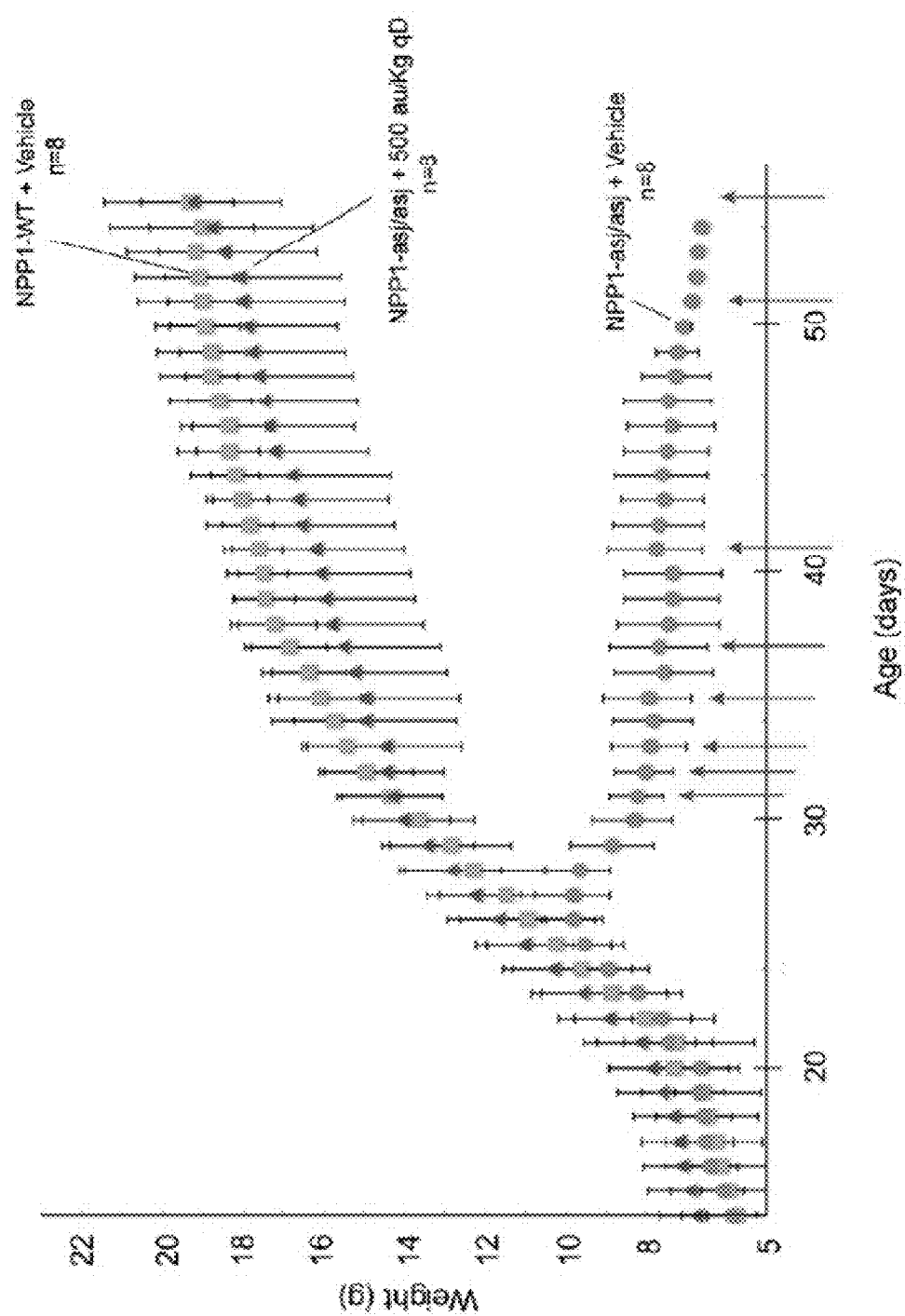

FIG. 4A
FIG. 4B
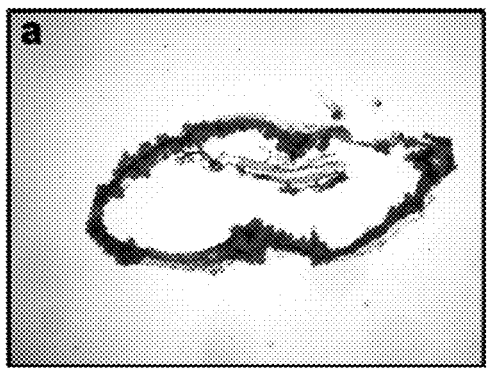
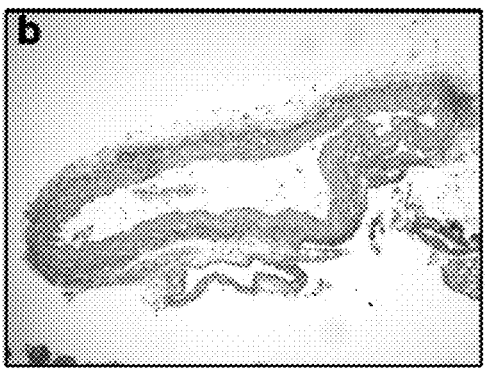
FIG. 4C
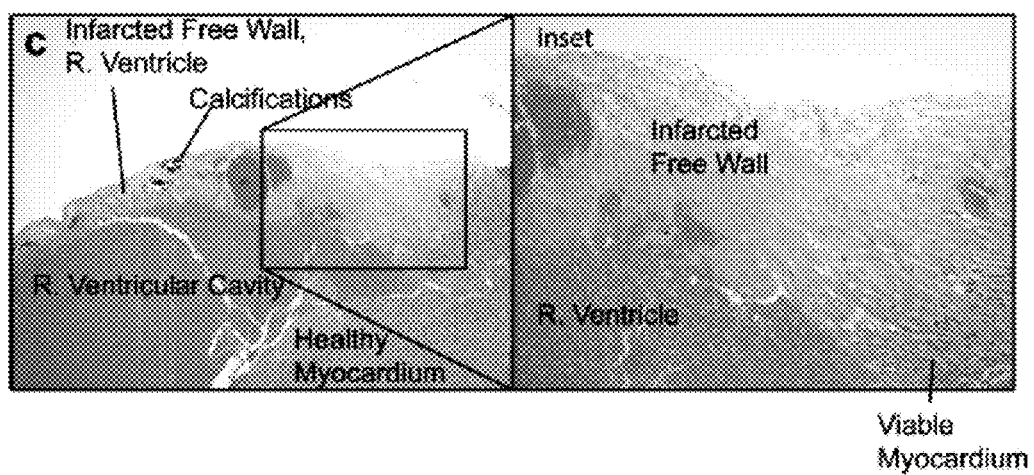

Intracardiac Calcations
Healthy Myocardium
Scar Tissue

NPP1-asj/asj untreated
NPP1-asj/asj treated

SEQUENCE LISTING

```
<160> NUMBER OF SEQ ID NOS: 30

<210> SEQ ID NO 1
<211> LENGTH: 925
<212> TYPE: PRT
<213> ORGANISM: Homo sapiens

<400> SEQUENCE: 1

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Val Leu Ser Leu
65                  70                  75                  80
```

-continued

```
Val Leu Ser Val Cys Val Leu Thr Thr Ile Leu Gly Cys Ile Phe Gly
                85                  90                  95
Leu Lys Pro Ser Cys Ala Lys Glu Val Lys Ser Cys Lys Gly Arg Cys
            100                 105                 110
Phe Glu Arg Thr Phe Gly Asn Cys Arg Cys Asp Ala Ala Cys Val Glu
        115                 120                 125
Leu Gly Asn Cys Cys Leu Asp Tyr Gln Glu Thr Cys Ile Glu Pro Glu
130                 135                 140
His Ile Trp Thr Cys Asn Lys Phe Arg Cys Gly Glu Lys Arg Leu Thr
145                 150                 155                 160
Arg Ser Leu Cys Ala Cys Ser Asp Asp Cys Lys Asp Lys Gly Asp Cys
                165                 170                 175
Cys Ile Asn Tyr Ser Ser Val Cys Gln Gly Glu Lys Ser Trp Val Glu
            180                 185                 190
Glu Pro Cys Glu Ser Ile Asn Glu Pro Gln Cys Pro Ala Gly Phe Glu
        195                 200                 205
Thr Pro Pro Thr Leu Leu Phe Ser Leu Asp Gly Phe Arg Ala Glu Tyr
210                 215                 220
Leu His Thr Trp Gly Gly Leu Leu Pro Val Ile Ser Lys Leu Lys Lys
225                 230                 235                 240
Cys Gly Thr Tyr Thr Lys Asn Met Arg Pro Val Tyr Pro Thr Lys Thr
                245                 250                 255
Phe Pro Asn His Tyr Ser Ile Val Thr Gly Leu Tyr Pro Glu Ser His
            260                 265                 270
Gly Ile Ile Asp Asn Lys Met Tyr Asp Pro Lys Met Asn Ala Ser Phe
        275                 280                 285
Ser Leu Lys Ser Lys Glu Lys Phe Asn Pro Glu Trp Tyr Lys Gly Glu
290                 295                 300
Pro Ile Trp Val Thr Ala Lys Tyr Gln Gly Leu Lys Ser Gly Thr Phe
305                 310                 315                 320
Phe Trp Pro Gly Ser Asp Val Glu Ile Asn Gly Ile Phe Pro Asp Ile
                325                 330                 335
Tyr Lys Met Tyr Asn Gly Ser Val Pro Phe Glu Glu Arg Ile Leu Ala
            340                 345                 350
Val Leu Gln Trp Leu Gln Leu Pro Lys Asp Glu Arg Pro His Phe Tyr
        355                 360                 365
Thr Leu Tyr Leu Glu Glu Pro Asp Ser Ser Gly His Ser Tyr Gly Pro
370                 375                 380
Val Ser Ser Glu Val Ile Lys Ala Leu Gln Arg Val Asp Gly Met Val
385                 390                 395                 400
Gly Met Leu Met Asp Gly Leu Lys Glu Leu Asn Leu His Arg Cys Leu
                405                 410                 415
Asn Leu Ile Leu Ile Ser Asp His Gly Met Glu Gln Gly Ser Cys Lys
            420                 425                 430
Lys Tyr Ile Tyr Leu Asn Lys Tyr Leu Gly Asp Val Lys Asn Ile Lys
        435                 440                 445
Val Ile Tyr Gly Pro Ala Ala Arg Leu Arg Pro Ser Asp Val Pro Asp
450                 455                 460
Lys Tyr Tyr Ser Phe Asn Tyr Glu Gly Ile Ala Arg Asn Leu Ser Cys
465                 470                 475                 480
Arg Glu Pro Asn Gln His Phe Lys Pro Tyr Leu Lys His Phe Leu Pro
                485                 490                 495
```

```
Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
            515                 520                 525

Tyr Cys Gly Ser Gly Phe His Gly Ser Asp Asn Val Phe Ser Asn Met
            530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
            595                 600                 605

His Pro Leu Val Gln Cys Pro Phe Thr Arg Asn Pro Arg Asp Asn Leu
            610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
            675                 680                 685

Met Pro Leu Trp Thr Ser Tyr Thr Val Asp Arg Asn Asp Ser Phe Ser
690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
            755                 760                 765

Phe Gln Val Ile Trp Arg Tyr Phe His Asp Thr Leu Leu Arg Lys Tyr
770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
            835                 840                 845

Glu Asn Leu Asp Thr Leu Ala Phe Ile Leu Pro His Arg Thr Asp Asn
            850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
```

-continued

```
                915                 920                 925
```

<210> SEQ ID NO 2
<211> LENGTH: 888
<212> TYPE: PRT
<213> ORGANISM: Homo sapiens

<400> SEQUENCE: 2

```
Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Gly Pro Pro Thr Val Leu Ser
        35                  40                  45

Asp Ser Pro Trp Thr Asn Ile Ser Gly Ser Cys Lys Gly Arg Cys Phe
50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Gly Val Lys Ala Gly
            260                 265                 270

Thr Phe Phe Trp Ser Val Val Ile Pro His Glu Arg Arg Ile Leu Thr
        275                 280                 285

Ile Leu Gln Trp Leu Thr Leu Pro Asp His Glu Arg Pro Ser Val Tyr
290                 295                 300

Ala Phe Tyr Ser Glu Gln Pro Asp Phe Ser Gly His Lys Tyr Gly Pro
305                 310                 315                 320

Phe Gly Pro Glu Met Thr Asn Pro Leu Arg Glu Ile Asp Lys Ile Val
                325                 330                 335

Gly Gln Leu Met Asp Gly Leu Lys Gln Leu Lys Leu His Arg Cys Val
            340                 345                 350

Asn Val Ile Phe Val Gly Asp His Gly Met Glu Asp Val Thr Cys Asp
        355                 360                 365
```

```
Arg Thr Glu Phe Leu Ser Asn Tyr Leu Thr Asn Val Asp Asp Ile Thr
    370                 375                 380

Leu Val Pro Gly Thr Leu Gly Arg Ile Arg Ser Lys Phe Ser Asn Asn
385                 390                 395                 400

Ala Lys Tyr Asp Pro Lys Ala Ile Ile Ala Asn Leu Thr Cys Lys Lys
                405                 410                 415

Pro Asp Gln His Phe Lys Pro Tyr Leu Lys Gln His Leu Pro Lys Arg
            420                 425                 430

Leu His Tyr Ala Asn Asn Arg Arg Ile Glu Asp Ile His Leu Leu Val
        435                 440                 445

Glu Arg Arg Trp His Val Ala Arg Lys Pro Leu Asp Val Tyr Lys Lys
    450                 455                 460

Pro Ser Gly Lys Cys Phe Phe Gln Gly Asp His Gly Phe Asp Asn Lys
465                 470                 475                 480

Val Asn Ser Met Gln Thr Val Phe Val Gly Tyr Gly Ser Thr Phe Lys
                485                 490                 495

Tyr Lys Thr Lys Val Pro Pro Phe Glu Asn Ile Glu Leu Tyr Asn Val
            500                 505                 510

Met Cys Asp Leu Leu Gly Leu Lys Pro Ala Pro Asn Asn Gly Thr His
        515                 520                 525

Gly Ser Leu Asn His Leu Leu Arg Thr Asn Thr Phe Arg Pro Thr Met
    530                 535                 540

Pro Glu Glu Val Thr Arg Pro Asn Tyr Pro Gly Ile Met Tyr Leu Gln
545                 550                 555                 560

Ser Asp Phe Asp Leu Gly Cys Thr Cys Asp Asp Lys Val Glu Pro Lys
                565                 570                 575

Asn Lys Leu Asp Glu Leu Asn Lys Arg Leu His Thr Lys Gly Ser Thr
            580                 585                 590

Glu Ala Glu Thr Arg Lys Phe Arg Gly Ser Arg Asn Glu Asn Lys Glu
        595                 600                 605

Asn Ile Asn Gly Asn Phe Glu Pro Arg Lys Glu Arg His Leu Leu Tyr
    610                 615                 620

Gly Arg Pro Ala Val Leu Tyr Arg Thr Arg Tyr Asp Ile Leu Tyr His
625                 630                 635                 640

Thr Asp Phe Glu Ser Gly Tyr Ser Glu Ile Phe Leu Met Pro Leu Trp
                645                 650                 655

Thr Ser Tyr Thr Val Ser Lys Gln Ala Glu Val Ser Ser Val Pro Asp
            660                 665                 670

His Leu Thr Ser Cys Val Arg Pro Asp Val Arg Val Ser Pro Ser Phe
        675                 680                 685

Ser Gln Asn Cys Leu Ala Tyr Lys Asn Asp Lys Gln Met Ser Tyr Gly
    690                 695                 700

Phe Leu Phe Pro Pro Tyr Leu Ser Ser Pro Glu Ala Lys Tyr Asp
705                 710                 715                 720

Ala Phe Leu Val Thr Asn Met Val Pro Met Tyr Pro Ala Phe Lys Arg
                725                 730                 735

Val Trp Asn Tyr Phe Gln Arg Val Leu Val Lys Lys Tyr Ala Ser Glu
            740                 745                 750

Arg Asn Gly Val Asn Val Ile Ser Gly Pro Ile Phe Asp Tyr Asp Tyr
        755                 760                 765

Asp Gly Leu His Asp Thr Glu Asp Lys Ile Lys Gln Tyr Val Glu Gly
    770                 775                 780

Ser Ser Ile Pro Val Pro Thr His Tyr Tyr Ser Ile Ile Thr Ser Cys
```

```
                785                 790                 795                 800
Leu Asp Phe Thr Gln Pro Ala Asp Lys Cys Asp Gly Pro Leu Ser Val
                        805                 810                 815

Ser Ser Phe Ile Leu Pro His Arg Pro Asp Asn Glu Glu Ser Cys Asn
                820                 825                 830

Ser Ser Glu Asp Glu Ser Lys Trp Val Glu Glu Leu Met Lys Met His
            835                 840                 845

Thr Ala Arg Val Arg Asp Ile Glu His Leu Thr Ser Leu Asp Phe Phe
850                 855                 860

Arg Lys Thr Ser Arg Ser Tyr Pro Glu Ile Leu Thr Leu Lys Thr Tyr
865                 870                 875                 880

Leu His Thr Tyr Glu Ser Glu Ile
                885

<210> SEQ ID NO 3
<211> LENGTH: 453
<212> TYPE: PRT
<213> ORGANISM: Homo sapiens

<400> SEQUENCE: 3

Met Lys Leu Leu Val Ile Leu Leu Phe Ser Gly Leu Ile Thr Gly Phe
1               5                   10                  15

Arg Ser Asp Ser Ser Ser Leu Pro Pro Lys Leu Leu Leu Val Ser
                20                  25                  30

Phe Asp Gly Phe Arg Ala Asp Tyr Leu Lys Asn Tyr Glu Phe Pro His
            35                  40                  45

Leu Gln Asn Phe Ile Lys Glu Gly Val Leu Val Glu His Val Lys Asn
    50                  55                  60

Val Phe Ile Thr Lys Thr Phe Pro Asn His Tyr Ser Ile Val Thr Gly
65                  70                  75                  80

Leu Tyr Glu Glu Ser His Gly Ile Val Ala Asn Ser Met Tyr Asp Ala
                85                  90                  95

Val Thr Lys Lys His Phe Ser Asp Ser Asn Asp Lys Asp Pro Phe Trp
            100                 105                 110

Trp Asn Glu Ala Val Pro Ile Trp Val Thr Asn Gln Leu Gln Glu Asn
        115                 120                 125

Arg Ser Ser Ala Ala Ala Met Trp Pro Gly Thr Asp Val Pro Ile His
    130                 135                 140

Asp Thr Ile Ser Ser Tyr Phe Met Asn Tyr Asn Ser Ser Val Ser Phe
145                 150                 155                 160

Glu Glu Arg Leu Asn Asn Ile Thr Met Trp Leu Asn Asn Ser Asn Pro
                165                 170                 175

Pro Val Thr Phe Ala Thr Leu Tyr Trp Glu Glu Pro Asp Ala Ser Gly
            180                 185                 190

His Lys Tyr Gly Pro Glu Asp Lys Glu Asn Met Ser Arg Val Leu Lys
        195                 200                 205

Lys Ile Asp Asp Leu Ile Gly Asp Leu Val Gln Arg Leu Lys Met Leu
    210                 215                 220

Gly Leu Trp Glu Asn Leu Asn Val Ile Ile Thr Ser Asp His Gly Met
225                 230                 235                 240

Thr Gln Cys Ser Gln Asp Arg Leu Ile Asn Leu Asp Ser Cys Ile Asp
                245                 250                 255

His Ser Tyr Tyr Thr Leu Ile Asp Leu Ser Pro Val Ala Ala Ile Leu
            260                 265                 270
```

-continued

```
Pro Lys Ile Asn Arg Thr Glu Val Tyr Asn Lys Leu Lys Asn Cys Ser
            275                 280                 285
Pro His Met Asn Val Tyr Leu Lys Glu Asp Ile Pro Asn Arg Phe Tyr
        290                 295                 300
Tyr Gln His Asn Asp Arg Ile Gln Pro Ile Ile Leu Val Ala Asp Glu
305                 310                 315                 320
Gly Trp Thr Ile Val Leu Asn Glu Ser Ser Gln Lys Leu Gly Asp His
                325                 330                 335
Gly Tyr Asp Asn Ser Leu Pro Ser Met His Pro Phe Leu Ala Ala His
            340                 345                 350
Gly Pro Ala Phe His Lys Gly Tyr Lys His Ser Thr Ile Asn Ile Val
        355                 360                 365
Asp Ile Tyr Pro Met Met Cys His Ile Leu Gly Leu Lys Pro His Pro
370                 375                 380
Asn Asn Gly Thr Phe Gly His Thr Lys Cys Leu Leu Val Asp Gln Trp
385                 390                 395                 400
Cys Ile Asn Leu Pro Glu Ala Ile Ala Ile Val Ile Gly Ser Leu Leu
                405                 410                 415
Val Leu Thr Met Leu Thr Cys Leu Ile Ile Ile Met Gln Asn Arg Leu
            420                 425                 430
Ser Val Pro Arg Pro Phe Ser Arg Leu Gln Leu Gln Glu Asp Asp Asp
        435                 440                 445
Asp Pro Leu Ile Gly
    450

<210> SEQ ID NO 4
<211> LENGTH: 3
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(3)
<223> OTHER INFORMATION: the tripeptide is present n times, wherein n is
      integer ranging from 1 to 10

<400> SEQUENCE: 4

Asp Ser Ser
1

<210> SEQ ID NO 5
<211> LENGTH: 3
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(3)
<223> OTHER INFORMATION: the tripeptide is present n times, wherein n is
      an integer ranging from 1 to 10

<400> SEQUENCE: 5

Glu Ser Ser
1

<210> SEQ ID NO 6
<211> LENGTH: 3
<212> TYPE: PRT
<213> ORGANISM: Artificial Sequence
<220> FEATURE:
<223> OTHER INFORMATION: chemically synthesized
```

```
<220> FEATURE:
<221> NAME/KEY: REPEAT
<222> LOCATION: (1)..(3)
<223> OTHER INFORMATION: the tripeptide is present n times, wherein n is
      integer ranging from 1 to 10

<400> SEQUENCE: 6

Arg Gln Gln
1

<210> SEQ ID NO 7
<211> LENGTH: 2
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(2)
<223> OTHER INFORMATION: the dipeptide is present n times, wherein n is
      integer ranging from 1 to 10

<400> SEQUENCE: 7

Lys Arg
1

<210> SEQ ID NO 8
<211> LENGTH: 1
<212> TYPE: PRT
<213> ORGANISM: Artificial Sequence
<220> FEATURE:
<223> OTHER INFORMATION: chemically synthesized
<220> FEATURE:
<221> NAME/KEY: REPEAT
<222> LOCATION: (1)..(1)
<223> OTHER INFORMATION: the amino acid is present n times, wherein n is
      integer ranging from 1 to 10

<400> SEQUENCE: 8

Arg
1

<210> SEQ ID NO 9
<211> LENGTH: 16
<212> TYPE: PRT
<213> ORGANISM: Artificial Sequence
<220> FEATURE:
<223> OTHER INFORMATION: chemically synthesized

<400> SEQUENCE: 9

Asp Ser Ser Ser Glu Glu Lys Phe Leu Arg Arg Ile Gly Arg Phe Gly
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: chemically synthesized

<400> SEQUENCE: 10

Glu Glu Glu Glu Glu Glu Glu Pro Arg Gly Asp Thr
1               5                   10

<210> SEQ ID NO 11
<211> LENGTH: 12
<212> TYPE: PRT
<213> ORGANISM: Artificial Sequence
<220> FEATURE:
```

-continued

```
<223> OTHER INFORMATION: chemically synthesized

<400> SEQUENCE: 11

Ala Pro Trp His Leu Ser Ser Gln Tyr Ser Arg Thr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: chemically synthesized

<400> SEQUENCE: 12

Ser Thr Leu Pro Ile Pro His Glu Phe Ser Arg Glu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: chemically synthesized

<400> SEQUENCE: 13

Val Thr Lys His Leu Asn Gln Ile Ser Gln Ser Tyr
1               5                   10

<210> SEQ ID NO 14
<211> LENGTH: 1
<212> TYPE: PRT
<213> ORGANISM: Artificial Sequence
<220> FEATURE:
<223> OTHER INFORMATION: chemically sysnthesized
<220> FEATURE:
<221> NAME/KEY: REPEAT
<222> LOCATION: (1)..(1)
<223> OTHER INFORMATION: the amino acid is present m times, wherein m is
      an integer ranging from 1 to 15

<400> SEQUENCE: 14

Glu
1

<210> SEQ ID NO 15
<211> LENGTH: 925
<212> TYPE: PRT
<213> ORGANISM: Artificial Sequence
<220> FEATURE:
<223> OTHER INFORMATION: chemically synthesized

<400> SEQUENCE: 15

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95
```

```
Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
            245                 250                 255

Phe Pro Asn His Tyr Ser Ile Val Thr Gly Leu Tyr Pro Glu Ser His
        260                 265                 270

Gly Ile Ile Asp Asn Lys Met Tyr Asp Pro Lys Met Asn Ala Ser Phe
    275                 280                 285

Ser Leu Lys Ser Lys Glu Lys Phe Asn Pro Glu Trp Tyr Lys Gly Glu
290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
            325                 330                 335

Tyr Lys Met Tyr Asn Gly Ser Val Pro Phe Glu Glu Arg Ile Leu Ala
        340                 345                 350

Val Leu Gln Trp Leu Gln Leu Pro Lys Asp Glu Arg Pro His Phe Tyr
    355                 360                 365

Thr Leu Tyr Leu Glu Glu Pro Asp Ser Ser Gly His Ser Tyr Gly Pro
370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
            405                 410                 415

Asn Leu Ile Leu Ile Ser Asp His Gly Met Glu Gln Gly Ser Cys Lys
        420                 425                 430

Lys Tyr Ile Tyr Leu Asn Lys Tyr Leu Gly Asp Val Lys Asn Ile Lys
    435                 440                 445

Val Ile Tyr Gly Pro Ala Ala Arg Leu Arg Pro Ser Asp Val Pro Asp
450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
            485                 490                 495

Lys Arg Leu His Phe Ala Lys Ser Asp Arg Ile Glu Pro Leu Thr Phe
        500                 505                 510

Tyr Leu Asp Pro Gln Trp Gln Leu Ala Leu Asn Pro Ser Glu Arg Lys
```

```
            515                 520                 525
Tyr Cys Gly Ser Gly Phe His Gly Ser Asp Asn Val Phe Ser Asn Met
530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
                580                 585                 590

His Leu Leu Lys Asn Pro Val Tyr Thr Pro Lys His Pro Lys Glu Val
                595                 600                 605

His Pro Leu Val Gln Cys Pro Phe Thr Arg Asn Pro Arg Asp Asn Leu
                610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
                660                 665                 670

Leu Leu Ser Gln His Gln Phe Met Ser Gly Tyr Ser Gln Asp Ile Leu
                675                 680                 685

Met Pro Leu Trp Thr Ser Tyr Thr Val Asp Arg Asn Asp Ser Phe Ser
690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
                740                 745                 750

Tyr Ser Glu Ala Leu Leu Thr Thr Asn Ile Val Pro Met Tyr Gln Ser
                755                 760                 765

Phe Gln Val Ile Trp Arg Tyr Phe His Asp Thr Leu Leu Arg Lys Tyr
                770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
                820                 825                 830

Ile Val Leu Thr Ser Cys Lys Asp Thr Ser Gln Thr Pro Leu His Cys
                835                 840                 845

Glu Asn Leu Asp Thr Leu Ala Phe Ile Leu Pro His Arg Thr Asp Asn
                850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
                900                 905                 910

Lys Leu Lys Thr His Leu Pro Thr Phe Ser Gln Glu Asp
                915                 920                 925

<210> SEQ ID NO 16
```

<211> LENGTH: 1155
<212> TYPE: PRT
<213> ORGANISM: Artificial Sequence
<220> FEATURE:
<223> OTHER INFORMATION: chemically synthesized

<400> SEQUENCE: 16

```
Met Glu Arg Asp Gly Cys Ala Gly Gly Gly Ser Arg Gly Gly Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
        115                 120                 125

Leu Gly Asn Cys Cys Leu Asp Tyr Gln Glu Thr Cys Ile Glu Pro Glu
    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380
```

```
Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
            405                 410                 415

Asn Leu Ile Leu Ile Ser Asp His Gly Met Glu Gln Gly Ser Cys Lys
        420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800
```

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
        820                 825                 830

Ile Val Leu Thr Ser Cys Lys Asp Thr Ser Gln Thr Pro Leu His Cys
            835                 840                 845

Glu Asn Leu Asp Thr Leu Ala Phe Ile Leu Pro His Arg Thr Asp Asn
850                 855                 860

Ser Glu Ser Cys Val His Gly Lys His Asp Ser Ser Trp Val Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp Leu Ile Asn
        915                 920                 925

Asp Lys Thr His Thr Cys Pro Cys Pro Ala Pro Glu Leu Leu Gly
    930                 935                 940

Gly Pro Ser Val Phe Leu Phe Pro Pro Lys Pro Lys Asp Thr Leu Met
945                 950                 955                 960

Ile Ser Arg Thr Pro Glu Val Thr Cys Val Val Val Asp Val Ser His
                965                 970                 975

Glu Asp Pro Glu Val Lys Phe Asn Trp Tyr Val Asp Gly Val Glu Val
            980                 985                 990

His Asn Ala Lys Thr Lys Pro Arg Glu Glu Gln Tyr Asn Ser Thr Tyr
        995                 1000                1005

Arg Val Val Ser Val Leu Thr Val Leu His Gln Asp Trp Leu Asn
    1010                1015                1020

Gly Lys Glu Tyr Lys Cys Lys Val Ser Asn Lys Ala Leu Pro Ala
    1025                1030                1035

Pro Ile Glu Lys Thr Ile Ser Lys Ala Lys Gly Gln Pro Arg Glu
    1040                1045                1050

Pro Gln Val Tyr Thr Leu Pro Pro Ser Arg Glu Glu Met Thr Lys
    1055                1060                1065

Asn Gln Val Ser Leu Thr Cys Leu Val Lys Gly Phe Tyr Pro Ser
    1070                1075                1080

Asp Ile Ala Val Glu Trp Glu Ser Asn Gly Gln Pro Glu Asn Asn
    1085                1090                1095

Tyr Lys Thr Thr Pro Pro Val Leu Asp Ser Asp Gly Ser Phe Phe
    1100                1105                1110

Leu Tyr Ser Lys Leu Thr Val Asp Lys Ser Arg Trp Gln Gln Gly
    1115                1120                1125

Asn Val Phe Ser Cys Ser Val Met His Glu Ala Leu His Asn His
    1130                1135                1140

Tyr Thr Gln Lys Ser Leu Ser Leu Ser Pro Gly Lys
    1145                1150                1155

<210> SEQ ID NO 17
<211> LENGTH: 852
<212> TYPE: PRT
<213> ORGANISM: Artificial Sequence
<220> FEATURE:
<223> OTHER INFORMATION: chemically synthesized

<400> SEQUENCE: 17

```
Met Arg Gly Pro Ala Val Leu Leu Thr Val Ala Leu Ala Thr Leu Leu
1               5                   10                  15

Ala Pro Gly Ala Gly Ala Gly Leu Lys Pro Ser Cys Ala Lys Glu Val
            20                  25                  30

Lys Ser Cys Lys Gly Arg Cys Phe Glu Arg Thr Phe Gly Asn Cys Arg
                35                  40                  45

Cys Asp Ala Ala Cys Val Glu Leu Gly Asn Cys Cys Leu Asp Tyr Gln
        50                  55                  60

Glu Thr Cys Ile Glu Pro Glu His Ile Trp Thr Cys Asn Lys Phe Arg
65                  70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Pro Cys Glu Ser Ile Asn Glu Pro
            115                 120                 125

Gln Cys Pro Ala Gly Phe Glu Thr Pro Thr Leu Leu Phe Ser Leu
    130                 135                 140

Asp Gly Phe Arg Ala Glu Tyr Leu His Thr Trp Gly Leu Leu Pro
145                 150                 155                 160

Val Ile Ser Lys Leu Lys Lys Cys Gly Thr Tyr Thr Lys Asn Met Arg
                165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
            195                 200                 205

Pro Lys Met Asn Ala Ser Phe Ser Leu Lys Ser Lys Glu Lys Phe Asn
        210                 215                 220

Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
            260                 265                 270

Phe Glu Glu Arg Ile Leu Ala Val Leu Gln Trp Leu Gln Leu Pro Lys
    275                 280                 285

Asp Glu Arg Pro His Phe Tyr Thr Leu Tyr Leu Glu Glu Pro Asp Ser
    290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
            340                 345                 350

Met Glu Gln Gly Ser Cys Lys Lys Tyr Ile Tyr Leu Asn Lys Tyr Leu
            355                 360                 365

Gly Asp Val Lys Asn Ile Lys Val Ile Tyr Gly Pro Ala Ala Arg Leu
        370                 375                 380

Arg Pro Ser Asp Val Pro Asp Lys Tyr Tyr Ser Phe Asn Tyr Glu Gly
385                 390                 395                 400

Ile Ala Arg Asn Leu Ser Cys Arg Glu Pro Asn Gln His Phe Lys Pro
                405                 410                 415

Tyr Leu Lys His Phe Leu Pro Lys Arg Leu His Phe Ala Lys Ser Asp
```

```
                420             425             430
Arg Ile Glu Pro Leu Thr Phe Tyr Leu Asp Pro Gln Trp Gln Leu Ala
            435             440             445
Leu Asn Pro Ser Glu Arg Lys Tyr Cys Gly Ser Gly Phe His Gly Ser
        450             455             460
Asp Asn Val Phe Ser Asn Met Gln Ala Leu Phe Val Gly Tyr Gly Pro
465             470             475             480
Gly Phe Lys His Gly Ile Glu Ala Asp Thr Phe Glu Asn Ile Glu Val
            485             490             495
Tyr Asn Leu Met Cys Asp Leu Leu Asn Leu Thr Pro Ala Pro Asn Asn
        500             505             510
Gly Thr His Gly Ser Leu Asn His Leu Leu Lys Asn Pro Val Tyr Thr
        515             520             525
Pro Lys His Pro Lys Glu Val His Pro Leu Val Gln Cys Pro Phe Thr
        530             535             540
Arg Asn Pro Arg Asp Asn Leu Gly Cys Ser Cys Asn Pro Ser Ile Leu
545             550             555             560
Pro Ile Glu Asp Phe Gln Thr Gln Phe Asn Leu Thr Val Ala Glu Glu
            565             570             575
Lys Ile Ile Lys His Glu Thr Leu Pro Tyr Gly Arg Pro Arg Val Leu
        580             585             590
Gln Lys Glu Asn Thr Ile Cys Leu Leu Ser Gln His Gln Phe Met Ser
        595             600             605
Gly Tyr Ser Gln Asp Ile Leu Met Pro Leu Trp Thr Ser Tyr Thr Val
        610             615             620
Asp Arg Asn Asp Ser Phe Ser Thr Glu Asp Phe Ser Asn Cys Leu Tyr
625             630             635             640
Gln Asp Phe Arg Ile Pro Leu Ser Pro Val His Lys Cys Ser Phe Tyr
            645             650             655
Lys Asn Asn Thr Lys Val Ser Tyr Gly Phe Leu Ser Pro Pro Gln Leu
        660             665             670
Asn Lys Asn Ser Ser Gly Ile Tyr Ser Glu Ala Leu Leu Thr Thr Asn
        675             680             685
Ile Val Pro Met Tyr Gln Ser Phe Gln Val Ile Trp Arg Tyr Phe His
        690             695             700
Asp Thr Leu Leu Arg Lys Tyr Ala Glu Glu Arg Asn Gly Val Asn Val
705             710             715             720
Val Ser Gly Pro Val Phe Asp Phe Asp Tyr Asp Gly Arg Cys Asp Ser
            725             730             735
Leu Glu Asn Leu Arg Gln Lys Arg Arg Val Ile Arg Asn Gln Glu Ile
        740             745             750
Leu Ile Pro Thr His Phe Phe Ile Val Leu Thr Ser Cys Lys Asp Thr
        755             760             765
Ser Gln Thr Pro Leu His Cys Glu Asn Leu Asp Thr Leu Ala Phe Ile
        770             775             780
Leu Pro His Arg Thr Asp Asn Ser Glu Ser Cys Val His Gly Lys His
785             790             795             800
Asp Ser Ser Trp Val Glu Glu Leu Leu Met Leu His Arg Ala Arg Ile
            805             810             815
Thr Asp Val Glu His Ile Thr Gly Leu Ser Phe Tyr Gln Gln Arg Lys
        820             825             830
Glu Pro Val Ser Asp Ile Leu Lys Leu Lys Thr His Leu Pro Thr Phe
        835             840             845
```

```
Ser Gln Glu Asp
        850

<210> SEQ ID NO 18
<211> LENGTH: 1082
<212> TYPE: PRT
<213> ORGANISM: Artificial Sequence
<220> FEATURE:
<223> OTHER INFORMATION: chemically synthesized

<400> SEQUENCE: 18

Met Arg Gly Pro Ala Val Leu Leu Thr Val Ala Leu Ala Thr Leu Leu
1               5                   10                  15

Ala Pro Gly Ala Gly Ala Gly Leu Lys Pro Ser Cys Ala Lys Glu Val
            20                  25                  30

Lys Ser Cys Lys Gly Arg Cys Phe Glu Arg Thr Phe Gly Asn Cys Arg
        35                  40                  45

Cys Asp Ala Ala Cys Val Glu Leu Gly Asn Cys Cys Leu Asp Tyr Gln
    50                  55                  60

Glu Thr Cys Ile Glu Pro Glu His Ile Trp Thr Cys Asn Lys Phe Arg
65              70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Glu Pro Cys Glu Ser Ile Asn Glu Pro
        115                 120                 125

Gln Cys Pro Ala Gly Phe Glu Thr Pro Pro Thr Leu Leu Phe Ser Leu
    130                 135                 140

Asp Gly Phe Arg Ala Glu Tyr Leu His Thr Trp Gly Gly Leu Leu Pro
145                 150                 155                 160

Val Ile Ser Lys Leu Lys Lys Cys Gly Thr Tyr Thr Lys Asn Met Arg
                165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
        195                 200                 205

Pro Lys Met Asn Ala Ser Phe Ser Leu Lys Ser Lys Glu Lys Phe Asn
    210                 215                 220

Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
            260                 265                 270

Phe Glu Glu Arg Ile Leu Ala Val Leu Gln Trp Leu Gln Leu Pro Lys
        275                 280                 285

Asp Glu Arg Pro His Phe Tyr Thr Leu Tyr Leu Glu Glu Pro Asp Ser
    290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
            340                 345                 350
```

```
Met Glu Gln Gly Ser Cys Lys Lys Tyr Ile Tyr Leu Asn Lys Tyr Leu
            355                 360                 365
Gly Asp Val Lys Asn Ile Lys Val Ile Tyr Gly Pro Ala Ala Arg Leu
        370                 375                 380
Arg Pro Ser Asp Val Pro Asp Lys Tyr Tyr Ser Phe Asn Tyr Glu Gly
385                 390                 395                 400
Ile Ala Arg Asn Leu Ser Cys Arg Glu Pro Asn Gln His Phe Lys Pro
                405                 410                 415
Tyr Leu Lys His Phe Leu Pro Lys Arg Leu His Phe Ala Lys Ser Asp
            420                 425                 430
Arg Ile Glu Pro Leu Thr Phe Tyr Leu Asp Pro Gln Trp Gln Leu Ala
            435                 440                 445
Leu Asn Pro Ser Glu Arg Lys Tyr Cys Gly Ser Gly Phe His Gly Ser
        450                 455                 460
Asp Asn Val Phe Ser Asn Met Gln Ala Leu Phe Val Gly Tyr Gly Pro
465                 470                 475                 480
Gly Phe Lys His Gly Ile Glu Ala Asp Thr Phe Glu Asn Ile Glu Val
                485                 490                 495
Tyr Asn Leu Met Cys Asp Leu Leu Asn Leu Thr Pro Ala Pro Asn Asn
            500                 505                 510
Gly Thr His Gly Ser Leu Asn His Leu Leu Lys Asn Pro Val Tyr Thr
        515                 520                 525
Pro Lys His Pro Lys Glu Val His Pro Leu Val Gln Cys Pro Phe Thr
        530                 535                 540
Arg Asn Pro Arg Asp Asn Leu Gly Cys Ser Cys Asn Pro Ser Ile Leu
545                 550                 555                 560
Pro Ile Glu Asp Phe Gln Thr Gln Phe Asn Leu Thr Val Ala Glu Glu
                565                 570                 575
Lys Ile Ile Lys His Glu Thr Leu Pro Tyr Gly Arg Pro Arg Val Leu
            580                 585                 590
Gln Lys Glu Asn Thr Ile Cys Leu Leu Ser Gln His Gln Phe Met Ser
        595                 600                 605
Gly Tyr Ser Gln Asp Ile Leu Met Pro Leu Trp Thr Ser Tyr Thr Val
        610                 615                 620
Asp Arg Asn Asp Ser Phe Ser Thr Glu Asp Phe Ser Asn Cys Leu Tyr
625                 630                 635                 640
Gln Asp Phe Arg Ile Pro Leu Ser Pro Val His Lys Cys Ser Phe Tyr
                645                 650                 655
Lys Asn Asn Thr Lys Val Ser Tyr Gly Phe Leu Ser Pro Pro Gln Leu
            660                 665                 670
Asn Lys Asn Ser Ser Gly Ile Tyr Ser Glu Ala Leu Leu Thr Thr Asn
        675                 680                 685
Ile Val Pro Met Tyr Gln Ser Phe Gln Val Ile Trp Arg Tyr Phe His
        690                 695                 700
Asp Thr Leu Leu Arg Lys Tyr Ala Glu Glu Arg Asn Gly Val Asn Val
705                 710                 715                 720
Val Ser Gly Pro Val Phe Asp Phe Asp Tyr Asp Gly Arg Cys Asp Ser
                725                 730                 735
Leu Glu Asn Leu Arg Gln Lys Arg Arg Val Ile Arg Asn Gln Glu Ile
            740                 745                 750
Leu Ile Pro Thr His Phe Phe Ile Val Leu Thr Ser Cys Lys Asp Thr
        755                 760                 765
```

Ser Gln Thr Pro Leu His Cys Glu Asn Leu Asp Thr Leu Ala Phe Ile
770                 775                 780

Leu Pro His Arg Thr Asp Asn Ser Glu Ser Cys Val His Gly Lys His
785                 790                 795                 800

Asp Ser Ser Trp Val Glu Glu Leu Leu Met Leu His Arg Ala Arg Ile
            805                 810                 815

Thr Asp Val Glu His Ile Thr Gly Leu Ser Phe Tyr Gln Gln Arg Lys
            820                 825                 830

Glu Pro Val Ser Asp Ile Leu Lys Leu Lys Thr His Leu Pro Thr Phe
            835                 840                 845

Ser Gln Glu Asp Leu Ile Asn Asp Lys Thr His Thr Cys Pro Pro Cys
850                 855                 860

Pro Ala Pro Glu Leu Leu Gly Gly Pro Ser Val Phe Leu Phe Pro Pro
865                 870                 875                 880

Lys Pro Lys Asp Thr Leu Met Ile Ser Arg Thr Pro Glu Val Thr Cys
            885                 890                 895

Val Val Val Asp Val Ser His Glu Asp Pro Glu Val Lys Phe Asn Trp
            900                 905                 910

Tyr Val Asp Gly Val Glu Val His Asn Ala Lys Thr Lys Pro Arg Glu
            915                 920                 925

Glu Gln Tyr Asn Ser Thr Tyr Arg Val Val Ser Val Leu Thr Val Leu
930                 935                 940

His Gln Asp Trp Leu Asn Gly Lys Glu Tyr Lys Cys Lys Val Ser Asn
945                 950                 955                 960

Lys Ala Leu Pro Ala Pro Ile Glu Lys Thr Ile Ser Lys Ala Lys Gly
            965                 970                 975

Gln Pro Arg Glu Pro Gln Val Tyr Thr Leu Pro Pro Ser Arg Glu Glu
            980                 985                 990

Met Thr Lys Asn Gln Val Ser Leu Thr Cys Leu Val Lys Gly Phe Tyr
            995                 1000                1005

Pro Ser Asp Ile Ala Val Glu Trp Glu Ser Asn Gly Gln Pro Glu
    1010                1015                1020

Asn Asn Tyr Lys Thr Thr Pro Pro Val Leu Asp Ser Asp Gly Ser
    1025                1030                1035

Phe Phe Leu Tyr Ser Lys Leu Thr Val Asp Lys Ser Arg Trp Gln
    1040                1045                1050

Gln Gly Asn Val Phe Ser Cys Ser Val Met His Glu Ala Leu His
    1055                1060                1065

Asn His Tyr Thr Gln Lys Ser Leu Ser Leu Ser Pro Gly Lys
    1070                1075                1080

<210> SEQ ID NO 19
<211> LENGTH: 849
<212> TYPE: PRT
<213> ORGANISM: Artificial Sequence
<220> FEATURE:
<223> OTHER INFORMATION: chemically synthesized

<400> SEQUENCE: 19

Met Arg Gly Pro Ala Val Leu Leu Thr Val Ala Leu Ala Thr Leu Leu
1               5                   10                  15

Ala Pro Gly Ala Gly Ala Pro Ser Cys Ala Lys Glu Val Lys Ser Cys
            20                  25                  30

Lys Gly Arg Cys Phe Glu Arg Thr Phe Gly Asn Cys Arg Cys Asp Ala
        35                  40                  45

```
Ala Cys Val Glu Leu Gly Asn Cys Cys Leu Asp Tyr Gln Glu Thr Cys
 50                  55                  60

Ile Glu Pro Glu His Ile Trp Thr Cys Asn Lys Phe Arg Cys Gly Glu
 65                  70                  75                  80

Lys Arg Leu Thr Arg Ser Leu Cys Ala Cys Ser Asp Asp Cys Lys Asp
                 85                  90                  95

Lys Gly Asp Cys Cys Ile Asn Tyr Ser Ser Val Cys Gln Gly Glu Lys
                100                 105                 110

Ser Trp Val Glu Glu Pro Cys Glu Ser Ile Asn Glu Pro Gln Cys Pro
                115                 120                 125

Ala Gly Phe Glu Thr Pro Pro Thr Leu Leu Phe Ser Leu Asp Gly Phe
                130                 135                 140

Arg Ala Glu Tyr Leu His Thr Trp Gly Gly Leu Leu Pro Val Ile Ser
145                 150                 155                 160

Lys Leu Lys Lys Cys Gly Thr Tyr Thr Lys Asn Met Arg Pro Val Tyr
                165                 170                 175

Pro Thr Lys Thr Phe Pro Asn His Tyr Ser Ile Val Thr Gly Leu Tyr
                180                 185                 190

Pro Glu Ser His Gly Ile Ile Asp Asn Lys Met Tyr Asp Pro Lys Met
                195                 200                 205

Asn Ala Ser Phe Ser Leu Lys Ser Lys Glu Lys Phe Asn Pro Glu Trp
210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
                260                 265                 270

Arg Ile Leu Ala Val Leu Gln Trp Leu Gln Leu Pro Lys Asp Glu Arg
                275                 280                 285

Pro His Phe Tyr Thr Leu Tyr Leu Glu Glu Pro Asp Ser Ser Gly His
                290                 295                 300

Ser Tyr Gly Pro Val Ser Ser Glu Val Ile Lys Ala Leu Gln Arg Val
305                 310                 315                 320

Asp Gly Met Val Gly Met Leu Met Asp Gly Leu Lys Glu Leu Asn Leu
                325                 330                 335

His Arg Cys Leu Asn Leu Ile Leu Ile Ser Asp His Gly Met Glu Gln
                340                 345                 350

Gly Ser Cys Lys Lys Tyr Ile Tyr Leu Asn Lys Tyr Leu Gly Asp Val
                355                 360                 365

Lys Asn Ile Lys Val Ile Tyr Gly Pro Ala Ala Arg Leu Arg Pro Ser
                370                 375                 380

Asp Val Pro Asp Lys Tyr Tyr Ser Phe Asn Tyr Glu Gly Ile Ala Arg
385                 390                 395                 400

Asn Leu Ser Cys Arg Glu Pro Asn Gln His Phe Lys Pro Tyr Leu Lys
                405                 410                 415

His Phe Leu Pro Lys Arg Leu His Phe Ala Lys Ser Asp Arg Ile Glu
                420                 425                 430

Pro Leu Thr Phe Tyr Leu Asp Pro Gln Trp Gln Leu Ala Leu Asn Pro
                435                 440                 445

Ser Glu Arg Lys Tyr Cys Gly Ser Gly Phe His Gly Ser Asp Asn Val
450                 455                 460

Phe Ser Asn Met Gln Ala Leu Phe Val Gly Tyr Gly Pro Gly Phe Lys
```

```
            465                 470                 475                 480
His Gly Ile Glu Ala Asp Thr Phe Glu Asn Ile Glu Val Tyr Asn Leu
                    485                 490                 495

Met Cys Asp Leu Leu Asn Leu Thr Pro Ala Pro Asn Asn Gly Thr His
                500                 505                 510

Gly Ser Leu Asn His Leu Leu Lys Asn Pro Val Tyr Thr Pro Lys His
            515                 520                 525

Pro Lys Glu Val His Pro Leu Val Gln Cys Pro Phe Thr Arg Asn Pro
        530                 535                 540

Arg Asp Asn Leu Gly Cys Ser Cys Asn Pro Ser Ile Leu Pro Ile Glu
545                 550                 555                 560

Asp Phe Gln Thr Gln Phe Asn Leu Thr Val Ala Glu Glu Lys Ile Ile
                    565                 570                 575

Lys His Glu Thr Leu Pro Tyr Gly Arg Pro Arg Val Leu Gln Lys Glu
                580                 585                 590

Asn Thr Ile Cys Leu Leu Ser Gln His Gln Phe Met Ser Gly Tyr Ser
            595                 600                 605

Gln Asp Ile Leu Met Pro Leu Trp Thr Ser Tyr Thr Val Asp Arg Asn
        610                 615                 620

Asp Ser Phe Ser Thr Glu Asp Phe Ser Asn Cys Leu Tyr Gln Asp Phe
625                 630                 635                 640

Arg Ile Pro Leu Ser Pro Val His Lys Cys Ser Phe Tyr Lys Asn Asn
                    645                 650                 655

Thr Lys Val Ser Tyr Gly Phe Leu Ser Pro Pro Gln Leu Asn Lys Asn
                660                 665                 670

Ser Ser Gly Ile Tyr Ser Glu Ala Leu Leu Thr Thr Asn Ile Val Pro
            675                 680                 685

Met Tyr Gln Ser Phe Gln Val Ile Trp Arg Tyr Phe His Asp Thr Leu
        690                 695                 700

Leu Arg Lys Tyr Ala Glu Glu Arg Asn Gly Val Asn Val Val Ser Gly
705                 710                 715                 720

Pro Val Phe Asp Phe Asp Tyr Asp Gly Arg Cys Asp Ser Leu Glu Asn
                    725                 730                 735

Leu Arg Gln Lys Arg Arg Val Ile Arg Asn Gln Glu Ile Leu Ile Pro
                740                 745                 750

Thr His Phe Phe Ile Val Leu Thr Ser Cys Lys Asp Thr Ser Gln Thr
            755                 760                 765

Pro Leu His Cys Glu Asn Leu Asp Thr Leu Ala Phe Ile Leu Pro His
        770                 775                 780

Arg Thr Asp Asn Ser Glu Ser Cys Val His Gly Lys His Asp Ser Ser
785                 790                 795                 800

Trp Val Glu Glu Leu Leu Met Leu His Arg Ala Arg Ile Thr Asp Val
                    805                 810                 815

Glu His Ile Thr Gly Leu Ser Phe Tyr Gln Gln Arg Lys Glu Pro Val
                820                 825                 830

Ser Asp Ile Leu Lys Leu Lys Thr His Leu Pro Thr Phe Ser Gln Glu
            835                 840                 845

Asp

<210> SEQ ID NO 20
<211> LENGTH: 1079
<212> TYPE: PRT
<213> ORGANISM: Artificial Sequence
<220> FEATURE:
```

<223> OTHER INFORMATION: chemically synthesized

<400> SEQUENCE: 20

```
Met Arg Gly Pro Ala Val Leu Leu Thr Val Ala Leu Ala Thr Leu Leu
1               5                   10                  15
Ala Pro Gly Ala Gly Ala Pro Ser Cys Ala Lys Glu Val Lys Ser Cys
            20                  25                  30
Lys Gly Arg Cys Phe Glu Arg Thr Phe Gly Asn Cys Arg Cys Asp Ala
        35                  40                  45
Ala Cys Val Glu Leu Gly Asn Cys Cys Leu Asp Tyr Gln Glu Thr Cys
    50                  55                  60
Ile Glu Pro Glu His Ile Trp Thr Cys Asn Lys Phe Arg Cys Gly Glu
65                  70                  75                  80
Lys Arg Leu Thr Arg Ser Leu Cys Ala Cys Ser Asp Asp Cys Lys Asp
                85                  90                  95
Lys Gly Asp Cys Cys Ile Asn Tyr Ser Ser Val Cys Gln Gly Glu Lys
            100                 105                 110
Ser Trp Val Glu Glu Pro Cys Glu Ser Ile Asn Glu Pro Gln Cys Pro
        115                 120                 125
Ala Gly Phe Glu Thr Pro Pro Thr Leu Leu Phe Ser Leu Asp Gly Phe
    130                 135                 140
Arg Ala Glu Tyr Leu His Thr Trp Gly Gly Leu Leu Pro Val Ile Ser
145                 150                 155                 160
Lys Leu Lys Lys Cys Gly Thr Tyr Thr Lys Asn Met Arg Pro Val Tyr
                165                 170                 175
Pro Thr Lys Thr Phe Pro Asn His Tyr Ser Ile Val Thr Gly Leu Tyr
            180                 185                 190
Pro Glu Ser His Gly Ile Ile Asp Asn Lys Met Tyr Asp Pro Lys Met
        195                 200                 205
Asn Ala Ser Phe Ser Leu Lys Ser Lys Glu Lys Phe Asn Pro Glu Trp
    210                 215                 220
Tyr Lys Gly Glu Pro Ile Trp Val Thr Ala Lys Tyr Gln Gly Leu Lys
225                 230                 235                 240
Ser Gly Thr Phe Phe Trp Pro Gly Ser Asp Val Glu Ile Asn Gly Ile
                245                 250                 255
Phe Pro Asp Ile Tyr Lys Met Tyr Asn Gly Ser Val Pro Phe Glu Glu
            260                 265                 270
Arg Ile Leu Ala Val Leu Gln Trp Leu Gln Leu Pro Lys Asp Glu Arg
        275                 280                 285
Pro His Phe Tyr Thr Leu Tyr Leu Glu Glu Pro Asp Ser Ser Gly His
    290                 295                 300
Ser Tyr Gly Pro Val Ser Ser Glu Val Ile Lys Ala Leu Gln Arg Val
305                 310                 315                 320
Asp Gly Met Val Gly Met Leu Met Asp Gly Leu Lys Glu Leu Asn Leu
                325                 330                 335
His Arg Cys Leu Asn Leu Ile Leu Ile Ser Asp His Gly Met Glu Gln
            340                 345                 350
Gly Ser Cys Lys Lys Tyr Ile Tyr Leu Asn Lys Tyr Leu Gly Asp Val
        355                 360                 365
Lys Asn Ile Lys Val Ile Tyr Gly Pro Ala Ala Arg Leu Arg Pro Ser
    370                 375                 380
Asp Val Pro Asp Lys Tyr Tyr Ser Phe Asn Tyr Glu Gly Ile Ala Arg
385                 390                 395                 400
```

```
Asn Leu Ser Cys Arg Glu Pro Asn Gln His Phe Lys Pro Tyr Leu Lys
                405                 410                 415
His Phe Leu Pro Lys Arg Leu His Phe Ala Lys Ser Asp Arg Ile Glu
            420                 425                 430
Pro Leu Thr Phe Tyr Leu Asp Pro Gln Trp Gln Leu Ala Leu Asn Pro
        435                 440                 445
Ser Glu Arg Lys Tyr Cys Gly Ser Gly Phe His Gly Ser Asp Asn Val
    450                 455                 460
Phe Ser Asn Met Gln Ala Leu Phe Val Gly Gly Pro Gly Phe Lys
465                 470                 475                 480
His Gly Ile Glu Ala Asp Thr Phe Glu Asn Ile Glu Val Tyr Asn Leu
                485                 490                 495
Met Cys Asp Leu Leu Asn Leu Thr Pro Ala Pro Asn Asn Gly Thr His
            500                 505                 510
Gly Ser Leu Asn His Leu Leu Lys Asn Pro Val Tyr Thr Pro Lys His
        515                 520                 525
Pro Lys Glu Val His Pro Leu Val Gln Cys Pro Phe Thr Arg Asn Pro
    530                 535                 540
Arg Asp Asn Leu Gly Cys Ser Cys Asn Pro Ser Ile Leu Pro Ile Glu
545                 550                 555                 560
Asp Phe Gln Thr Gln Phe Asn Leu Thr Val Ala Glu Glu Lys Ile Ile
                565                 570                 575
Lys His Glu Thr Leu Pro Tyr Gly Arg Pro Arg Val Leu Gln Lys Glu
            580                 585                 590
Asn Thr Ile Cys Leu Leu Ser Gln His Gln Phe Met Ser Gly Tyr Ser
        595                 600                 605
Gln Asp Ile Leu Met Pro Leu Trp Thr Ser Tyr Thr Val Asp Arg Asn
    610                 615                 620
Asp Ser Phe Ser Thr Glu Asp Phe Ser Asn Cys Leu Tyr Gln Asp Phe
625                 630                 635                 640
Arg Ile Pro Leu Ser Pro Val His Lys Cys Ser Phe Tyr Lys Asn Asn
                645                 650                 655
Thr Lys Val Ser Tyr Gly Phe Leu Ser Pro Pro Gln Leu Asn Lys Asn
            660                 665                 670
Ser Ser Gly Ile Tyr Ser Glu Ala Leu Leu Thr Thr Asn Ile Val Pro
        675                 680                 685
Met Tyr Gln Ser Phe Gln Val Ile Trp Arg Tyr Phe His Asp Thr Leu
    690                 695                 700
Leu Arg Lys Tyr Ala Glu Glu Arg Asn Gly Val Asn Val Val Ser Gly
705                 710                 715                 720
Pro Val Phe Asp Phe Asp Tyr Asp Gly Arg Cys Asp Ser Leu Glu Asn
                725                 730                 735
Leu Arg Gln Lys Arg Arg Val Ile Arg Asn Gln Glu Ile Leu Ile Pro
            740                 745                 750
Thr His Phe Phe Ile Val Leu Thr Ser Cys Lys Asp Thr Ser Gln Thr
        755                 760                 765
Pro Leu His Cys Glu Asn Leu Asp Thr Leu Ala Phe Ile Leu Pro His
    770                 775                 780
Arg Thr Asp Asn Ser Glu Ser Cys Val His Gly Lys His Asp Ser Ser
785                 790                 795                 800
Trp Val Glu Glu Leu Leu Met Leu His Arg Ala Arg Ile Thr Asp Val
                805                 810                 815
Glu His Ile Thr Gly Leu Ser Phe Tyr Gln Gln Arg Lys Glu Pro Val
```

```
                820                 825                 830
Ser Asp Ile Leu Lys Leu Lys Thr His Leu Pro Thr Phe Ser Gln Glu
            835                 840                 845

Asp Leu Ile Asn Asp Lys Thr His Thr Cys Pro Pro Cys Pro Ala Pro
850                 855                 860

Glu Leu Leu Gly Gly Pro Ser Val Phe Leu Phe Pro Pro Lys Pro Lys
865                 870                 875                 880

Asp Thr Leu Met Ile Ser Arg Thr Pro Glu Val Thr Cys Val Val Val
                885                 890                 895

Asp Val Ser His Glu Asp Pro Glu Val Lys Phe Asn Trp Tyr Val Asp
            900                 905                 910

Gly Val Glu Val His Asn Ala Lys Thr Lys Pro Arg Glu Glu Gln Tyr
        915                 920                 925

Asn Ser Thr Tyr Arg Val Val Ser Val Leu Thr Val Leu His Gln Asp
    930                 935                 940

Trp Leu Asn Gly Lys Glu Tyr Lys Cys Lys Val Ser Asn Lys Ala Leu
945                 950                 955                 960

Pro Ala Pro Ile Glu Lys Thr Ile Ser Lys Ala Lys Gly Gln Pro Arg
                965                 970                 975

Glu Pro Gln Val Tyr Thr Leu Pro Pro Ser Arg Glu Glu Met Thr Lys
            980                 985                 990

Asn Gln Val Ser Leu Thr Cys Leu  Val Lys Gly Phe Tyr  Pro Ser Asp
        995                 1000                1005

Ile Ala  Val Glu Trp Glu Ser  Asn Gly Gln Pro Glu  Asn Asn Tyr
    1010                1015                1020

Lys Thr  Thr Pro Pro Val Leu  Asp Ser Asp Gly Ser  Phe Phe Leu
    1025                1030                1035

Tyr Ser  Lys Leu Thr Val Asp  Lys Ser Arg Trp Gln  Gln Gly Asn
    1040                1045                1050

Val Phe  Ser Cys Ser Val Met  His Glu Ala Leu His  Asn His Tyr
    1055                1060                1065

Thr Gln  Lys Ser Leu Ser Leu  Ser Pro Gly Lys
    1070                1075

<210> SEQ ID NO 21
<211> LENGTH: 1550
<212> TYPE: PRT
<213> ORGANISM: Artificial Sequence
<220> FEATURE:
<223> OTHER INFORMATION: chemically synthesized

<400> SEQUENCE: 21

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
        35                  40                  45

Leu Leu Ala Pro Met Asp Val Gly Glu Glu Pro Leu Glu Lys Ala Ala
    50                  55                  60

Arg Ala Arg Thr Ala Lys Asp Pro Asn Thr Tyr Lys Ile Ile Ser Leu
65                  70                  75                  80

Phe Thr Phe Ala Val Gly Val Asn Ile Cys Leu Gly Phe Thr Ala Gly
                85                  90                  95

Leu Lys Pro Ser Cys Ala Lys Glu Val Lys Ser Cys Lys Gly Arg Cys
```

```
                100                 105                 110
Phe Glu Arg Thr Phe Gly Asn Cys Arg Cys Asp Ala Ala Cys Val Glu
            115                 120                 125
Leu Gly Asn Cys Cys Leu Asp Tyr Gln Glu Thr Cys Ile Glu Pro Glu
            130                 135                 140
His Ile Trp Thr Cys Asn Lys Phe Arg Cys Gly Glu Lys Arg Leu Thr
145                 150                 155                 160
Arg Ser Leu Cys Ala Cys Ser Asp Asp Cys Lys Asp Lys Gly Asp Cys
                165                 170                 175
Cys Ile Asn Tyr Ser Ser Val Cys Gln Gly Glu Lys Ser Trp Val Glu
                180                 185                 190
Glu Pro Cys Glu Ser Ile Asn Glu Pro Gln Cys Pro Ala Gly Phe Glu
                195                 200                 205
Thr Pro Pro Thr Leu Leu Phe Ser Leu Asp Gly Phe Arg Ala Glu Tyr
            210                 215                 220
Leu His Thr Trp Gly Gly Leu Leu Pro Val Ile Ser Lys Leu Lys Lys
225                 230                 235                 240
Cys Gly Thr Tyr Thr Lys Asn Met Arg Pro Val Tyr Pro Thr Lys Thr
                245                 250                 255
Phe Pro Asn His Tyr Ser Ile Val Thr Gly Leu Tyr Pro Glu Ser His
                260                 265                 270
Gly Ile Ile Asp Asn Lys Met Tyr Asp Pro Lys Met Asn Ala Ser Phe
            275                 280                 285
Ser Leu Lys Ser Lys Glu Lys Phe Asn Pro Glu Trp Tyr Lys Gly Glu
            290                 295                 300
Pro Ile Trp Val Thr Ala Lys Tyr Gln Gly Leu Lys Ser Gly Thr Phe
305                 310                 315                 320
Phe Trp Pro Gly Ser Asp Val Glu Ile Asn Gly Ile Phe Pro Asp Ile
                325                 330                 335
Tyr Lys Met Tyr Asn Gly Ser Val Pro Phe Glu Glu Arg Ile Leu Ala
                340                 345                 350
Val Leu Gln Trp Leu Gln Leu Pro Lys Asp Glu Arg Pro His Phe Tyr
                355                 360                 365
Thr Leu Tyr Leu Glu Glu Pro Asp Ser Ser Gly His Ser Tyr Gly Pro
            370                 375                 380
Val Ser Ser Glu Val Ile Lys Ala Leu Gln Arg Val Asp Gly Met Val
385                 390                 395                 400
Gly Met Leu Met Asp Gly Leu Lys Glu Leu Asn Leu His Arg Cys Leu
                405                 410                 415
Asn Leu Ile Leu Ile Ser Asp His Gly Met Glu Gln Gly Ser Cys Lys
                420                 425                 430
Lys Tyr Ile Tyr Leu Asn Lys Tyr Leu Gly Asp Val Lys Asn Ile Lys
            435                 440                 445
Val Ile Tyr Gly Pro Ala Ala Arg Leu Arg Pro Ser Asp Val Pro Asp
            450                 455                 460
Lys Tyr Tyr Ser Phe Asn Tyr Glu Gly Ile Ala Arg Asn Leu Ser Cys
465                 470                 475                 480
Arg Glu Pro Asn Gln His Phe Lys Pro Tyr Leu Lys His Phe Leu Pro
                485                 490                 495
Lys Arg Leu His Phe Ala Lys Ser Asp Arg Ile Glu Pro Leu Thr Phe
                500                 505                 510
Tyr Leu Asp Pro Gln Trp Gln Leu Ala Leu Asn Pro Ser Glu Arg Lys
            515                 520                 525
```

```
Tyr Cys Gly Ser Gly Phe His Gly Ser Asp Asn Val Phe Ser Asn Met
        530                 535                 540
Gln Ala Leu Phe Val Gly Tyr Gly Pro Gly Phe Lys His Gly Ile Glu
545                 550                 555                 560
Ala Asp Thr Phe Glu Asn Ile Glu Val Tyr Asn Leu Met Cys Asp Leu
                565                 570                 575
Leu Asn Leu Thr Pro Ala Pro Asn Asn Gly Thr His Gly Ser Leu Asn
            580                 585                 590
His Leu Leu Lys Asn Pro Val Tyr Thr Pro Lys His Pro Lys Glu Val
        595                 600                 605
His Pro Leu Val Gln Cys Pro Phe Thr Arg Asn Pro Arg Asp Asn Leu
    610                 615                 620
Gly Cys Ser Cys Asn Pro Ser Ile Leu Pro Ile Glu Asp Phe Gln Thr
625                 630                 635                 640
Gln Phe Asn Leu Thr Val Ala Glu Glu Lys Ile Ile Lys His Glu Thr
                645                 650                 655
Leu Pro Tyr Gly Arg Pro Arg Val Leu Gln Lys Glu Asn Thr Ile Cys
            660                 665                 670
Leu Leu Ser Gln His Gln Phe Met Ser Gly Tyr Ser Gln Asp Ile Leu
        675                 680                 685
Met Pro Leu Trp Thr Ser Tyr Thr Val Asp Arg Asn Asp Ser Phe Ser
    690                 695                 700
Thr Glu Asp Phe Ser Asn Cys Leu Tyr Gln Asp Phe Arg Ile Pro Leu
705                 710                 715                 720
Ser Pro Val His Lys Cys Ser Phe Tyr Lys Asn Asn Thr Lys Val Ser
                725                 730                 735
Tyr Gly Phe Leu Ser Pro Pro Gln Leu Asn Lys Asn Ser Ser Gly Ile
            740                 745                 750
Tyr Ser Glu Ala Leu Leu Thr Thr Asn Ile Val Pro Met Tyr Gln Ser
        755                 760                 765
Phe Gln Val Ile Trp Arg Tyr Phe His Asp Thr Leu Leu Arg Lys Tyr
    770                 775                 780
Ala Glu Glu Arg Asn Gly Val Asn Val Val Ser Gly Pro Val Phe Asp
785                 790                 795                 800
Phe Asp Tyr Asp Gly Arg Cys Asp Ser Leu Glu Asn Leu Arg Gln Lys
                805                 810                 815
Arg Arg Val Ile Arg Asn Gln Glu Ile Leu Ile Pro Thr His Phe Phe
            820                 825                 830
Ile Val Leu Thr Ser Cys Lys Asp Thr Ser Gln Thr Pro Leu His Cys
        835                 840                 845
Glu Asn Leu Asp Thr Leu Ala Phe Ile Leu Pro His Arg Thr Asp Asn
850                 855                 860
Ser Glu Ser Cys Val His Gly Lys His Asp Ser Ser Trp Val Glu Glu
865                 870                 875                 880
Leu Leu Met Leu His Arg Ala Arg Ile Thr Asp Val Glu His Ile Thr
                885                 890                 895
Gly Leu Ser Phe Tyr Gln Gln Arg Lys Glu Pro Val Ser Asp Ile Leu
            900                 905                 910
Lys Leu Lys Thr His Leu Pro Thr Phe Ser Gln Glu Asp Arg Ser Gly
        915                 920                 925
Ser Gly Gly Ser Met Lys Trp Val Thr Phe Leu Leu Leu Leu Phe Val
930                 935                 940
```

-continued

```
Ser Gly Ser Ala Phe Ser Arg Gly Val Phe Arg Arg Glu Ala His Lys
945                 950                 955                 960

Ser Glu Ile Ala His Arg Tyr Asn Asp Leu Gly Glu Gln His Phe Lys
            965                 970                 975

Gly Leu Val Leu Ile Ala Phe Ser Gln Tyr Leu Gln Lys Cys Ser Tyr
        980                 985                 990

Asp Glu His Ala Lys Leu Val Gln  Glu Val Thr Asp Phe Ala Lys Thr
        995                 1000                1005

Cys Val  Ala Asp Glu Ser Ala  Ala Asn Cys Asp Lys  Ser Leu His
    1010                1015                1020

Thr Leu  Phe Gly Asp Lys Leu  Cys Ala Ile Pro Asn  Leu Arg Glu
    1025                1030                1035

Asn Tyr  Gly Glu Leu Ala Asp  Cys Cys Thr Lys Gln  Glu Pro Glu
    1040                1045                1050

Arg Asn  Glu Cys Phe Leu Gln  His Lys Asp Asp Asn  Pro Ser Leu
    1055                1060                1065

Pro Pro  Phe Glu Arg Pro Glu  Ala Glu Ala Met Cys  Thr Ser Phe
    1070                1075                1080

Lys Glu  Asn Pro Thr Thr Phe  Met Gly His Tyr Leu  His Glu Val
    1085                1090                1095

Ala Arg  Arg His Pro Tyr Phe  Tyr Ala Pro Glu Leu  Leu Tyr Tyr
    1100                1105                1110

Ala Glu  Gln Tyr Asn Glu Ile  Leu Thr Gln Cys Cys  Ala Glu Ala
    1115                1120                1125

Asp Lys  Glu Ser Cys Leu Thr  Pro Lys Leu Asp Gly  Val Lys Glu
    1130                1135                1140

Lys Ala  Leu Val Ser Ser Val  Arg Gln Arg Met Lys  Cys Ser Ser
    1145                1150                1155

Met Gln  Lys Phe Gly Glu Arg  Ala Phe Lys Ala Trp  Ala Val Ala
    1160                1165                1170

Arg Leu  Ser Gln Thr Phe Pro  Asn Ala Asp Phe Ala  Glu Ile Thr
    1175                1180                1185

Lys Leu  Ala Thr Asp Leu Thr  Lys Val Asn Lys Glu  Cys Cys His
    1190                1195                1200

Gly Asp  Leu Leu Glu Cys Ala  Asp Asp Arg Ala Glu  Leu Ala Lys
    1205                1210                1215

Tyr Met  Cys Glu Asn Gln Ala  Thr Ile Ser Ser Lys  Leu Gln Thr
    1220                1225                1230

Cys Cys  Asp Lys Pro Leu Leu  Lys Lys Ala His Cys  Leu Ser Glu
    1235                1240                1245

Val Glu  His Asp Thr Met Pro  Ala Asp Leu Pro Ala  Ile Ala Ala
    1250                1255                1260

Asp Phe  Val Glu Asp Gln Glu  Val Cys Lys Asn Tyr  Ala Glu Ala
    1265                1270                1275

Lys Asp  Val Phe Leu Gly Thr  Phe Leu Tyr Glu Tyr  Ser Arg Arg
    1280                1285                1290

His Pro  Asp Tyr Ser Val Ser  Leu Leu Leu Arg Leu  Ala Lys Lys
    1295                1300                1305

Tyr Glu  Ala Thr Leu Glu Lys  Cys Cys Ala Glu Ala  Asn Pro Pro
    1310                1315                1320

Ala Cys  Tyr Gly Thr Val Leu  Ala Glu Phe Gln Pro  Leu Val Glu
    1325                1330                1335

Glu Pro  Lys Asn Leu Val Lys  Thr Asn Cys Asp Leu  Tyr Glu Lys
```

```
                1340                1345                1350

Leu Gly Glu Tyr Gly Phe Gln Asn Ala Ile Leu Val Arg Tyr Thr
        1355                1360                1365

Gln Lys Ala Pro Gln Val Ser Thr Pro Thr Leu Val Glu Ala Ala
1370                1375                1380

Arg Asn Leu Gly Arg Val Gly Thr Lys Cys Cys Thr Leu Pro Glu
    1385                1390                1395

Asp Gln Arg Leu Pro Cys Val Glu Asp Tyr Leu Ser Ala Ile Leu
1400                1405                1410

Asn Arg Val Cys Leu Leu His Glu Lys Thr Pro Val Ser Glu His
    1415                1420                1425

Val Thr Lys Cys Cys Ser Gly Ser Leu Val Glu Arg Arg Pro Cys
1430                1435                1440

Phe Ser Ala Leu Thr Val Asp Glu Thr Tyr Val Pro Lys Glu Phe
    1445                1450                1455

Lys Ala Glu Thr Phe Thr Phe His Ser Asp Ile Cys Thr Leu Pro
1460                1465                1470

Glu Lys Glu Lys Gln Ile Lys Lys Gln Thr Ala Leu Ala Glu Leu
    1475                1480                1485

Val Lys His Lys Pro Lys Ala Thr Ala Glu Gln Leu Lys Thr Val
1490                1495                1500

Met Asp Asp Phe Ala Gln Phe Leu Asp Thr Cys Cys Lys Ala Ala
    1505                1510                1515

Asp Lys Asp Thr Cys Phe Ser Thr Glu Gly Pro Asn Leu Val Thr
1520                1525                1530

Arg Cys Lys Asp Ala Leu Ala Arg Ser Trp Ser His Pro Gln Phe
    1535                1540                1545

Glu Lys
    1550

<210> SEQ ID NO 22
<211> LENGTH: 1474
<212> TYPE: PRT
<213> ORGANISM: Artificial Sequence
<220> FEATURE:
<223> OTHER INFORMATION: chemically synthesized

<400> SEQUENCE: 22

Met Arg Gly Pro Ala Val Leu Leu Thr Val Ala Leu Ala Thr Leu Leu
1               5                   10                  15

Ala Pro Gly Ala Gly Ala Pro Ser Cys Ala Lys Glu Val Lys Ser Cys
            20                  25                  30

Lys Gly Arg Cys Phe Glu Arg Thr Phe Gly Asn Cys Arg Cys Asp Ala
        35                  40                  45

Ala Cys Val Glu Leu Gly Asn Cys Cys Leu Asp Tyr Gln Glu Thr Cys
    50                  55                  60

Ile Glu Pro Glu His Ile Trp Thr Cys Asn Lys Phe Arg Cys Gly Glu
65                  70                  75                  80

Lys Arg Leu Thr Arg Ser Leu Cys Ala Cys Ser Asp Asp Cys Lys Asp
                85                  90                  95

Lys Gly Asp Cys Cys Ile Asn Tyr Ser Ser Val Cys Gln Gly Glu Lys
            100                 105                 110

Ser Trp Val Glu Glu Pro Cys Glu Ser Ile Asn Glu Pro Gln Cys Pro
        115                 120                 125

Ala Gly Phe Glu Thr Pro Pro Thr Leu Leu Phe Ser Leu Asp Gly Phe
```

```
            130                 135                 140
Arg Ala Glu Tyr Leu His Thr Trp Gly Gly Leu Leu Pro Val Ile Ser
145                 150                 155                 160

Lys Leu Lys Lys Cys Gly Thr Tyr Thr Lys Asn Met Arg Pro Val Tyr
                165                 170                 175

Pro Thr Lys Thr Phe Pro Asn His Tyr Ser Ile Val Thr Gly Leu Tyr
            180                 185                 190

Pro Glu Ser His Gly Ile Ile Asp Asn Lys Met Tyr Asp Pro Lys Met
        195                 200                 205

Asn Ala Ser Phe Ser Leu Lys Ser Lys Glu Lys Phe Asn Pro Glu Trp
    210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
            260                 265                 270

Arg Ile Leu Ala Val Leu Gln Trp Leu Gln Leu Pro Lys Asp Glu Arg
        275                 280                 285

Pro His Phe Tyr Thr Leu Tyr Leu Glu Glu Pro Asp Ser Ser Gly His
    290                 295                 300

Ser Tyr Gly Pro Val Ser Ser Glu Val Ile Lys Ala Leu Gln Arg Val
305                 310                 315                 320

Asp Gly Met Val Gly Met Leu Met Asp Gly Leu Lys Glu Leu Asn Leu
                325                 330                 335

His Arg Cys Leu Asn Leu Ile Leu Ile Ser Asp His Gly Met Glu Gln
            340                 345                 350

Gly Ser Cys Lys Lys Tyr Ile Tyr Leu Asn Lys Tyr Leu Gly Asp Val
        355                 360                 365

Lys Asn Ile Lys Val Ile Tyr Gly Pro Ala Ala Arg Leu Arg Pro Ser
    370                 375                 380

Asp Val Pro Asp Lys Tyr Tyr Ser Phe Asn Tyr Glu Gly Ile Ala Arg
385                 390                 395                 400

Asn Leu Ser Cys Arg Glu Pro Asn Gln His Phe Lys Pro Tyr Leu Lys
                405                 410                 415

His Phe Leu Pro Lys Arg Leu His Phe Ala Lys Ser Asp Arg Ile Glu
            420                 425                 430

Pro Leu Thr Phe Tyr Leu Asp Pro Gln Trp Gln Leu Ala Leu Asn Pro
        435                 440                 445

Ser Glu Arg Lys Tyr Cys Gly Ser Gly Phe His Gly Ser Asp Asn Val
    450                 455                 460

Phe Ser Asn Met Gln Ala Leu Phe Val Gly Tyr Gly Pro Gly Phe Lys
465                 470                 475                 480

His Gly Ile Glu Ala Asp Thr Phe Glu Asn Ile Glu Val Tyr Asn Leu
                485                 490                 495

Met Cys Asp Leu Leu Asn Leu Thr Pro Ala Pro Asn Asn Gly Thr His
            500                 505                 510

Gly Ser Leu Asn His Leu Leu Lys Asn Pro Val Tyr Thr Pro Lys His
        515                 520                 525

Pro Lys Glu Val His Pro Leu Val Gln Cys Pro Phe Thr Arg Asn Pro
    530                 535                 540

Arg Asp Asn Leu Gly Cys Ser Cys Asn Pro Ser Ile Leu Pro Ile Glu
545                 550                 555                 560
```

```
Asp Phe Gln Thr Gln Phe Asn Leu Thr Val Ala Glu Glu Lys Ile Ile
                565                 570                 575

Lys His Glu Thr Leu Pro Tyr Gly Arg Pro Arg Val Leu Gln Lys Glu
            580                 585                 590

Asn Thr Ile Cys Leu Leu Ser Gln His Gln Phe Met Ser Gly Tyr Ser
        595                 600                 605

Gln Asp Ile Leu Met Pro Leu Trp Thr Ser Tyr Thr Val Asp Arg Asn
    610                 615                 620

Asp Ser Phe Ser Thr Glu Asp Phe Ser Asn Cys Leu Tyr Gln Asp Phe
625                 630                 635                 640

Arg Ile Pro Leu Ser Pro Val His Lys Cys Ser Phe Tyr Lys Asn Asn
                645                 650                 655

Thr Lys Val Ser Tyr Gly Phe Leu Ser Pro Gln Leu Asn Lys Asn
            660                 665                 670

Ser Ser Gly Ile Tyr Ser Glu Ala Leu Leu Thr Thr Asn Ile Val Pro
        675                 680                 685

Met Tyr Gln Ser Phe Gln Val Ile Trp Arg Tyr Phe His Asp Thr Leu
    690                 695                 700

Leu Arg Lys Tyr Ala Glu Glu Arg Asn Gly Val Asn Val Val Ser Gly
705                 710                 715                 720

Pro Val Phe Asp Phe Asp Tyr Asp Gly Arg Cys Asp Ser Leu Glu Asn
                725                 730                 735

Leu Arg Gln Lys Arg Arg Val Ile Arg Asn Gln Glu Ile Leu Ile Pro
            740                 745                 750

Thr His Phe Phe Ile Val Leu Thr Ser Cys Lys Asp Thr Ser Gln Thr
        755                 760                 765

Pro Leu His Cys Glu Asn Leu Asp Thr Leu Ala Phe Ile Leu Pro His
    770                 775                 780

Arg Thr Asp Asn Ser Glu Ser Cys Val His Gly Lys His Asp Ser Ser
785                 790                 795                 800

Trp Val Glu Glu Leu Leu Met Leu His Arg Ala Arg Ile Thr Asp Val
                805                 810                 815

Glu His Ile Thr Gly Leu Ser Phe Tyr Gln Arg Lys Glu Pro Val
            820                 825                 830

Ser Asp Ile Leu Lys Leu Lys Thr His Leu Pro Thr Phe Ser Gln Glu
        835                 840                 845

Asp Arg Ser Gly Ser Gly Ser Met Lys Trp Val Thr Phe Leu Leu
    850                 855                 860

Leu Leu Phe Val Ser Gly Ser Ala Phe Ser Arg Gly Val Phe Arg Arg
865                 870                 875                 880

Glu Ala His Lys Ser Glu Ile Ala His Arg Tyr Asn Asp Leu Gly Glu
                885                 890                 895

Gln His Phe Lys Gly Leu Val Leu Ile Ala Phe Ser Gln Tyr Leu Gln
            900                 905                 910

Lys Cys Ser Tyr Asp Glu His Ala Lys Leu Val Gln Glu Val Thr Asp
        915                 920                 925

Phe Ala Lys Thr Cys Val Ala Asp Glu Ser Ala Ala Asn Cys Asp Lys
    930                 935                 940

Ser Leu His Thr Leu Phe Gly Asp Lys Leu Cys Ala Ile Pro Asn Leu
945                 950                 955                 960

Arg Glu Asn Tyr Gly Glu Leu Ala Asp Cys Cys Thr Lys Gln Glu Pro
                965                 970                 975
```

-continued

Glu Arg Asn Glu Cys Phe Leu Gln His Lys Asp Asp Asn Pro Ser Leu
            980                 985                 990

Pro Pro Phe Glu Arg Pro Glu Ala Glu Ala Met Cys Thr Ser Phe Lys
        995                 1000                1005

Glu Asn Pro Thr Thr Phe Met Gly His Tyr Leu His Glu Val Ala
        1010                1015                1020

Arg Arg His Pro Tyr Phe Tyr Ala Pro Glu Leu Leu Tyr Tyr Ala
        1025                1030                1035

Glu Gln Tyr Asn Glu Ile Leu Thr Gln Cys Cys Ala Glu Ala Asp
        1040                1045                1050

Lys Glu Ser Cys Leu Thr Pro Lys Leu Asp Gly Val Lys Glu Lys
        1055                1060                1065

Ala Leu Val Ser Ser Val Arg Gln Arg Met Lys Cys Ser Ser Met
        1070                1075                1080

Gln Lys Phe Gly Glu Arg Ala Phe Lys Ala Trp Ala Val Ala Arg
        1085                1090                1095

Leu Ser Gln Thr Phe Pro Asn Ala Asp Phe Ala Glu Ile Thr Lys
        1100                1105                1110

Leu Ala Thr Asp Leu Thr Lys Val Asn Lys Glu Cys Cys His Gly
        1115                1120                1125

Asp Leu Leu Glu Cys Ala Asp Asp Arg Ala Glu Leu Ala Lys Tyr
        1130                1135                1140

Met Cys Glu Asn Gln Ala Thr Ile Ser Ser Lys Leu Gln Thr Cys
        1145                1150                1155

Cys Asp Lys Pro Leu Leu Lys Lys Ala His Cys Leu Ser Glu Val
        1160                1165                1170

Glu His Asp Thr Met Pro Ala Asp Leu Pro Ala Ile Ala Ala Asp
        1175                1180                1185

Phe Val Glu Asp Gln Glu Val Cys Lys Asn Tyr Ala Glu Ala Lys
        1190                1195                1200

Asp Val Phe Leu Gly Thr Phe Leu Tyr Glu Tyr Ser Arg Arg His
        1205                1210                1215

Pro Asp Tyr Ser Val Ser Leu Leu Leu Arg Leu Ala Lys Lys Tyr
        1220                1225                1230

Glu Ala Thr Leu Glu Lys Cys Cys Ala Glu Ala Asn Pro Pro Ala
        1235                1240                1245

Cys Tyr Gly Thr Val Leu Ala Glu Phe Gln Pro Leu Val Glu Glu
        1250                1255                1260

Pro Lys Asn Leu Val Lys Thr Asn Cys Asp Leu Tyr Glu Lys Leu
        1265                1270                1275

Gly Glu Tyr Gly Phe Gln Asn Ala Ile Leu Val Arg Tyr Thr Gln
        1280                1285                1290

Lys Ala Pro Gln Val Ser Thr Pro Thr Leu Val Glu Ala Ala Arg
        1295                1300                1305

Asn Leu Gly Arg Val Gly Thr Lys Cys Cys Thr Leu Pro Glu Asp
        1310                1315                1320

Gln Arg Leu Pro Cys Val Glu Asp Tyr Leu Ser Ala Ile Leu Asn
        1325                1330                1335

Arg Val Cys Leu Leu His Glu Lys Thr Pro Val Ser Glu His Val
        1340                1345                1350

Thr Lys Cys Cys Ser Gly Ser Leu Val Glu Arg Arg Pro Cys Phe
        1355                1360                1365

Ser Ala Leu Thr Val Asp Glu Thr Tyr Val Pro Lys Glu Phe Lys

```
                1370                1375                1380
Ala Glu Thr Phe Thr Phe His Ser Asp Ile Cys Thr Leu Pro Glu
    1385                1390                1395
Lys Glu Lys Gln Ile Lys Lys Gln Thr Ala Leu Ala Glu Leu Val
1400                1405                1410
Lys His Lys Pro Lys Ala Thr Ala Glu Gln Leu Lys Thr Val Met
    1415                1420                1425
Asp Asp Phe Ala Gln Phe Leu Asp Thr Cys Cys Lys Ala Ala Asp
    1430                1435                1440
Lys Asp Thr Cys Phe Ser Thr Glu Gly Pro Asn Leu Val Thr Arg
    1445                1450                1455
Cys Lys Asp Ala Leu Ala Arg Ser Trp Ser His Pro Gln Phe Glu
    1460                1465                1470
Lys

<210> SEQ ID NO 23
<211> LENGTH: 19
<212> TYPE: PRT
<213> ORGANISM: Artificial Sequence
<220> FEATURE:
<223> OTHER INFORMATION: chemically synthesized

<400> SEQUENCE: 23

Ile Ile Ser Leu Phe Thr Phe Ala Val Gly Val Asn Ile Cys Leu Gly
1               5                   10                  15

Phe Thr Ala

<210> SEQ ID NO 24
<211> LENGTH: 850
<212> TYPE: PRT
<213> ORGANISM: Artificial Sequence
<220> FEATURE:
<223> OTHER INFORMATION: chemically synthesized

<400> SEQUENCE: 24

Met Thr Ser Lys Phe Leu Leu Val Ser Phe Ile Leu Ala Ala Leu Ser
1               5                   10                  15

Leu Ser Thr Thr Phe Ser Leu Gln Pro Ser Cys Ala Lys Glu Val Lys
                20                  25                  30

Ser Cys Lys Gly Arg Cys Phe Glu Arg Thr Phe Ser Asn Cys Arg Cys
            35                  40                  45

Asp Ala Ala Cys Val Ser Leu Gly Asn Cys Cys Leu Asp Phe Gln Glu
        50                  55                  60

Thr Cys Val Glu Pro Thr His Ile Trp Thr Cys Asn Lys Phe Arg Cys
65                  70                  75                  80

Gly Glu Lys Arg Leu Ser Arg Phe Val Cys Ser Cys Ala Asp Asp Cys
                85                  90                  95

Lys Thr His Asn Asp Cys Cys Ile Asn Tyr Ser Ser Val Cys Gln Asp
            100                 105                 110

Lys Lys Ser Trp Val Glu Glu Thr Cys Glu Ser Ile Asp Thr Pro Glu
        115                 120                 125

Cys Pro Ala Glu Phe Glu Ser Pro Pro Thr Leu Leu Phe Ser Leu Asp
    130                 135                 140

Gly Phe Arg Ala Glu Tyr Leu His Thr Trp Gly Gly Leu Leu Pro Val
145                 150                 155                 160

Ile Ser Lys Leu Lys Asn Cys Gly Thr Tyr Thr Lys Asn Met Arg Pro
                165                 170                 175
```

-continued

```
Met Tyr Pro Thr Lys Thr Phe Pro Asn His Tyr Ser Ile Val Thr Gly
            180                 185                 190

Leu Tyr Pro Glu Ser His Gly Ile Ile Asp Asn Lys Met Tyr Asp Pro
            195                 200                 205

Lys Met Asn Ala Ser Phe Ser Leu Lys Ser Lys Glu Lys Phe Asn Pro
            210                 215                 220

Leu Trp Tyr Lys Gly Gln Pro Ile Trp Val Thr Ala Asn His Gln Glu
225                 230                 235                 240

Val Lys Ser Gly Thr Tyr Phe Trp Pro Gly Ser Asp Val Glu Ile Asp
            245                 250                 255

Gly Ile Leu Pro Asp Ile Tyr Lys Val Tyr Asn Gly Ser Val Pro Phe
            260                 265                 270

Glu Glu Arg Ile Leu Ala Val Leu Glu Trp Leu Gln Leu Pro Ser His
            275                 280                 285

Glu Arg Pro His Phe Tyr Thr Leu Tyr Leu Glu Glu Pro Asp Ser Ser
            290                 295                 300

Gly His Ser His Gly Pro Val Ser Ser Glu Val Ile Lys Ala Leu Gln
305                 310                 315                 320

Lys Val Asp Arg Leu Val Gly Met Leu Met Asp Gly Leu Lys Asp Leu
            325                 330                 335

Gly Leu Asp Lys Cys Leu Asn Leu Ile Leu Ile Ser Asp His Gly Met
            340                 345                 350

Glu Gln Gly Ser Cys Lys Lys Tyr Val Tyr Leu Asn Lys Tyr Leu Gly
            355                 360                 365

Asp Val Asn Asn Val Lys Val Tyr Gly Pro Ala Ala Arg Leu Arg
            370                 375                 380

Pro Thr Asp Val Pro Glu Thr Tyr Tyr Ser Phe Asn Tyr Glu Ala Leu
385                 390                 395                 400

Ala Lys Asn Leu Ser Cys Arg Glu Pro Asn Gln His Phe Arg Pro Tyr
            405                 410                 415

Leu Lys Pro Phe Leu Pro Lys Arg Leu His Phe Ala Lys Ser Asp Arg
            420                 425                 430

Ile Glu Pro Leu Thr Phe Tyr Leu Asp Pro Gln Trp Gln Leu Ala Leu
            435                 440                 445

Asn Pro Ser Glu Arg Lys Tyr Cys Gly Ser Gly Phe His Gly Ser Asp
            450                 455                 460

Asn Leu Phe Ser Asn Met Gln Ala Leu Phe Ile Gly Tyr Gly Pro Ala
465                 470                 475                 480

Phe Lys His Gly Ala Glu Val Asp Ser Phe Glu Asn Ile Glu Val Tyr
            485                 490                 495

Asn Leu Met Cys Asp Leu Leu Gly Leu Ile Pro Ala Pro Asn Asn Gly
            500                 505                 510

Ser His Gly Ser Leu Asn His Leu Leu Lys Pro Ile Tyr Asn Pro
            515                 520                 525

Ser His Pro Lys Glu Glu Gly Phe Leu Ser Gln Cys Pro Ile Lys Ser
            530                 535                 540

Thr Ser Asn Asp Leu Gly Cys Thr Cys Asp Pro Trp Ile Val Pro Ile
545                 550                 555                 560

Lys Asp Phe Glu Lys Gln Leu Asn Leu Thr Thr Glu Asp Val Asp Asp
            565                 570                 575

Ile Tyr His Met Thr Val Pro Tyr Gly Arg Pro Arg Ile Leu Leu Lys
            580                 585                 590
```

```
Gln His Arg Val Cys Leu Leu Gln Gln Gln Phe Leu Thr Gly Tyr
            595                 600                 605

Ser Leu Asp Leu Leu Met Pro Leu Trp Ala Ser Tyr Thr Phe Leu Ser
610                 615                 620

Asn Asp Gln Phe Ser Arg Asp Phe Ser Asn Cys Leu Tyr Gln Asp
625                 630                 635                 640

Leu Arg Ile Pro Leu Ser Pro Val His Lys Cys Ser Tyr Tyr Lys Ser
                645                 650                 655

Asn Ser Lys Leu Ser Tyr Gly Phe Leu Thr Pro Pro Arg Leu Asn Arg
            660                 665                 670

Val Ser Asn His Ile Tyr Ser Glu Ala Leu Leu Thr Ser Asn Ile Val
        675                 680                 685

Pro Met Tyr Gln Ser Phe Gln Val Ile Trp His Tyr Leu His Asp Thr
690                 695                 700

Leu Leu Gln Arg Tyr Ala His Glu Arg Asn Gly Ile Asn Val Val Ser
705                 710                 715                 720

Gly Pro Val Phe Asp Phe Asp Tyr Asp Gly Arg Tyr Asp Ser Leu Glu
                725                 730                 735

Ile Leu Lys Gln Asn Ser Arg Val Ile Arg Ser Gln Glu Ile Leu Ile
            740                 745                 750

Pro Thr His Phe Phe Ile Val Leu Thr Ser Cys Lys Gln Leu Ser Glu
        755                 760                 765

Thr Pro Leu Glu Cys Ser Ala Leu Glu Ser Ser Ala Tyr Ile Leu Pro
770                 775                 780

His Arg Pro Asp Asn Ile Glu Ser Cys Thr His Gly Lys Arg Glu Ser
785                 790                 795                 800

Ser Trp Val Glu Glu Leu Leu Thr Leu His Arg Ala Arg Val Thr Asp
                805                 810                 815

Val Glu Leu Ile Thr Gly Leu Ser Phe Tyr Gln Asp Arg Gln Glu Ser
            820                 825                 830

Val Ser Glu Leu Leu Arg Leu Lys Thr His Leu Pro Ile Phe Ser Gln
        835                 840                 845

Glu Asp
    850

<210> SEQ ID NO 25
<211> LENGTH: 1474
<212> TYPE: PRT
<213> ORGANISM: Artificial Sequence
<220> FEATURE:
<223> OTHER INFORMATION: chemically synthesized

<400> SEQUENCE: 25

Met Thr Ser Lys Phe Leu Leu Val Ser Phe Ile Leu Ala Ala Leu Ser
1               5                   10                  15

Leu Ser Thr Thr Phe Ser Leu Gln Pro Ser Cys Ala Lys Glu Val Lys
            20                  25                  30

Ser Cys Lys Gly Arg Cys Phe Glu Arg Thr Phe Ser Asn Cys Arg Cys
        35                  40                  45

Asp Ala Ala Cys Val Ser Leu Gly Asn Cys Cys Leu Asp Phe Gln Glu
    50                  55                  60

Thr Cys Val Glu Pro Thr His Ile Trp Thr Cys Asn Lys Phe Arg Cys
65                  70                  75                  80

Gly Glu Lys Arg Leu Ser Arg Phe Val Cys Ser Cys Ala Asp Asp Cys
                85                  90                  95
```

Lys Thr His Asn Asp Cys Cys Ile Asn Tyr Ser Ser Val Cys Gln Asp
            100                 105                 110

Lys Lys Ser Trp Val Glu Glu Thr Cys Glu Ser Ile Asp Thr Pro Glu
        115                 120                 125

Cys Pro Ala Glu Phe Glu Ser Pro Pro Thr Leu Leu Phe Ser Leu Asp
130                 135                 140

Gly Phe Arg Ala Glu Tyr Leu His Thr Trp Gly Gly Leu Leu Pro Val
145                 150                 155                 160

Ile Ser Lys Leu Lys Asn Cys Gly Thr Tyr Thr Lys Asn Met Arg Pro
                165                 170                 175

Met Tyr Pro Thr Lys Thr Phe Pro Asn His Tyr Ser Ile Val Thr Gly
        180                 185                 190

Leu Tyr Pro Glu Ser His Gly Ile Ile Asp Asn Lys Met Tyr Asp Pro
        195                 200                 205

Lys Met Asn Ala Ser Phe Ser Leu Lys Ser Lys Glu Lys Phe Asn Pro
210                 215                 220

Leu Trp Tyr Lys Gly Gln Pro Ile Trp Val Thr Ala Asn His Gln Glu
225                 230                 235                 240

Val Lys Ser Gly Thr Tyr Phe Trp Pro Gly Ser Asp Val Glu Ile Asp
                245                 250                 255

Gly Ile Leu Pro Asp Ile Tyr Lys Val Tyr Asn Gly Ser Val Pro Phe
                260                 265                 270

Glu Glu Arg Ile Leu Ala Val Leu Glu Trp Leu Gln Leu Pro Ser His
        275                 280                 285

Glu Arg Pro His Phe Tyr Thr Leu Tyr Leu Glu Pro Asp Ser Ser
290                 295                 300

Gly His Ser His Gly Pro Val Ser Ser Glu Val Ile Lys Ala Leu Gln
305                 310                 315                 320

Lys Val Asp Arg Leu Val Gly Met Leu Met Asp Gly Leu Lys Asp Leu
                325                 330                 335

Gly Leu Asp Lys Cys Leu Asn Leu Ile Leu Ile Ser Asp His Gly Met
                340                 345                 350

Glu Gln Gly Ser Cys Lys Lys Tyr Val Tyr Leu Asn Lys Tyr Leu Gly
            355                 360                 365

Asp Val Asn Asn Val Lys Val Val Tyr Gly Pro Ala Ala Arg Leu Arg
370                 375                 380

Pro Thr Asp Val Pro Glu Thr Tyr Tyr Ser Phe Asn Tyr Glu Ala Leu
385                 390                 395                 400

Ala Lys Asn Leu Ser Cys Arg Glu Pro Asn Gln His Phe Arg Pro Tyr
                405                 410                 415

Leu Lys Pro Phe Leu Pro Lys Arg Leu His Phe Ala Lys Ser Asp Arg
                420                 425                 430

Ile Glu Pro Leu Thr Phe Tyr Leu Asp Pro Gln Trp Gln Leu Ala Leu
            435                 440                 445

Asn Pro Ser Glu Arg Lys Tyr Cys Gly Ser Gly Phe His Gly Ser Asp
        450                 455                 460

Asn Leu Phe Ser Asn Met Gln Ala Leu Phe Ile Gly Tyr Gly Pro Ala
465                 470                 475                 480

Phe Lys His Gly Ala Glu Val Asp Ser Phe Glu Asn Ile Glu Val Tyr
                485                 490                 495

Asn Leu Met Cys Asp Leu Leu Gly Leu Ile Pro Ala Pro Asn Asn Gly
            500                 505                 510

Ser His Gly Ser Leu Asn His Leu Leu Lys Lys Pro Ile Tyr Asn Pro

-continued

```
            515                 520                 525
Ser His Pro Lys Glu Gly Phe Leu Ser Gln Cys Pro Ile Lys Ser
        530                 535                 540

Thr Ser Asn Asp Leu Gly Cys Thr Cys Asp Pro Trp Ile Val Pro Ile
545                 550                 555                 560

Lys Asp Phe Glu Lys Gln Leu Asn Leu Thr Thr Glu Asp Val Asp Asp
                    565                 570                 575

Ile Tyr His Met Thr Val Pro Tyr Gly Arg Pro Arg Ile Leu Leu Lys
            580                 585                 590

Gln His Arg Val Cys Leu Leu Gln Gln Gln Phe Leu Thr Gly Tyr
        595                 600                 605

Ser Leu Asp Leu Leu Met Pro Leu Trp Ala Ser Tyr Thr Phe Leu Ser
    610                 615                 620

Asn Asp Gln Phe Ser Arg Asp Phe Ser Asn Cys Leu Tyr Gln Asp
625                 630                 635                 640

Leu Arg Ile Pro Leu Ser Pro Val His Lys Cys Ser Tyr Tyr Lys Ser
                645                 650                 655

Asn Ser Lys Leu Ser Tyr Gly Phe Leu Thr Pro Pro Arg Leu Asn Arg
            660                 665                 670

Val Ser Asn His Ile Tyr Ser Glu Ala Leu Leu Thr Ser Asn Ile Val
        675                 680                 685

Pro Met Tyr Gln Ser Phe Gln Val Ile Trp His Tyr Leu His Asp Thr
    690                 695                 700

Leu Leu Gln Arg Tyr Ala His Glu Arg Asn Gly Ile Asn Val Val Ser
705                 710                 715                 720

Gly Pro Val Phe Asp Phe Asp Tyr Asp Gly Arg Tyr Asp Ser Leu Glu
                725                 730                 735

Ile Leu Lys Gln Asn Ser Arg Val Ile Arg Ser Gln Glu Ile Leu Ile
            740                 745                 750

Pro Thr His Phe Phe Ile Val Leu Thr Ser Cys Lys Gln Leu Ser Glu
    755                 760                 765

Thr Pro Leu Glu Cys Ser Ala Leu Glu Ser Ser Ala Tyr Ile Leu Pro
770                 775                 780

His Arg Pro Asp Asn Ile Glu Ser Cys Thr His Gly Lys Arg Glu Ser
785                 790                 795                 800

Ser Trp Val Glu Glu Leu Leu Thr Leu His Arg Ala Arg Val Thr Asp
                805                 810                 815

Val Glu Leu Ile Thr Gly Leu Ser Phe Tyr Gln Asp Arg Gln Glu Ser
            820                 825                 830

Val Ser Glu Leu Leu Arg Leu Lys Thr His Leu Pro Ile Phe Ser Gln
        835                 840                 845

Glu Asp Gly Gly Ser Gly Gly Ser Met Lys Trp Val Thr Phe Leu Leu
    850                 855                 860

Leu Leu Phe Val Ser Gly Ser Ala Phe Ser Arg Gly Val Phe Arg Arg
865                 870                 875                 880

Glu Ala His Lys Ser Glu Ile Ala His Arg Tyr Asn Asp Leu Gly Glu
                885                 890                 895

Gln His Phe Lys Gly Leu Val Leu Ile Ala Phe Ser Gln Tyr Leu Gln
            900                 905                 910

Lys Cys Ser Tyr Asp Glu His Ala Lys Leu Val Gln Glu Val Thr Asp
        915                 920                 925

Phe Ala Lys Thr Cys Val Ala Asp Glu Ser Ala Ala Asn Cys Asp Lys
    930                 935                 940
```

```
Ser Leu His Thr Leu Phe Gly Asp Lys Leu Cys Ala Ile Pro Asn Leu
945                 950                 955                 960

Arg Glu Asn Tyr Gly Glu Leu Ala Asp Cys Cys Thr Lys Gln Glu Pro
                965                 970                 975

Glu Arg Asn Glu Cys Phe Leu Gln His Lys Asp Asp Asn Pro Ser Leu
            980                 985                 990

Pro Pro Phe Glu Arg Pro Glu Ala  Glu Ala Met Cys Thr  Ser Phe Lys
        995                 1000                1005

Glu Asn  Pro Thr Thr Phe Met  Gly His Tyr Leu His  Glu Val Ala
    1010                1015                1020

Arg Arg  His Pro Tyr Phe Tyr  Ala Pro Glu Leu Leu  Tyr Tyr Ala
    1025                1030                1035

Glu Gln  Tyr Asn Glu Ile Leu  Thr Gln Cys Cys Ala  Glu Ala Asp
    1040                1045                1050

Lys Glu  Ser Cys Leu Thr Pro  Lys Leu Asp Gly Val  Lys Glu Lys
    1055                1060                1065

Ala Leu  Val Ser Ser Val Arg  Gln Arg Met Lys Cys  Ser Ser Met
    1070                1075                1080

Gln Lys  Phe Gly Glu Arg Ala  Phe Lys Ala Trp Ala  Val Ala Arg
    1085                1090                1095

Leu Ser  Gln Thr Phe Pro Asn  Ala Asp Phe Ala Glu  Ile Thr Lys
    1100                1105                1110

Leu Ala  Thr Asp Leu Thr Lys  Val Asn Lys Glu Cys  Cys His Gly
    1115                1120                1125

Asp Leu  Leu Glu Cys Ala Asp  Asp Arg Ala Glu Leu  Ala Lys Tyr
    1130                1135                1140

Met Cys  Glu Asn Gln Ala Thr  Ile Ser Ser Lys Leu  Gln Thr Cys
    1145                1150                1155

Cys Asp  Lys Pro Leu Leu Lys  Lys Ala His Cys Leu  Ser Glu Val
    1160                1165                1170

Glu His  Asp Thr Met Pro Ala  Asp Leu Pro Ala Ile  Ala Ala Asp
    1175                1180                1185

Phe Val  Glu Asp Gln Glu Val  Cys Lys Asn Tyr Ala  Glu Ala Lys
    1190                1195                1200

Asp Val  Phe Leu Gly Thr Phe  Leu Tyr Glu Tyr Ser  Arg Arg His
    1205                1210                1215

Pro Asp  Tyr Ser Val Ser Leu  Leu Leu Arg Leu Ala  Lys Lys Tyr
    1220                1225                1230

Glu Ala  Thr Leu Glu Lys Cys  Cys Ala Glu Ala Asn  Pro Pro Ala
    1235                1240                1245

Cys Tyr  Gly Thr Val Leu Ala  Glu Phe Gln Pro Leu  Val Glu Glu
    1250                1255                1260

Pro Lys  Asn Leu Val Lys Thr  Asn Cys Asp Leu Tyr  Glu Lys Leu
    1265                1270                1275

Gly Glu  Tyr Gly Phe Gln Asn  Ala Ile Leu Val Arg  Tyr Thr Gln
    1280                1285                1290

Lys Ala  Pro Gln Val Ser Thr  Pro Thr Leu Val Glu  Ala Ala Arg
    1295                1300                1305

Asn Leu  Gly Arg Val Gly Thr  Lys Cys Cys Thr Leu  Pro Glu Asp
    1310                1315                1320

Gln Arg  Leu Pro Cys Val Glu  Asp Tyr Leu Ser Ala  Ile Leu Asn
    1325                1330                1335
```

```
Arg Val Cys Leu Leu His Glu Lys Thr Pro Val Ser Glu His Val
    1340                1345                1350

Thr Lys Cys Cys Ser Gly Ser Leu Val Glu Arg Arg Pro Cys Phe
    1355                1360                1365

Ser Ala Leu Thr Val Asp Glu Thr Tyr Val Pro Lys Glu Phe Lys
    1370                1375                1380

Ala Glu Thr Phe Thr Phe His Ser Asp Ile Cys Thr Leu Pro Glu
    1385                1390                1395

Lys Glu Lys Gln Ile Lys Lys Gln Thr Ala Leu Ala Glu Leu Val
    1400                1405                1410

Lys His Lys Pro Lys Ala Thr Ala Glu Gln Leu Lys Thr Val Met
    1415                1420                1425

Asp Asp Phe Ala Gln Phe Leu Asp Thr Cys Cys Lys Ala Ala Asp
    1430                1435                1440

Lys Asp Thr Cys Phe Ser Thr Glu Gly Pro Asn Leu Val Thr Arg
    1445                1450                1455

Cys Lys Asp Ala Leu Ala Arg Ser Trp Ser His Pro Gln Phe Glu
    1460                1465                1470

Lys

<210> SEQ ID NO 26
<211> LENGTH: 227
<212> TYPE: PRT
<213> ORGANISM: Artificial Sequence
<220> FEATURE:
<223> OTHER INFORMATION: chemically synthesized

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

Pro Gly Lys
225

<210> SEQ ID NO 27
<211> LENGTH: 618
<212> TYPE: PRT
<213> ORGANISM: Artificial Sequence
<220> FEATURE:
<223> OTHER INFORMATION: chemically synthesized

<400> SEQUENCE: 27

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
    50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

His Lys Asp Asp Asn Pro Ser Leu Pro Pro Phe Glu Arg Pro Glu Ala
    130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gln Arg Met Lys Cys
    210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Thr Cys Cys Asp
    290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly

```
                    340                 345                 350
Thr Phe Leu Tyr Glu Tyr Ser Arg Arg His Pro Asp Tyr Ser Val Ser
            355                 360                 365
Leu Leu Leu Arg Leu Ala Lys Lys Tyr Glu Ala Thr Leu Glu Lys Cys
        370                 375                 380
Cys Ala Glu Ala Asn Pro Pro Ala Cys Tyr Gly Thr Val Leu Ala Glu
385                 390                 395                 400
Phe Gln Pro Leu Val Glu Glu Pro Lys Asn Leu Val Lys Thr Asn Cys
                405                 410                 415
Asp Leu Tyr Glu Lys Leu Gly Glu Tyr Gly Phe Gln Asn Ala Ile Leu
            420                 425                 430
Val Arg Tyr Thr Gln Lys Ala Pro Gln Val Ser Thr Pro Thr Leu Val
        435                 440                 445
Glu Ala Ala Arg Asn Leu Gly Arg Val Gly Thr Lys Cys Cys Thr Leu
450                 455                 460
Pro Glu Asp Gln Arg Leu Pro Cys Val Glu Asp Tyr Leu Ser Ala Ile
465                 470                 475                 480
Leu Asn Arg Val Cys Leu Leu His Glu Lys Thr Pro Val Ser Glu His
                485                 490                 495
Val Thr Lys Cys Cys Ser Gly Ser Leu Val Glu Arg Arg Pro Cys Phe
            500                 505                 510
Ser Ala Leu Thr Val Asp Glu Thr Tyr Val Pro Lys Glu Phe Lys Ala
        515                 520                 525
Glu Thr Phe Thr Phe His Ser Asp Ile Cys Thr Leu Pro Glu Lys Glu
    530                 535                 540
Lys Gln Ile Lys Lys Gln Thr Ala Leu Ala Glu Leu Val Lys His Lys
545                 550                 555                 560
Pro Lys Ala Thr Ala Glu Gln Leu Lys Thr Val Met Asp Asp Phe Ala
                565                 570                 575
Gln Phe Leu Asp Thr Cys Cys Lys Ala Ala Asp Lys Asp Thr Cys Phe
            580                 585                 590
Ser Thr Glu Gly Pro Asn Leu Val Thr Arg Cys Lys Asp Ala Leu Ala
        595                 600                 605
Arg Ser Trp Ser His Pro Gln Phe Glu Lys
    610                 615

<210> SEQ ID NO 28
<211> LENGTH: 3
<212> TYPE: PRT
<213> ORGANISM: Artificial Sequence
<220> FEATURE:
<223> OTHER INFORMATION: chemically synthesized

<400> SEQUENCE: 28

Leu Ile Asn
1

<210> SEQ ID NO 29
<211> LENGTH: 6
<212> TYPE: PRT
<213> ORGANISM: Artificial Sequence
<220> FEATURE:
<223> OTHER INFORMATION: chemically synthesized

<400> SEQUENCE: 29

Gly Gly Ser Gly Gly Ser
1               5
```

```
<210> SEQ ID NO 30
<211> LENGTH: 7
<212> TYPE: PRT
<213> ORGANISM: Artificial Sequence
<220> FEATURE:
<223> OTHER INFORMATION: chemically synthesized

<400> SEQUENCE: 30

Arg Ser Gly Ser Gly Gly Ser
1               5
```

COMPOSITIONS FOR TREATING PATHOLOGICAL CALCIFICATION CONDITIONS, AND METHODS USING SAME

CROSS-REFERENCE TO RELATED APPLICATIONS

The present application is a continuation of, and claims priority to, PCT International Application No. PCT/US2016/033236, filed May 19, 2016, which claims priority under 35 U.S.C. § 119(e) to U.S. Provisional Patent Application No. 62/163,500, filed May 19, 2015, all of which applications are incorporated herein by reference in their entireties.

BACKGROUND OF THE INVENTION

Generalized arterial calcification of infancy (GACI) is an ultra-rare neonatal disease characterized by infantile onset of widespread arterial calcifications in large and medium sized vessels resulting in cardiovascular collapse and death in the neonatal period. The disease presents clinically with heart failure, respiratory distress, hypertension, cyanosis, and cardiomegaly. The prognosis is grave, with older reports of a mortality rate of 85% at six months, while recently intensive treatment with bisphosphonates has lowered mortality to 55% at six months. Tempering this apparent progress is the severe skeletal toxicity associated with prolonged use of etridonate in patients with GACI, the observation that the limited available data makes it difficult to determine if bisphosphonate treatment is truly protective or reflects the natural history of the disease in less effected patients, and the ineffectiveness of bisphosphonates to prevent mortality in some patients even when instituted early.

The overall incidence of GACI is rare, with 200 reported cases in the medical literature and a disease frequency of one in 391,000. Although the disease was first described by Bryant and White in 1901, it was not until 2000 that Rutsch and colleagues noted that serum PPi levels and ENPP1 enzymatic activity was significantly impaired in GACI patients. ENPP1 (also known as NPP1 or PC-1) is a member of the ectonucleotide pyrophosphatase/phosphodiesterase (also known as ENPP or NPP) family of enzymes, which are characterized by phosphodiesterase activity, and is a type II extracellular membrane bound glycoprotein located on the mineral-depositing matrix vesicles of osteoblasts and chondrocytes, as well as the vascular surface of cerebral capillaries. ENPP1 catabolizes the degradation of extracellular ATP into AMP and PPi. PPi inhibits ectopic tissue mineralization, presumably by occupying some of the Pi sites on the surface of nascent or growing hydroxyapatite (HA) crystals, thereby creating irregularities that slow or terminate the propagation of crystal growth. Inactivating mutations in ENPP1 account for 75% of GACI patients, and a sizable fraction of the remaining patients result from inactivating mutations in the ATP dependent membrane transporter MRP6, encoded by the abcc6 gene. Mutations in abcc6 have been linked to decreased extracellular concentrations of nucleoside triphosphates, thereby limiting ENPP1's metabolism of ATP into extracellular PPi.

Kidneys are integral to maintenance of normal bone and mineral metabolism, including excretion of phosphate. Patients with kidney failure are unable to appropriately regulate serum mineral balance and tend to retain phosphate that is absorbed from the various dietary components. A high serum level of phosphate is associated with excessive secretion of parathyroid hormone and a tendency to calcification of the soft tissues including the blood vessels.

In patients with kidney failure, excess removal of phosphate and pyrophosphate anions can occur during hemodialysis or peritoneal dialysis. Depletion of these anions from tissues and plasma leads to disorders of bone and mineral metabolism, including osteomalacia and calcification of soft tissues and bone disease. Pyrophosphate deficiency may be a risk factor for deposition of calcium into the small vessels of the skin, causing an inflammatory vasculitis called calciphylaxis that can lead to gangrene of the skin and underlying tissues, resulting in severe, chronic pain. Calciphylaxis may necessitate amputation of the affected limb and is commonly fatal, with no effective treatment for this condition. Ectopic calcification, if left untreated, results in increased morbidity and death. It is important to regulate the amount of pyrophosphate in the system and reduce the occurrence of calciphylaxis in patients.

In 2003, 19.5 million U.S. adults have chronic kidney disease (CKD), and 13.6 million had stage 2-5 CKD, as defined by the National Kidney Foundation Kidney Disease Outcomes Quality Initiative (NKFK/DOQI). Adverse outcomes of chronic kidney disease can often be prevented or delayed through early detection and treatment.

The prevalence of end-stage renal disease (ESRD) is increasing at an alarming rate. In 2000, end stage kidney disease developed in over 90,000 people in the U.S. The population of patients on dialysis therapy or needing transplantation was 380,000 in 2003, and became 651,000 patients in 2010. Care for patients with ESRD already consumes more than $18 billion per year in the U.S., a substantial burden for the health care system.

Calcific uremic arteriolopathy (also known as CUA) is a fatal disease seen in patients with chronic kidney disease (CKD) on dialysis. Calcification of small arteries leads to ischemia of the tissue and skin, infarction and thrombosis, with patient mortality close to 80%. Currently there are 450,000 patients on dialysis in the U.S. who are at risk of acquiring CUA, and there is no FDA approved treatments for the disease. CUA has hallmarks resembling GACI and other disorders of calcification with exhibiting low levels of PPi and high levels of fibroblast growth factor 23 (or FGF23). In ESRD patients requiring dialysis, this calcification process is further accelerated, with an average life-expectancy of 5-6 years.

Pseudoxanthoma elasticum (PXE) is a heritable disorder characterized by mineralization of elastic fibers in skin, arteries and the retina, that result in dermal lesions with associated laxity and loss of elasticity, arterial insufficiency, cardiovascular disease and retinal hemorrhages leading to macular degeneration. Mutations associated with PXE are also located in the abcc6 gene. The skin manifestations are among the most common characteristics of PXE, but the ocular and cardiovascular symptoms are responsible for the morbidity of the disease. Characteristic skin lesions (yellowish papules and plaques and laxity with loss of elasticity, typically seen on the face, neck, axilla, antecubital fossa, popliteal fossa, groin and periumbilical areas) are generally an early sign of PXE and result from an accumulation of abnormal mineralized elastic fibers in the mid-dermis and. They are usually detected during childhood or adolescence and progress slowly and often unpredictably. A PXE diagnosis can be confirmed by a skin biopsy that shows calcification of fragmented elastic fibers in the mid- and lower dermis.

Common cardiovascular complications of PXE are due to the presence of abnormal calcified elastic fibers in the internal elastic lamina of medium-sized arteries. The broad spectrum of phenotypes includes premature atherosclerotic changes, intimal fibroplasia causing angina or intermittent claudication or both, early myocardial infarction and hypertension. Fibrous thickening of the endocardium and atrioventricular valves can also result in restrictive cardiomyopathy. Approximately 10% of PXE patients also develop gastrointestinal bleeding and central nervous system complications (such as stroke and dementia) as a consequence of systemic arterial wall mineralization. In addition, renovascular hypertension and atrial septal aneurysm can be seen in PXE patients.

Conditions in which serum phosphate levels are reduced or elevated are referred to as hypophosphatemia and hyperphosphatemia, respectively. Hypophosphatemia, which often results from renal phosphate wasting, is caused by a number of genetic disorders including X-linked hypophosphatemic rickets (XLH), hereditary hypophosphatemic rickets with hypercalciuria (HHRH), hypophosphatemic bone disease (HBD), and autosomal dominant hypopohsphatemic rickets (ADHR). The exact molecular mechanisms by which proper serum phosphate concentrations are maintained are poorly understood, but it is crucial to maintain serum phosphate levels in order to alleviate symptoms of aforesaid diseases.

There is thus a need in the art for novel compositions and methods for treating diseases and disorders associated with pathological calcification and/or pathological ossification. Such compositions and methods should not undesirably disturb other physiologic processes. The present invention fulfills this need.

BRIEF SUMMARY OF THE INVENTION

The invention provides a compound of formula (I), or a salt or solvate thereof. The invention further provides a method of treating or preventing a disease or disorder associated with pathological calcification or pathological ossification in a subject in need thereof. The invention further provides a method of reducing or preventing cardiac calcifications, arterial calcifications and/or elastic fiber mineralizations in an infant afflicted with at least one disease or disorder selected from the group consisting of GACI and PXE.

In certain embodiments, the compound of formula (I) is PROTEIN-Z-DOMAIN-X-Y (I), wherein in (I): PROTEIN is selected from the group consisting of SEQ ID NO:15, SEQ ID NO:17, SEQ ID NO:19, and SEQ ID NO:24; DOMAIN is selected from the group consisting of a human IgG Fc domain (also referred to as Fc), human serum albumin protein (also referred to as ALB) and fragment thereof; X and Z are independently absent or a polypeptide comprising 1-20 amino acids; and, Y is absent or is a sequence selected from the group consisting of: $(DSS)_n$ (SEQ ID NO:4), $(ESS)_n$ (SEQ ID NO:5), $(RQQ)_n$ (SEQ ID NO:6), $(KR)_n$ (SEQ ID NO:7), $R_m$ (SEQ ID NO:8), DSS-SEEKFLRRIGRFG (SEQ ID NO:9), EEEEEEEPRGDT (SEQ ID NO:10), APWHLSSQYSRT (SEQ ID NO:11), STLPIPHEFSRE (SEQ ID NO:12), VTKHLNQISQSY (SEQ ID NO:13), and $E_m$ (SEQ ID NO:14), wherein m is an integer ranging from 1 to 15, and wherein n is an integer ranging from 1 to 10.

In certain embodiments, DOMAIN is a Fc or fragment thereof. In other embodiments, DOMAIN is an ALB or fragment thereof.

In certain embodiments, Y is absent and the compound lacks a negatively-charged bone-targeting sequence.

In certain embodiments, the PROTEIN has a mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, the nuclease domain of the PROTEIN or mutant thereof is absent. In yet other embodiments, the nuclease domain from about residue 524 to about residue 885 relative to SEQ ID NO:1 is absent in the PROTEIN or mutant thereof. In yet other embodiments, a segment of the extracellular region of NNP2 containing a furin or signal peptide cleavage site is, or is not, substituted into the PROTEIN or mutant thereof.

In certain embodiments, DOMAIN is a Fc or fragment thereof, and wherein PROTEIN-Z-DOMAIN comprises (SEQ ID NO:15)-Z-(Fc or fragment thereof), (SEQ ID NO:17)-Z-(Fc or fragment thereof), (SEQ ID NO:19)-Z-(Fc or fragment thereof), (SEQ ID NO:24)-Z-(Fc or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, PROTEIN-Z-DOMAIN comprises SEQ ID NO:16, SEQ ID NO:18, SEQ ID NO:20, (SEQ ID NO:24)-Z-(SEQ ID NO:26), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, DOMAIN is an ALB or fragment thereof, and wherein PROTEIN-Z-DOMAIN comprises (SEQ ID NO:15)-Z-(ALB or fragment thereof), (SEQ ID NO:17)-Z-(ALB or fragment thereof), (SEQ ID NO:19)-Z-(ALB or fragment thereof), (SEQ ID NO:24)-Z-(ALB or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, PROTEIN-Z-DOMAIN comprises SEQ ID NO:21, (SEQ ID N:17)-Z-(SEQ ID NO:27), SEQ ID NO:22, SEQ ID NO:25, or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, the compound has a $k_{cat}$ value greater than or equal to about 3.4 ($\pm 0.4$) $s^{-1}$ enzyme$^{-1}$, wherein the $k_{cat}$ is determined by measuring the compound's ATP hydrolysis rate.

In certain embodiments, the compound has a $K_M$ value less than or equal to about 2 µM, wherein the $K_M$ is determined by measuring the compound's ATP hydrolysis rate.

In certain embodiments, the NPP1 polypeptide is a cleavage product of a precursor NPP1 polypeptide comprising an ecto-nucleotide pyrophosphate/phosphodiesterase-2 (NPP2) transmembrane domain.

In certain embodiments, the NPP2 transmembrane domain is residues 12-30 of NCBI accession no. NP_001124335 (SEQ ID NO:2), which corresponds to SEQ ID NO:23.

In certain embodiments, the method comprises administering to the subject a therapeutically effective amount of at least one compound of the invention.

In certain embodiments, the disease comprises at least one selected from the group consisting of Generalized Arterial Calcification of Infancy (GACI), Idiopathic Infantile Arterial Calcification (IIAC), Ossification of the Posterior Longitudinal Ligament (OPLL), hypophosphatemic rickets, osteoarthritis, and calcification of atherosclerotic plaques.

In certain embodiments, the disease comprises at least one selected from the group consisting of PXE, hereditary and non-hereditary forms of osteoarthritis, ankylosing spondylitis, hardening of the arteries occurring with aging, calciphylaxis resulting from end stage renal disease and progeria.

In certain embodiments, Y is absent and the compound lacks a negatively-charged bone-targeting sequence.

In certain embodiments, the method comprises administering to the infant a therapeutically effective amount of a given polypeptide comprising an ecto-nucleotide pyrophosphate/phosphodiesterase-1 (NPP1) polypeptide and an IgG Fc domain, wherein the given polypeptide lacks a polyaspartic acid domain, whereby the administering of the given polypeptide increases extracellular pyrophosphate (PPi) concentrations in the infant.

In certain embodiments, the method comprises administering to the infant a therapeutically effective amount of a given polypeptide comprising an ecto-nucleotide pyrophosphate/phosphodiesterase-1 (NPP1) polypeptide and an ALB, wherein the given polypeptide lacks a polyaspartic acid domain, whereby the administering of the given polypeptide increases extracellular pyrophosphate (PPi) concentrations in the infant.

In certain embodiments, the administering is at least one selected from the group consisting of inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical. In other embodiments, the administering is subcutaneous.

In certain embodiments, the administering restores the infant's extracellular pyrophosphate concentrations to a level within the range found in an infant not afflicted with GACI and/or PXE.

In certain embodiments, the infant presents and/or is diagnosed with "failure to thrive" prior to the administering.

BRIEF DESCRIPTION OF THE DRAWINGS

The following detailed description of illustrative embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 1A-1G comprise a set of images and graphs illustrating a natural history study. FIG. 1A: Average daily weights of ENPP1-asj/asj and ENPP1-WT sibling pairs on acceleration diet. Daily weights of ENPP1-WT (Cyan squares) and ENPP1-asj/asj mice (Green circles) on the acceleration diet over a 70 day period. A failure to thrive point is noted in the ENPP1-asj/asj cohort at day 26, when the weights diverge from ENPP1-WT. Death events are marked with red arrows. FIG. 1B: Survival Curves, Natural History Study. Mean survival of ENPP1-asj/asj was 58 days. No deaths were observed in the ENPP1-WT cohort. FIG. 1C: Representative Micro-CT and histology, Natural History Study. Some asj/asj animals displayed dramatic calcifications in heart and aorta visible on E). Aortas of ENPP1-asj/asj mouse all possessed near circumferential calcifications that were pervasive in the vascular walls, as illustrated by Alzarian red staining of the aortas. FIG. 1F: Histology of asj/asj mice, Left Ventricle (40×). Extensive calcifications surrounded by scar tissue revealing the presence of repeated, old, healed myocardial infarctions. FIG. 1G: Histology of asj/asj mice, Septum (100×). More typically, the asj mice displayed small foci of calcifications with surrounding scar tissue as seen here in the myocardial septum, also diagnostic of previous myocardial infarctions.

FIGS. 2A-2E comprise a set of images and graphs illustrating a metabolic pathway, as well as design, stability, and kinetic properties of a therapeutic protein of the invention. FIG. 2A: Schematic of the metabolic pathway of purinergic metabolism related to ectopic calcification. ENPP1 converts extracellular ATP into AMP and PPi, TNAP converts PPi into Pi, and CD73 converts AMP into adenosine and Pi. The abcc6 gene encodes MRP6, a membrane transporter that increases the extracellular concentration of ATP. Loss of function mutations in TNAP result in familial hypophosphatasia. Loss of function mutations in ENPP1 result in GACI, loss of function mutations in MRP6 result in PXE, and loss of function mutations in CD73 results in a disease of arterial and joint calcification termed 'ACDC'. FIG. 2B: Design of ENPP1 protein therapeutic. To produce a soluble recombinant protein, a segment of the extracellular region of NPP2 containing a furin cleavage site was substituted into ENPP1 as previously described, and the protein was C-terminally fused with the Fc domain of human immunoglobulin 1 (IgG1). FIG. 2C: Stability of ENPP1 therapeutic. ENPP1-Fc Ap3A activity was seen to be stable to freeze-thaw cycle in PBS following storage at −80° C. FIGS. 2D-2E: Steady state kinetics of hENPP1-Fc. FIG. 2D: Time courses of AMP formation measured by HPLC analysis after addition of 10 nM hNPP1-Fc to (from bottom to top) 1.0, 2.0, 7.8, 125 and 250 µM ATP. The smooth curves though data are fits obtained by non-linear kinetic time course analysis. The insert shows the lower [ATP] time courses in Panel A, (from bottom to top) 1.0, 2.0, 7.8 µM ATP. The time course of 1.0 µM ATP shows the ATP was depleted completely after 1 min and therefore the rate was not able to be determined. FIG. 2E: ATP concentration dependent initial ATP hydrolysis rate per enzyme. The initial rates after 7.8 µM are essentially the same with $k_{cat}$ (the average)=3.4 (±0.4) $s^{-1}$ enzyme$^{-1}$. The initial rate at 2.0 µM ATP concentration is about a half of $k_{cat}$ value, and therefore $K_M$~2 µM is estimated for ATP hydrolysis by hNPP1-Fc protein.

FIGS. 3A-3D comprise a set of images and graphs illustrating a proof of concept study. FIG. 3A: Daily animal weights. Average daily weights of ENPP1-WT and ENPP1-asj/asj sibling pairs dosed with vehicle (daily PBS injections supplemented with weekly GK 1.5) compared to ENPP1-asj/asj sibling pairs dosed with daily with mouse ENPP1-Fc (mENPPI-Fc)@500 au/Kg qD in PBS and weekly GK1.5 immunosuppression. Dosing and weighing commenced on day 14. Deaths in the ENPP1-asj/asj+vehicle cohort are denoted by red arrows on the day of death. No deaths were noted in the ENPP1-WT+vehicle or ENPP1-asj/asj+ENPP1-Fc cohort. FIG. 3B: Survival Curves, Proof of Concept Study. FIG. 3C: Left ventricle histology, (40×, H&E), untreated asj/asj mouse displaying large focus of calcifications and micro-infarctions in the free wall. FIG. 3D: Left ventricle histology, (40×, H&E), treated asj/asj mouse. None of the treated ENPP1-asj mice displayed abnormal Left Ventricular Histology.

FIGS. 4A-4G comprise a set of images illustrating representative histology and a proof of concept study. FIGS. 4A-4B: Aorta (40×, alzarian red). Untreated ENPP1-asj mice (FIG. 4A) displayed nearly circumferential aortic calcifications, while treated ENPP1-asj mice (FIG. 4B) did not. FIG. 4C: Untreated ENPP1-asj/asj mice, Right Ventricle (40×, H&E). Two untreated ENPP1-asj mice had large, confluent, myocardial infarctions in the free wall of the Right Ventricle. FIG. 4D: Treated ENPP1-asj/asj mice, Right Ventricle (40×, H&E). All treated ENPP1-asj mice displayed normal Right. ventricle myocardium. FIG. 4E: Untreated ENPP1-asj/asj mice, Coronary Arteries (100×, H&E). All untreated ENPP1-asj/asj mice had coronary calcifications, with most displaying circumferential calcifications in coronary arteries surrounded by scar tissue, diagnostic of ischemia and myocardial infarction. FIG. 4F: Untreated ENPP1-asj/asj mice, Myocardial Septum (100×, H&E). Nearly all animals (77%) displayed intracardiac calcifications surrounded by scar tissue, as demonstrated in this animal in the myocardial septum. FIG. 4G: Phenotypic comparison, treated and untreated ENPP1-asj/asj mice. There is a dramatic size difference in the treated and untreated animals, and a marked difference in the mobility and health of the animals, best seen in the movie submitted in the supplemental data.

FIG. 5A: Postmortem high-resolution micro-CT scans revealed extensive calcifications in untreated ENPP1-asj/asj mice in the hearts, coronary arteries, and ascending and descending aortas, but absolutely no calcifications in these organs in the treated ENPP1-asj/asj cohort or in ENPP1-WT mice. FIG. 5B: Plasma [PPi] in ENPP1-WT and treated and untreated ENPP1-asj/asj animals revealed that treatment with ENPP1-FC increased [PPi] in ENPP1-asj/asj mice above WT levels, and well above the nearly undetectable levels present in untreated ENPP1-asj/asj mice. FIGS. 5C-5D: Percent uptake of injected $^{99m}$PYP in heads of WT and asj/asj animals. The % uptake of $^{99m}$PYP in heads of animals in the natural history study were recorded weekly in the WT and asj/asj animals on the acceleration diet, demonstrating that $^{99m}$PYP uptake remains nearly constant over an 80 day period following birth, but differs markedly between the two experimental groups. FIG. 5D: In the natural history study, the average $^{99m}$PYP uptake in heads of WT animals was around 15% of injected dose over the 80 day period, while the PYP uptake in asj/asj animals was around 20% (p<0.001, students 2-tailed T-test). FIGS. 5E-5F: Percent $^{99m}$PYP uptake of injected dose in the heads of WT, and treated and untreated asj/asj mice. $^{99m}$PYP uptake was recorded in the middle of the study (day 30-35, (FIG. 5e)) and at the end of the study (day 50-65, FIG. 5F) in the experimental groups. WT and treated asj/asj animals had percent uptake in the skulls around 15%, while the untreated ENPP1-asj/asj cohort was at or above 20%. The difference between treated and untreated ENPP1-asj mice was statistically significant (p<0.001, students 2-tailed T-test), while the difference between WT and treated ENPP1-asj mice was not.

DETAILED DESCRIPTION OF THE INVENTION

Figure 1B:
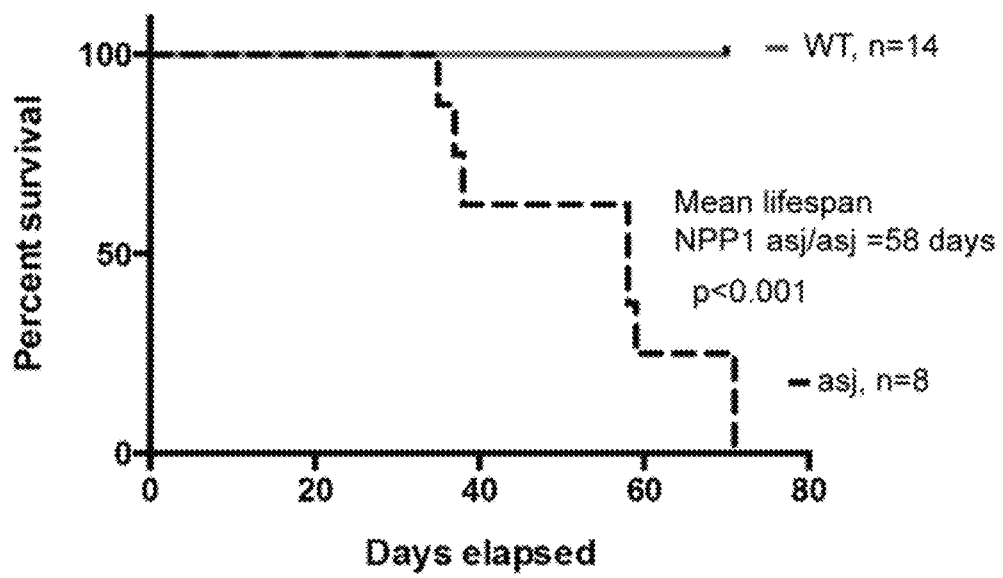
Figure 1C:
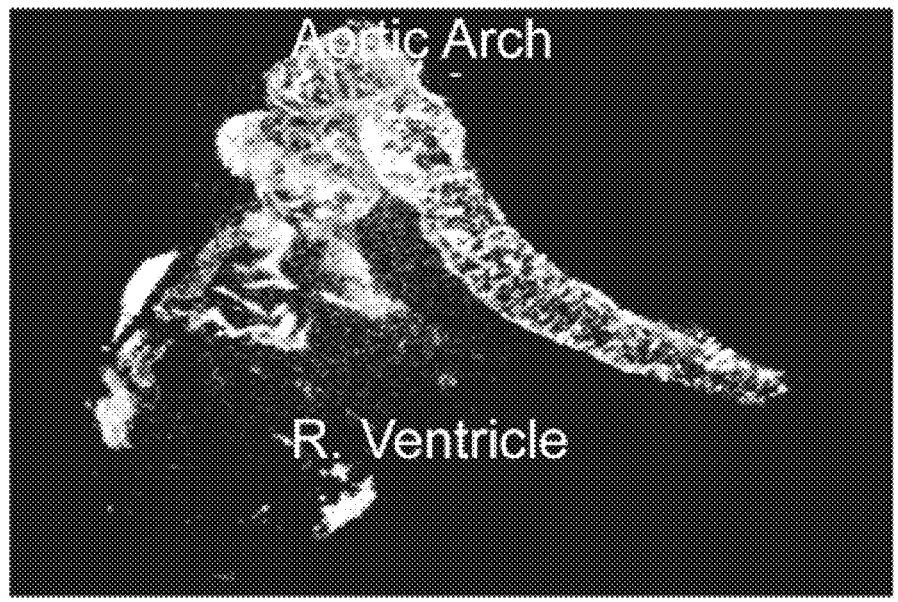

The present invention relates to the discovery that certain NPP1-containing polypeptides, mutants, or mutant fragments thereof, are useful for the treatment of diseases and disorders involving plasma pyrophosphate imbalance, pathological calcification and/or pathological ossification. Diseases and disorders involving pathological calcification and/or pathological ossification treatable by the compositions and methods of the invention, include, but are not limited to Generalized Arterial Calcification of Infancy (GACI), Chronic Kidney Disease (CKD), End Stage Renal Disease (ESRD), Idiopathic Infantile Arterial Calcification (IIAC), Ossification of the Posterior Longitudinal Ligament (OPLL), hypophosphatemic rickets, calcification of atherosclerotic plaques, Pseudoxanthoma elasticum (PXE), hereditary and non-hereditary forms of osteoarthritis, ankylosing spondylitis, hardening of the arteries occurring with aging, calciphylaxis (such as resulting from end stage renal disease) and progeria.

Such diseases are a result of myriad causes: some are genetic mutations and some are complication as a result of diabetes, heart failure or extensive dialysis. Yet, in certain embodiments, they share in common the symptom of plasma pyrophosphate imbalance and/or extensive calcification.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, illustrative methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, the term "ALB" refers to a human serum albumin protein.

A disease or disorder is "alleviated" if the severity of a symptom of the disease or disorder, the frequency with which such a symptom is experienced by a patient, or both, is reduced.

As used herein the terms "alteration," "defect," "variation" or "mutation" refer to a mutation in a gene in a cell that affects the function, activity, expression (transcription or translation) or conformation of the polypeptide it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amino acid sequence variant" refers to polypeptides having amino acid sequences that differ to some extent from a native sequence polypeptide. Ordinarily, amino acid sequence variants possess at least about 70% homology, at least about 80% homology, at least about 90% homology, or at least about 95% homology to the native polypeptide. The amino acid sequence variants possess substitutions, deletions, and/or insertions at certain positions within the amino acid sequence of the native amino acid sequence.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and a humanized antibodies (Harlow, et al., 1999, Using Antibodies: A Laboratory Manual, Cold Spring Harbor Laboratory Press, NY; Harlow, et al., 1989, Antibodies: A Laboratory Manual, Cold Spring Harbor, N.Y.; Houston, et al., 1988, Proc. Natl. Acad. Sci. USA 85:5879-5883; Bird, et al., 1988, Science 242:423-426).

As used herein, the term "Ap3P" refers to adenosine-(5')-triphospho-(5')-adenosine or a salt thereof.

As used herein, the terms "child" and "infant" are used interchangeably.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties. Specific examples of binding domains include, but are not limited to, DNA binding domains and ATP binding domains.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "Fc" refers to a human IgG Fc domain.

As used herein, the term "failure to thrive" refers to a child or infant whose current weight or rate of weight gain is lower than that of other children of similar age and gender. The situation where a child or infant "fails to thrive" can be identified by consultation with a medical specialist, and/or comparison of the child's or infant's weight or weight gain rate with known average age-specific weight or weight gain rate data.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein, an "immunoassay" refers to any binding assay that uses an antibody capable of binding specifically to a target molecule to detect and quantify the target molecule.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Instructional material," as that term is used herein, includes a publication, a recording, a diagram, or any other medium of expression which can be used to communicate the usefulness of the nucleic acid, peptide, and/or compound of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the invention or be shipped together with a container that contains the nucleic acid, polypeptide, and/or compound. Alternatively, the instructional material may be shipped separately from the container with the intention that the recipient uses the instructional material and the compound cooperatively.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "NPP" or "ENPP" refers to ectonucleotide pyrophosphatase/phosphodiesterase.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. See Albert L. Lehninger, Principles of Biochemistry, at 793-800 (Worth Pub. 1982) which is herein incorporated in its entirety for all purposes. Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, in certain embodiments at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably herein. It is understood that when a nucleotide sequence is represented herein by a DNA sequence (e.g., A, T, G, and C), this also includes the corresponding RNA sequence (e.g., A, U, G, C) in which "U" replaces "T."

As used herein, the term "patient," "individual" or "subject" refers to a human or a non-human mammal. Non-human mammals include, for example, livestock and pets, such as ovine, bovine, porcine, canine, feline and murine mammals. In certain embodiments, the patient, individual or subject is human.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "pharmaceutical composition" or "composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, amino acids are represented by the full name thereof, by the three letter code corresponding thereto, or by the one-letter code corresponding thereto, as indicated below: Aspartic Acid (Asp/D); Glutamic Acid (Glu/E); Lysine (Lys/K); Arginine (Arg/R); Histidine (His/H); Tyrosine (Tyr/Y); Cysteine (Cys/C); Asparagine (Asn/N); Glutamine (Gln/Q); Serine (Ser/S); Threonine (Thr/T); Glycine (Gly/G); Alanine (Ala/A); Valine (Val/V); Leucine (Leu/L); Isoleucine (Ile/I); Methionine (Met/M); Proline (Pro/P); Phenylalanine (Phe/F); Tryptophan (Trp/W).

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, "substantially purified" refers to being essentially free of other components. For example, a substantially purified polypeptide is a polypeptide which has been separated from other components with which it is normally associated in its naturally occurring state.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. Naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

ENPP1 is the primary source of extracellular PPi in the body. Despite the multiple genetic etiologies and multifactorial nature of the expression, progression, and severity of GACI, the present results demonstrate that disruption of NPP1's extracellular purinergic metabolism accounts for the pathologic sequela and mortality associated with GACI, and enzyme replacement therapy with ENPP1 is a tractable therapeutic approach. This was demonstrated using the ENPP1-asj mouse model of GACI on the 'acceleration diet'.

Diseases of ectopic tissue calcification range from the ultra-rare diseases, such as GACI, to nearly ubiquitous maladies in the aging population such as hardening of the arteries and osteoarthritis. The genetic etiology of human GACI suggests that the lethal arterial calcifications result from impairment of extracellular purinergic metabolism, either through loss of function mutations in ENPP1 or upstream reductions in nucleotide triphosphates metabolized by ENPP1 into extracellular PPi. As demonstrated herein, subcutaneous supplementation with untargeted ENPP1 or untargeted ENPP1-Fc increases extracellular PPi concentrations sufficiently to eliminate the mortality, as well as the cardiac and arterial calcifications in animal models of GACI. These results indicate that untargeted enzyme replacement therapy can be efficacious in GACI and other diseases resulting in uncontrolled vascular calcification.

The present results are surprising in light of previous studies treating hereditary hypophosphatasia (HPP), which claimed the necessity of a bone-targeting motif for efficacy. HPP is a rickets-like disease of reduced/absent of bone mineralization, and treatment with recombinant TNAP invoked the necessity of bone targeting to achieve a clinical effect (Millan, et al., 2008, J. Bone Mineral Res. 23:777-787; Whyte, et al., 2012, New Engl. J. Med. 366:904-913). Clinical trials attempting to treat HPP with serum enriched with untargeted TNAP failed (Whyte, et al., 1982, J. Pediatrics 101:379-386; Whyte, et al., 1984, J. Pediatrics 105: 926-933; Weninger, et al., 1989, Acta Paediatrica Scandinavica Suppl. 360:154-160). Further, the literature at the time of the invention indicated that untargeted NPP1 showed no efficacy with in vitro calcification assays (WO 2012/125182 to Quinn, et al., such as for example FIG. 23 therein), thus indicating that bone targeting was essential for the biological activity of an NPP1 containing biologic in vivo. However, in certain embodiments, the present results indicate that bone-targeting is not necessary for therapeutic efficacy.

The arterial calcifications of GACI may be accompanied by extravascular calcifications in the skin and retina that typify a second rare disease, PXE. PXE is a closely related to GACI, but instead results in ectopic tissue mineralization of elastic fibers affecting the skin, eyes, and cardiovascular system. PXE has a later onset, slower progression, and is relatively more common than GACI, with an incidence of 1/25,000 to 1/75,000. The clinical manifestations begin in the skin with the development of small yellowish papules that coalesce into larger plaques of leathery skin followed by angioid streaks in the eye leading to bleeding, scarring, neovascularization, progressive loss of visual acuity and blindness. The cardiovascular system may also be affected by progressive mineralization of the medium sized arterial blood vessels, resulting in hypertension, claudication, occasional bleeding of the intestinal arteries, and (rarely) premature myocardial infarction. The genetic basis of PXE is loss of function mutations in the abcc6 gene, resulting in impaired function of the MRP6 protein, which reduces extracellular nucleotriphosphate (NTP) concentrations in vitro and in vivo. This reduces ENPP1 substrate concentrations and thereby limits extracellular production of PPi.

The NPP1-asj mouse model of GACI possesses both the genetic etiology and the pathologic features of human GACI, but the mice also develop periarticular calcifications not characteristic of GACI but reminiscent of human diseases of unregulated periarticular calcification such as osteoarthritis and ossification of the posterior longitudinal ligament (OPLL). Mice possessing a missense mutation in ENPP1 (V246D) were initially described as 'asj' mice for 'associated with stiffened joints', reflecting the development of progressive periarticular calcifications in the forepaws of the mice. ENPP1 mutations in mice are used to model paraspinal calcifications in ttw/ttw mice to provide insight into OPLL, but identification of ENPP1 mutations in GACI led to a reappraisal of the presence of vascular calcifications in these animals and Uitto and coworkers noted that NPP1-asj mice, when fed a special diet high in $Ca^{+2}$ and low in $Mg^{+2}$, recapitulated many of the essential features of human GACI. ENPP1 protein levels correlate inversely with the severity of cartilage calcification and osteoarthritis in humans, and ENPP1 genetic variants account for a substantial fraction of hand osteoarthritis in patient populations predisposed to hereditary forms of the disease. In certain embodiments, ENPP1 enzyme replacement therapy is a viable treatment strategy for forms of osteoarthritis resulting from ENPP1 deficiency and/or a reduction of extracellular PPi concentration. Such conditions include, but are not limited to, PXE, hereditary and non-hereditary forms of osteoarthritis, ankylosing spondylitis, hardening of the arteries occurring with aging, and calciphylaxis resulting from end stage renal disease.

Compositions

In certain embodiments, the compositions of the invention comprises at least one compound of formula (I), or a solvate or salt (such as a pharmaceutically acceptable salt) thereof:

PROTEIN-Z-DOMAIN-X-Y (I), wherein in (I)

PROTEIN is at least one selected from the group consisting of NPP121 (SEQ ID NO:15), NPP71 (SEQ ID NO:17), NPP71 lacking NPP1 N-terminus GLK (SEQ ID NO:19), and NPP51 (SEQ ID NO:24);

DOMAIN is at least one selected from the group consisting of a human IgG Fc domain (Fc), human serum albumin protein (ALB) and a fragment thereof;

X and Z are independently absent or a polypeptide comprising 1-20 amino acids; and, Y is absent or a sequence selected from the group consisting of: $(DSS)_n$(SEQ ID NO:4), $(ESS)_n$ (SEQ ID NO:5), $(RQQ)_n$ (SEQ ID NO:6), $(KR)_n$ (SEQ ID NO:7), $R_m$ (SEQ ID NO:8), DSSSEEKFLRRIGRFG (SEQ ID NO:9), EEEEEEEPRGDT (SEQ ID NO:10), APWHLSSQYSRT (SEQ ID NO:11), STLPIPHEFSRE (SEQ ID NO:12), VTKHLNQISQSY (SEQ ID NO:13), and $E_m$ (SEQ ID NO:14) wherein m is an integer ranging from 1 to 15, and wherein n is an integer ranging from 1 to 10.

In certain embodiments, the compositions of the invention comprises at least one compound of formula (II), or a pharmaceutical salt thereof:

PROTEIN-Z-DOMAIN-X-Y (II), wherein in (II)

PROTEIN is at least one selected from the group consisting of NPP121 (SEQ ID NO:15), NPP71 (SEQ ID NO:17), NPP71 lacking NPP1 N-terminus GLK (SEQ ID NO:19), and NPP51 (SEQ ID NO:24);

DOMAIN is at least one selected from the group consisting of a human IgG Fc domain (Fc), human serum albumin protein (ALB) and a fragment thereof;

X and Z are independently absent or a polypeptide comprising 1-20 amino acids; and, Y is a sequence selected from the group consisting of: $(DSS)_n$(SEQ ID NO:4), $(ESS)_n$ (SEQ ID NO:5), $(RQQ)_n$ (SEQ ID NO:6), $(KR)_n$ (SEQ ID NO:7), $R_m$ (SEQ ID NO:8), DSSSEEKFLRRIGRFG (SEQ ID NO:9), EEEEEEEPRGDT (SEQ ID NO:10), APWHLSSQYSRT (SEQ ID NO:11), STLPIPHEFSRE (SEQ ID NO:12), VTKHLNQISQSY (SEQ ID NO:13), and $E_m$ (SEQ ID NO:14), wherein m is an integer ranging from 1 to 15, and wherein n is an integer ranging from 1 to 10.

In certain embodiments, DOMAIN comprises a human IgG Fc domain or fragment thereof. In other embodiments, DOMAIN consists essentially of a human IgG Fc domain or fragment thereof. In yet other embodiments, DOMAIN consists of a human IgG Fc domain or fragment thereof.

In certain embodiments, DOMAIN comprises a human serum albumin protein or a fragment thereof. In other embodiments, DOMAIN consists essentially of a human serum albumin protein or a fragment thereof. In yet other embodiments, DOMAIN consists of a human serum albumin protein or a fragment thereof.

In certain embodiments, Y is a negatively-charged bone-targeting sequence. In certain embodiments, Y is absent. In certain embodiments, Y is absent and the compound of formula (I) or (II) lacks a negatively-charged bone-targeting sequence. In yet other embodiments, a polyaspartic acid domain and SEQ ID NOs:4-14 are non-limiting examples of a negatively-charged bone-targeting sequence.

In certain embodiments, the PROTEIN has a mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, the PROTEIN or mutant thereof is truncated to remove the nuclease domain. In yet other embodiments, the PROTEIN or mutant thereof is truncated to remove the nuclease domain from about residue 524 to about residue 885 relative to SEQ ID NO:1, leaving only the catalytic domain from about residue 186 to about residue 586 relative to SEQ ID NO:1, which serves to preserve the catalytic activity of the protein.

In certain embodiments, in (I) or (II) PROTEIN-Z-DOMAIN comprises (SEQ ID NO:15)-Z-(Fc or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, Z is a tripeptide. In yet other embodiments, Z is L I N. In yet other embodiments, in (I) or (II) PROTEIN-Z-DOMAIN comprises SEQ ID NO:16, or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, in (I) or (II) PROTEIN-Z-DOMAIN comprises (SEQ ID NO:17)-Z-(Fc or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, Z is a tripeptide. In yet other embodiments, Z is L I N. In yet other embodiments, in (I) or (II) PROTEIN-Z-DOMAIN comprises SEQ ID NO:18, or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, in (I) or (II) PROTEIN-Z-DOMAIN comprises (SEQ ID NO:19)-Z-(Fc or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, Z is a tripeptide. In yet other embodiments, Z is L I N. In yet other embodiments, in (I) or (II) PROTEIN-Z-DOMAIN comprises SEQ ID NO:20, or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, in (I) or (II) PROTEIN-Z-DOMAIN comprises (SEQ ID NO:24)-Z-(Fc or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, Z is a tripeptide. In yet other embodiments, Z is L I N. In yet other embodiments, in (I) or (II) PROTEIN-Z-DOMAIN comprises (SEQ ID NO:24)-Z-(SEQ ID NO:26), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, in (I) or (II) PROTEIN-Z-DOMAIN comprises (SEQ ID NO:15)-Z-(ALB or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, Z is a tripeptide. In yet other embodiments, Z is one selected from the group consisting of SEQ ID NOs:28-30. In yet other embodiments, in (I) or (II) PROTEIN-Z-DOMAIN comprises SEQ ID NO:21, or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, in (I) or (II) PROTEIN-Z-DOMAIN comprises (SEQ ID NO:17)-Z-(ALB or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, Z is a tripeptide. In yet other embodiments, Z is one selected from the group consisting of SEQ ID NOs:28-30. In yet other embodiments, in (I) or (II) PROTEIN-Z-DOMAIN comprises (SEQ ID NO:17)-Z-(SEQ ID NO:27), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1, wherein Z is one selected from the group consisting of SEQ ID NOs:28-30.

In certain embodiments, in (I) or (II) PROTEIN-Z-DOMAIN comprises (SEQ ID NO:19)-Z-(ALB or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, Z is a tripeptide. In yet other embodiments, Z is one selected from the group consisting of SEQ ID NOs:28-30. In yet other embodiments, in (I) or (II) PROTEIN-Z-DOMAIN comprises SEQ ID NO:22, or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, in (I) or (II) PROTEIN-Z-DOMAIN comprises (SEQ ID NO:24)-Z-(ALB or fragment thereof), or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1. In other embodiments, Z is a tripeptide. In yet other embodiments, Z is one selected from the group consisting of SEQ ID NOs:28-30. In yet other embodiments, in (I) or (II) PROTEIN-Z-DOMAIN comprises SEQ ID NO:25, or a mutant thereof comprising at least one mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In certain embodiments, X and Z are independently absent or a polypeptide comprising 1-18 amino acids. In other embodiments, X and Z are independently absent or a polypeptide comprising 1-16 amino acids. In yet other embodiments, X and Z are independently absent or a polypeptide comprising 1-14 amino acids. In yet other embodiments, X and Z are independently absent or a polypeptide comprising 1-12 amino acids. In yet other embodiments, X and Z are independently absent or a polypeptide comprising 1-10 amino acids. In yet other embodiments, X and Z are independently absent or a polypeptide comprising 1-8 amino acids. In yet other embodiments, X and Z are independently absent or a polypeptide comprising 1-6 amino acids. In yet other embodiments, X and Z are independently absent or a polypeptide comprising 1-5 amino acids. In yet other embodiments, X and Z are independently absent or a polypeptide comprising 1-4 amino acids. In yet other embodiments, X and Z are independently absent or a polypeptide comprising 1-3 amino acids. In yet other embodiments, X and Z are independently absent or a polypeptide comprising 1-2 amino acids. In yet other embodiments, X and Z are independently absent or a single amino acid.

In certain embodiments, m is 1. In other embodiments, m is 2. In yet other embodiments, m is 3. In yet other embodiments, m is 4. In yet other embodiments, m is 5. In yet other embodiments, m is 6. In yet other embodiments, m is 7. In yet other embodiments, m is 8. In yet other embodiments, m is 9. In yet other embodiments, m is 10. In yet other embodiments, m is 11. In yet other embodiments, m is 12. In yet other embodiments, m is 13. In yet other embodiments, m is 14. In yet other embodiments, m is 15. In yet other embodiments, each occurrence of m is independently selected from the group consisting of an integer ranging from 1 to 15, from 2 to 15, from 3 to 15, from 4 to 15, from 5 to 15, from 6 to 15, from 7 to 15, from 8 to 15, from 9 to 15, from 10 to 15, from 11 to 15, from 12 to 15, from 13 to 15, from 14 to 15, from 1 to 14, from 2 to 14, from 3 to 14, from 4 to 14, from 5 to 14, from 6 to 14, from 7 to 14, from 8 to 14, from 9 to 14, from 10 to 14, from 11 to 14, from 12 to 14, from 13 to 14, from 1 to 13, from 2 to 13, from 3 to 13, from 4 to 13, from 5 to 13, from 6 to 13, from 7 to 13, from 8 to 13, from 9 to 13, from 10 to 13, from 11 to 13, from 12 to 13, from 1 to 12, from 2 to 12, from 3 to 12, from 4 to 12, from 5 to 12, from 6 to 12, from 7 to 12, from 8 to 12, from 9 to 12, from 10 to 12, from 11 to 12, from 1 to 11, from 2 to 11, from 3 to 11, from 4 to 11, from 5 to 11, from 6 to 11, from 7 to 11, from 8 to 11, from 9 to 11, from 10 to 11, from 1 to 10, from 2 to 10, from 3 to 10, from 4 to 10, from 5 to 10, from 6 to 10, from 7 to 10, from 8 to 10, from 9 to 10, from 1 to 9, from 2 to 9, from 3 to 9, from 4 to 9, from 5 to 9, from 6 to 9, from 7 to 9, from 8 to 9, from 1 to 8, from 2 to 8, from 3 to 8, from 4 to 8, from 5 to 8, from 6 to 8, from 7 to 8, from 1 to 7, from 2 to 7, from 3 to 7, from 4 to 7, from 5 to 7, from 6 to 7, from 1 to 6, from 2 to 6, from 3 to 6, from 4 to 6, from 5 to 6, from 1 to 5, from 2 to 5, from 3 to 5, from 4 to 5, from 1 to 4, from 2 to 4, from 3 to 4, from 1 to 3, from 2 to 3, and from 1 to 2.

In certain embodiments, n is 1. In other embodiments, n is 2. In yet other embodiments, n is 3. In yet other embodiments, n is 4. In yet other embodiments, n is 5. In yet other embodiments, n is 6. In yet other embodiments, n is 7. In yet other embodiments, n is 8. In yet other embodiments, n is 9. In yet other embodiments, n is 10. In yet other embodiments, each occurrence of n is independently selected from the group consisting of an integer ranging from 1 to 10, from 2 to 10, from 3 to 10, from 4 to 10, from 5 to 10, from 6 to 10, from 7 to 10, from 8 to 10, from 9 to 10, from 1 to 9, from 2 to 9, from 3 to 9, from 4 to 9, from 5 to 9, from 6 to 9, from 7 to 9, from 8 to 9, from 1 to 8, from 2 to 8, from 3 to 8, from 4 to 8, from 5 to 8, from 6 to 8, from 7 to 8, from 1 to 7, from 2 to 7, from 3 to 7, from 4 to 7, from 5 to 7, from 6 to 7, from 1 to 6, from 2 to 6, from 3 to 6, from 4 to 6, from 5 to 6, from 1 to 5, from 2 to 5, from 3 to 5, from 4 to 5, from 1 to 4, from 2 to 4, from 3 to 4, from 1 to 3, from 2 to 3, and from 1 to 2.

In certain embodiments, the PROTEIN or mutant thereof is modified with a segment of the extracellular region of NPP2 containing a furin cleavage site, as compared to SEQ ID NO:1. In other embodiments, the PROTEIN or mutant thereof is not modified with a segment of the extracellular region of NPP2 containing a furin cleavage site, as compared to SEQ ID NO:1.

In certain embodiments, the PROTEIN or mutant thereof is modified with a segment of the extracellular region of NPP2 containing a signal peptidase cleavage site, as compared to SEQ ID NO: 1. In other embodiments, the PROTEIN or mutant thereof is not modified with a segment of the extracellular region of NPP2 containing a signal peptidase cleavage site, as compared to SEQ ID NO: 1

In certain embodiments, the compound of formula (I) or (II) is soluble. In other embodiments, the compound of formula (I) or (II) is a recombinant polypeptide. In yet other embodiments, the compound of formula (I) or (II) includes an NPP1 polypeptide or mutant thereof that lacks the NPP1 transmembrane domain. In yet other embodiments, the compound of formula (I) or (II) includes an NPP1 polypeptide or mutant thereof, wherein the NPP1 transmembrane domain or mutant thereof has been removed (and/or truncated) and replaced with the transmembrane domain of another polypeptide, such as, by way of non-limiting example, NPP2.

In certain embodiments, the compound of formula (I) or (II) comprises an NPP1 polypeptide or mutant thereof further comprising more than one transmembrane domain.

In certain embodiments, NPP1 is C-terminally fused to the Fc domain of human immunoglobulin 1 (IgG1).

In certain embodiments, NPP1 is C-terminally fused to human serum albumin.

In certain embodiments, a fragment and/or variant of NPP1 is fused with human serum albumin or variants and/or fragments thereof. Human serum albumin may be conjugated to NPP1 protein through a chemical linker, including but not limited to naturally occurring or engineered disulfide bonds, or by genetic fusion to NPP1, or a fragment and/or variant thereof.

In certain embodiment, the compound of formula (I) or (II) comprises an NPP1 polypeptide or mutant thereof comprising transmembrane domains of NPP1 and another polypeptide, such as, by way of non-limiting example, NPP2.

In certain embodiments, the compound of the formula (I) has a sequence selected from the group consisting of SEQ ID NOs:21, 22 and 25.

In certain embodiments, the compound of the formula (I) has a sequence selected from the group consisting of SEQ ID NOs:21, 22, 25 and (SEQ ID NO:17)-Z-(SEQ ID NO:27).

In certain embodiments, the compound of the formula (I) has a sequence selected from the group consisting of SEQ ID NOs:16, 18, 20 and (SEQ ID NO:24)-Z-(SEQ ID NO:26).

In certain embodiments, the compounds of the invention have more than one transmembrane domain. In other embodiments, the compounds of the invention are further pegylated. In yet other embodiments, the compounds of the invention have more than one transmembrane domain and are further pegylated.

In certain embodiments, the compound of formula (I) or (II) has a $k_{cat}$ value greater than or equal to about 3.4 (±0.4) $s^{-1}$ enzyme$^{-1}$, wherein the $k_{cat}$ is determined by measuring the rate of hydrolysis of ATP for the compound.

In certain embodiments, the compound of formula (I) or (II) has a $K_M$ value less than or equal to about 2 µM, wherein the $K_M$ is determined by measuring the rate of hydrolysis of ATP for the compound.

In certain embodiments, the compound of formula (I) or (II) is formulated as a liquid formulation.

The invention further provides a dry product form of a pharmaceutical composition comprising a therapeutic amount of a compound of formula (I) or (II), whereby the dry product is reconstitutable to a solution of the compound in liquid form.

Methods

The invention provides methods of treating or preventing disorders and diseases in a subject where an increased activity or level of NPP1 polypeptide, fragment, derivative, mutant, or mutant fragment thereof is desirable. In certain embodiments, the subject is administered a therapeutically effective amount of at least one compound of the invention.

The invention further provides a method of treating or preventing a disease or disorder associated with pathological calcification or pathological ossification in a subject in need thereof, the method comprising administering to the subject a therapeutically effective amount of at least one compound of formula (I) or (II), wherein the disease comprises GACI, IIAC, OPLL, hypophosphatemic rickets, osteoarthritis, and calcification of atherosclerotic plaques.

The invention further provides a method of treating or preventing a disease or disorder associated with pathological calcification or pathological ossification in a subject in need thereof, the method comprising administering to the subject a therapeutically effective amount of at least one compound of formula (I) or (II), wherein the disease comprises PXE, hereditary and non-hereditary forms of osteoarthritis, ankylosing spondylitis, hardening of the arteries occurring with aging, or calciphylaxis resulting from end stage renal disease.

The invention further provides a method of reducing or preventing cardiac and/or arterial calcifications in an infant afflicted with generalized arterial calcification of infancy (GACI). In certain embodiments, the method comprises administering to the infant a therapeutically effective amount of a compound comprising (or consisting of) an ecto-nucleotide pyrophosphate/phosphodiesterase-1 (NPP1) polypeptide comprising (or fused to) an IgG Fc domain, wherein the compound lacks a polyaspartic acid domain, whereby the administering of the compound increases extracellular pyrophosphate (PPi) concentrations, thus reducing or preventing cardiac and/or arterial calcifications in the infant.

The invention further provides a method of reducing or preventing cardiac and/or arterial calcifications in an infant afflicted with generalized arterial calcification of infancy (GACI). In certain embodiments, the method comprises administering to the infant a therapeutically effective amount of a compound comprising (or consisting of) an ecto-nucleotide pyrophosphate/phosphodiesterase-1 (NPP1) polypeptide comprising (or fused to) a human serum albumin domain or fragment thereof, wherein the compound lacks a polyaspartic acid domain, whereby the administering increases extracellular pyrophosphate (PPi) concentrations, thus reducing or preventing cardiac and/or arterial calcifications in the infant.

In certain embodiments, the disorders and diseases comprise at least one selected from the group consisting of GACI, IIAC, OPLL, hypophosphatemic rickets, osteoarthritis, progeria, and calcification of atherosclerotic plaques. In other embodiments, the disorders or diseases comprise at least one selected from the group consisting of PXE, hereditary and non-hereditary forms of osteoarthritis, ankylosing spondylitis, hardening of the arteries occurring with aging, progeria, and calciphylaxis resulting from end stage renal disease.

In certain embodiments, the compound is administered acutely or chronically to the subject. In other embodiments, the compound is administered locally, regionally or systemically to the subject. In yet other embodiments, the administration is subcutaneous. In yet other embodiments, the subject is a mammal. In yet other embodiments, the mammal is human.

In certain embodiments, the compound of formula (I) or (II), fragment or mutant thereof has lower Ap3A hydrolytic activity as compared to the corresponding wild-type NPP1 polypeptide or fragment thereof. In other embodiments, the compound of formula (I) or (II), fragment or mutant thereof has substantially the same ATP hydrolytic activity as compared to the corresponding wild-type NPP1 polypeptide or fragment thereof. In yet other embodiments, the compound of formula (I) or (II), fragment or mutant thereof has lower Ap3A hydrolytic activity and substantially the same ATP hydrolytic activity as compared to the corresponding wild-type NPP1 polypeptide or fragment thereof.

In certain embodiments, the NPP1 polypeptide comprises a cleavage product of a precursor NPP1 polypeptide comprising an NPP2 transmembrane domain.

In certain embodiments, the NPP2 transmembrane domain comprises residues 12-30 of NCBI accession no. NP_001124335 (SEQ ID NO:2), which corresponds to IIS-LFTFAVGVNICLGFTA (SEQ ID NO:23).

In certain embodiments, administration of therapeutically effective amount comprises about 3-15 mg/kg qd of the NPP1-Fc polypeptide.

In certain embodiments, the administration results in reducing the infant's extracellular pyrophosphate concentrations to a level that is within the range that is found in an infant not afflicted with GACI. In certain embodiments, the infant presents and/or is diagnosed with "failure to thrive" prior to the administration.

One skilled in the art, based upon the disclosure provided herein, would understand that the invention is useful in subjects who, in whole (e.g., systemically) or in part (e.g., locally, tissue, organ), are being, or will be, treated for pathological calcification or ossification. In certain embodiments, the invention is useful in treating or preventing pathological calcification or ossification. The skilled artisan will appreciate, based upon the teachings provided herein, that the diseases and disorders treatable by the compositions and methods described herein encompass any disease or disorder where a decrease in calcification or ossification will promote a positive therapeutic outcome.

It will be appreciated by one of skill in the art, when armed with the present disclosure including the methods detailed herein, that the invention is not limited to treatment of a disease or disorder once is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that a compound of formula (I) or (II), or a mutant thereof, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject a compound of formula (I) or (II), or a mutant thereof as a preventative measure against a disease or disorder.

The invention encompasses administration of a compound of formula (I) or (II), or a mutant thereof to practice the methods of the invention; the skilled artisan would understand, based on the disclosure provided herein, how to formulate and administer the compound of formula (I) or (II), or a mutant thereof to a subject. However, the present invention is not limited to any particular method of administration or treatment regimen. This is especially true where it would be appreciated by one skilled in the art, equipped with the disclosure provided herein, including the reduction to practice using an art-recognized model of pathological calcification or ossification, that methods of administering a compound of the invention can be determined by one of skill in the pharmacological arts.

Pharmaceutical Compositions and Formulations

The invention provides pharmaceutical compositions comprising a compound of formula (I) or (II) within the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between about 0.1% and about 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions are formulated using one or more pharmaceutically acceptable excipients or carriers. In certain embodiments, the pharmaceutical compositions comprise a therapeutically effective amount of the active agent and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are used in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particular preservative is a combination of about 0.5% to 2.0% benzyl alcohol and 0.05% to 0.5% sorbic acid.

The composition may include an antioxidant and a chelating agent, which inhibit the degradation of the compound. Illustrative antioxidants for some compounds are BHT, BHA, alpha-tocopherol and ascorbic acid in the illustrative range of about 0.01% to 0.3%, for example BHT in the range of 0.03% to 0.1% by weight by total weight of the composition. The chelating agent may be present in an amount ranging from 0.01% to 0.5% by weight by total weight of the composition. Illustrative chelating agents include edetate salts (e.g. disodium edetate) and citric acid in the weight range of about 0.01% to 0.20%, for example in the range of 0.02% to 0.10% by weight by total weight of the composition. The chelating agent is useful for chelating metal ions in the composition, which may be detrimental to the shelf life of the formulation. While BHT and disodium edetate are illustrative antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives (e.g., sodium carboxymethylcellulose, hydroxypropylmethylcellulose, methylcellulose). Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one that comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. For example, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, p such as a mammal, such as a human, may be carried out using known procedures, at dosages and for periods of time effective to treat a disease or disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition. For example, In certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form. For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation. In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Methods and Materials:
ENPP1-asj GACI Mouse Model:

Heterozygous ENPP1-asj/+ breeding pairs were maintained on the 'acceleration diet' (TD00.442, Harlan Laboratories, Madison Wis.) throughout the entire experiment to generate ENPP1-WT and ENPP1-asj/asj sibling pairs that had been exposed to the acceleration diet in utero. Liters were genotyped on day 8 and weaned at day 21. Following weaning, sibling pairs were divided into experimental cohorts and all experimental animals were maintained on the acceleration diet through completion of the study.

ENPP1-Fc Design:

Modified, human and mouse NPP1 (Human: NCBI accession NP_006199; Mouse: NCBI accession NP_03839) modified to express soluble, recombinant protein was fused to IgG1 by subcloning into pFUSE-hIgG1-Fc1 or pFUSE-mIgG1-Fc1 plasmids (InvivoGen, San Diego Calif.), respectively.

Protein Production:

Shaking Flasks:

Stable transfections of the ENPP1-Fc were established in HEK293 cells under zeocin selection, and adherent HEK293 cells were adapted for suspension growth. Adapted cells were used to seed liquid culture growths in FreeStyle medium (Gibco #12338-018) in shaker flasks at 37° C. and 5% $CO_2$, agitated at 120 rpm with high humidity. The culture was gradually expanded to the desired target volume and then maintained for another 12 days to accumulate extracellular protein. During the maintenance phase, cultures were supplemented with CD EfficientFeed C AGT (Gibco #A13275-05) to enhance protein production.

Bioreactor:

Cells were propagated in a 10 liter bioreactor equipped with dissolved oxygen and pH control. Dissolved oxygen was kept at 40% air saturation by supplying the culture with mixture of air and oxygen not exceeding 3 liter per minute at an agitation rate of 80 RPM. pH was controlled at 7.4 by sparging $CO_2$ when the pH was higher than 7.4. Culture growth was followed by measuring cell number, cell viability, glucose and lactate concentrations. Final yields for both methods of production were approximately 5 mg of purified ENPP1-Fc per liter of culture.

Figure 10:
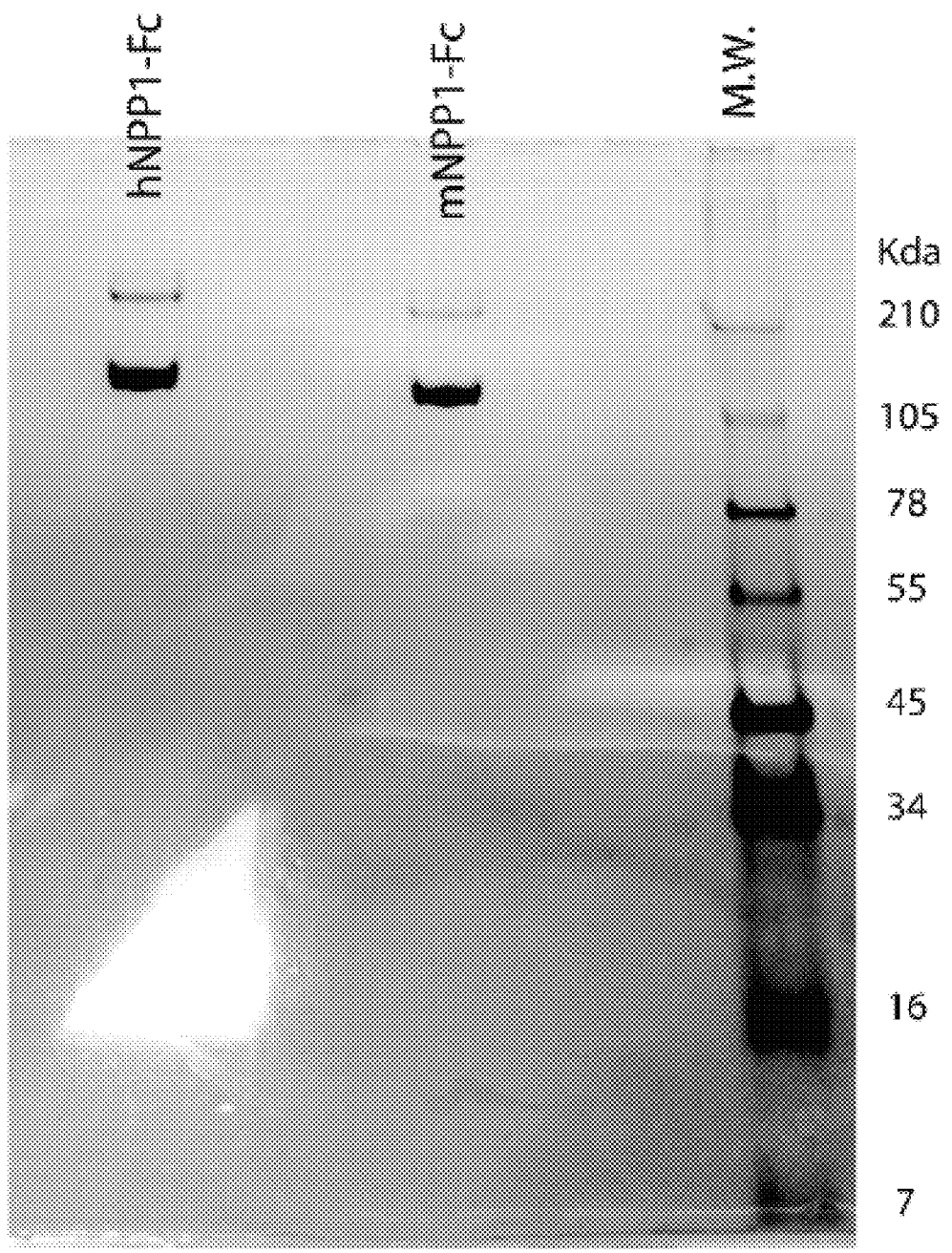
FIG. 10 is an image illustrating a silver staining image from purified human and mouse NPP1-Fc constructs.

Protein Purification:

The liquid cultures were centrifuged at 4300×g for 15 min and the supernatants were filtered through a 0.2 μm membrane and concentrated via tangential flow using a Pellicon®3 0.11 m² Ultracell® 30 kD cassette (Millipore, Billerica Mass.). The concentrated supernatant was then purified by a combination of chromatographic techniques in a multistep process. These techniques are performed sequentially and may include any of the following: affinity chromatography with protein A or protein G, cation-exchange chromatography, anion-exchange chromatography, size exclusion chromatography, hydrophobic exchange chromatography, high-pressure liquid chromatography (HPLC), precipitation steps, extractions steps, lyophylizations steps, and/or crystallization steps. Using any one of these steps in series, one schooled in the art of protein chemistry can purify the compositions of matter described to homogeneity such that there are no contaminating protein bands on a silver stained gel (in a non-limiting exemplification, FIG. 10). The resulting protein samples then tested with Pierce LAL Chromogenic Endotoxin Quantitation Kit (cat. 88282) to verify that all were free of endotoxin.

Enzymology:

The steady state hydrolysis of ATP by human NPP1 was determined by HPLC. Briefly, enzyme reactions were started by addition of 10 nM NPP1 to varying concentrations of ATP in the reaction buffer containing 20 mM Tris, pH 7.4, 150 mM NaCl, 4.5 mM KCl, 14 μM $ZnCl_2$, 1 mM $MgCl_2$ and 1 mM $CaCl_2$. At various time points, 50 μL reaction solution were removed and quenched with an equal volume of 3M formic acid. The quenched reaction solution was loaded on a C-18 (5 μm 250×4.6 mm) column (Higgins Analytical) equilibrated in 15 mM ammonium acetate (pH 6.0) solution and eluted with a 0% to 20% methanol gradient. Substrate and products were monitored by UV absorbance at 259 nm and quantified according to the integration of their correspondent peaks and standard curves.

Vehicle:

mENPP1-Fc was formulated in vehicle such that the volume of vehicle delivered was 16 μl vehicle/gram of body weight. Vehicle consisted of americanBio 10×PBS (Stock# AB11072) diluted to 1× with endotoxin free water and supplemented with 14 μM $CaCl_2$ and 14 μM $ZnCl_2$.

Dosing:

Animals were dosed either with vehicle or with mouse ENPP1-Fc (mENPP1-Fc) formulated in vehicle. Mice were dosed with daily subcutaneous injections starting on day 14 at dose levels of 500 au/Kg mENPP1-Fc.

Enzyme Activity:

In certain embodiments, enzymes useful within the invention have enzymatic activity with the Michaelis Menton constants as described in Albright, et al., 2015, Nature Comm. 6:10006 ($K_M$~2 μM for ATP hydrolysis; $k_{cat}$ of 3.46 (±0.44) $s^{-1}$).

Quantification of Plasma PPi:

ENPP1-WT and dosed ENPP1-asj/asj animals were terminally bled retro-orbitally using heparinized micropipttes, and the blood was immediately dispensed into heparin-treated eppendorf tubes and placed on wet ice. The samples were spun in a 4° C. pre-cooled microcentrifuge at 4000 rpm for 5 minutes, and plasma was collected and diluted in one volume of 50 mM Tris-Acetate pH=8.0 and frozen at −80° C. Quantitation of serum PPi was performed using as described previously (Cheung & Suhadolnik, 1977, Anal Biochem 83:61-63).

Micro-CT Scans:

In Vivo $^{99m}$PYP Imaging:

The bone imaging agent $^{99m}$Tc-pyrophosphate (Pharmalucence, Inc) was evaluated in cohorts of animals using a preclinical microSPECT/CT hybrid imaging system with dual 1 mm pinhole collimators (X-SPECT, Gamma Medica-Ideas). Each animal was injected ip with 2-5 mCi of the radiolabeled tracer and imaged 1-1.5 hr after injection. A CT scan (512 projections at 50 kVp, 800 uA and a magnification factor of 1.25) was acquired for anatomical co-localization with the SPECT image. The SPECT imaging was acquired with 180° per collimator head in a counter-clockwise rotation, 32 projections, 60 seconds per projection with an ROR of 7.0 cm, FOV of 8.95 cm and an energy window of 140 keV±20. CT images were reconstructed with the FLEX X-O CT software (Gamma Medica-Ideas) using a filtered backprojection algorithm. SPECT images were reconstructed using FLEX SPECT software (5 iterations, 4 subsets) and subsequently fused with the CT images and analyzed using AMIRA software and offline in-house script. Data was corrected for decay and injected dose to achieve % injected dose (% ID).

Quantification of $^{99m}$PYP Uptake:

For the $^{99m}$PYP murine scans, the animals were imaged two hours postinjection. The resulting SPECT scans were imported into NIH's ImageJ image processing software and ROI's were drawn around each animal's head (target organ) and whole body. Percent injected activity (PIA), often referred to as "percent injected dose" (% ID) was calculated by comparing the ratio of counts in the head to the counts in the whole body, and expressed as % ID to give a measure as of the affinity with which the radiotracer is taken up by the ROI (head). The total counts in each scan were taken as the whole body measure of injected dose.

Sequences:

```
NPP1 Amino Acid Sequence (NCBI accession NP_006199)
                                                        (SEQ ID NO: 1)
MERDGCAGGGSRGGEGGRAPREGPAGNGRDRGRSHAAEAPGDPQAAASLLAPMDVGEEPLEKAARAR

TAKDPNTYKVLSLVLSVCVLTTILGCIFGLKPSCAKEVKSCKGRCFERTFGNCRCDAACVELGNCCL

DYQETCIEPEHIWTCNKFRCGEKRLTRSLCACSDDCKDKGDCCINYSSVCQGEKSWVEEPCESINEP

QCPAGFETPPTLLFSLDGFRAEYLHTWGGLLPVISKLKKCGTYTKNMRPVYPTKTFPNHYSIVTGLY

PESHGIIDNKMYDPKMNASFSLKSKEKFNPEWYKGEPIWVTAKYQGLKSGTFFWPGSDVEINGIFPD

IYKMYNGSVPFEERILAVLQWLQLPKDERPHFYTLYLEEPDSSGHSYGPVSSEVIKALQRVDGMVGM

LMDGLKELNLHRCLNLILISDHGMEQGSCKKYIYLNKYLGDVKNIKVIYGPAARLRPSDVPDKYYSF

NYEGIARNLSCREPNQHFKPYLKHFLPKRLHFAKSDRIEPLTFYLDPQWQLALNPSERKYCGSGFHG

SDNVFSNMQALFVGYGPGFKHGIEADTFENIEVYNLMCDLLNLTPAPNNGTHGSLNHLLKNPVYTPK

HPKEVHPLVQCPFTRNPRDNLGCSCNPSILPIEDFQTQFNLTVAEEKIIKHETLPYGRPRVLQKENT

ICLLSQHQFMSGYSQDILMPLWTSYTVDRNDSFSTEDFSNCLYQDFRIPLSPVHKCSFYKNNTKVSY

GFLSPPQLNKNSSGIYSEALLTTNIVPMYQSFQVIWRYFHDTLLRKYAEERNGVNVVSGPVFDFDYD

GRCDSLENLRQKRRVIRNQEILIPTHFFIVLTSCKDTSQTPLHCENLDTLAFILPHRTDNSESCVHG

KHDSSWVEELLMLHRARITDVEHITGLSFYQQRKEPVSDILKLKTHLPTFSQED

NPP2 Amino Acid Sequence (NCBI accession NP_001124335)
                                                        (SEQ ID NO: 2)
MARRSSFQSCQIISLFTFAVGVNICLGFTAHRIKRAEGWEEGPPTVLSDSPWTNISGSCKGRCFELQ

EAGPPDCRCDNLCKSYTSCCHDFDELCLKTARGWECTKDRCGEVRNEENACHCSEDCLARGDCCTNY

QVVCKGESHWVDDDCEEIKAAECPAGFVRPPLIIFSVDGFRASYMKKGSKVMPNIEKLRSCGTHSPY

MRPVYPTKTFPNLYTLATGLYPESHGIVGNSMYDPVFDATFHLRGREKFNHRWWGGQPLWITATKQG

VKAGTFFWSVVIPHERRILTILQWLTLPDHERPSVYAFYSEQPDFSGHKYGPFGPEMTNPLREIDKI

VGQLMDGLKQLKLHRCVNVIFVGDHGMEDVTCDRTEFLSNYLTNVDDITLVPGTLGRIRSKFSNNAK

YDPKAIIANLTCKKPDQHFKPYLKQHLPKRLHYANNRRIEDIHLLVERRWHVARKPLDVYKKPSGKC

FFQGDHGEDNKVNSMQTVFVGYGSTFKYKTKVPPFENIELYNVMCDLLGLKPAPNNGTHGSLNHLLR

TNTFRPTMPEEVTRPNYPGIMYLQSDFDLGCTCDDKVEPKNKLDELNKRLHTKGSTEAETRKFRGSR

NENKENINGNFEPRKERHLLYGRPAVLYRTRYDILYHTDFESGYSEIFLMPLWTSYTVSKQAEVSSV

PDHLTSCVRPDVRVSPSFSQNCLAYKNDKQMSYGFLFPPYLSSSPEAKYDAFLVTNMVPMYPAFKRV

WNYFQRVLVKKYASERNGVNVISGPIFDYDYDGLHDTEDKIKQYVEGSSIPVPTHYYSIITSCLDFT

QPADKCDGPLSVSSFILPHRPDNEESCNSSEDESKWVEELMKMHTARVRDIEHLTSLDFFRKTSRSY
```

PEILTLKTYLHTYESEI

NPP4 Amino Acid Sequence (NCBI accession AAH18054.1)

(SEQ ID NO: 3)
MKLLVILLFSGLITGFRSDSSSSLPPKLLLVSFDGFRADYLKNYEFPHLQNFIKEGVLVEHVKNVFI

TKTFPNHYSIVTGLYEESHGIVANSMYDAVTKKHFSDSNDKDPFWWNEAVPIWVTNQLQENRSSAAA

MWPGTDVPIHDTISSYFMNYNSSVSFEERLNNITMWLNNSNPPVTFATLYWEEPDASGHKYGPEDKE

NMSRVLKKIDDLIGDLVQRLKMLGLWENLNVIITSDHGMTQCSQDRLINLDSCIDHSYYTLIDLSPV

AAILPKINRTEVYNKLKNCSPHMNVYLKEDIPNRFYYQHNDRIQPIILVADEGWTIVLNESSQKLGD

HGYDNSLPSMHPFLAAHGPAFHKGYKHSTINIVDIYPMMCHILGLKPHPNNGTFGHTKCLLVDQWCI

NLPEAIAIVIGSLLVLTMLTCLIIMQNRLSVPRPFSRLQLQEDDDDPLIG (SEQ ID NO: 4)
(DSS)$_n$,
wherein n is an integer ranging from 1 to 10

(SEQ ID NO: 5)
(ESS)$_n$,
wherein n is an integer ranging from 1 to 10

(SEQ ID NO: 6)
(RQQ)$_n$,
wherein n is an integer ranging from 1 to 10

(SEQ ID NO: 7)
(KR)$_n$,
wherein n is an integer ranging from 1 to 10

(SEQ ID NO: 8)
R$_m$,
wherein m is an integer ranging from 1 to 15

(SEQ ID NO: 9)
DSSSEEKFLRRIGRFG

(SEQ ID NO: 10)
EEEEEEEPRGDT

(SEQ ID NO: 11)
APWHLSSQYSRT

(SEQ ID NO: 12)
STLPIPHEFSRE

(SEQ ID NO: 13)
VTKHLNQISQSY

(SEQ ID NO: 14)
E$_m$,
wherein m is an integer ranging from 1 to 15

NPP121 Amino Acid Sequence (SEQ ID NO: 15)

|     |   |   |   |   |   |   |   |   |   |   |   |   |   |   |   |   |   |   |   |   |
|-----|---|---|---|---|---|---|---|---|---|---|---|---|---|---|---|---|---|---|---|---|
| 1   | M | E | R | D | G | C | A | G | G | G | S | R | G | G | E | G | G | R | A | P |
| 21  | R | E | G | P | A | G | N | G | R | D | R | G | R | S | H | A | A | E | A | P |
| 41  | G | D | P | Q | A | A | A | S | L | L | A | P | M | D | V | G | E | E | P | L |
| 61  | E | K | A | A | R | A | R | T | A | K | D | P | N | T | Y | K | I | I | S | <u>L</u> |
| 81  | <u>F</u> | <u>T</u> | <u>F</u> | <u>A</u> | <u>V</u> | <u>G</u> | <u>V</u> | <u>N</u> | <u>I</u> | <u>C</u> | <u>L</u> | G**F | <u>T</u> | <u>A</u> | <u>G</u> | <u>L</u> | <u>K</u> | P | S |   |
| 101 | C | A | K | E | V | K | S | C | K | G | R | C | F | E | R | T | F | G | N | C |
| 121 | R | C | D | A | A | C | V | E | L | G | N | C | C | L | D | Y | Q | E | T | C |
| 141 | I | E | P | E | H | I | W | T | C | N | K | F | R | C | G | E | K | R | L | T |
| 161 | R | S | L | C | A | C | S | D | D | C | K | D | K | G | D | C | C | I | N | Y |
| 181 | S | S | V | C | Q | G | E | K | S | W | V | E | E | P | C | E | S | I | N | E |
| 201 | P | Q | C | P | A | G | F | E | T | P | P | T | L | L | F | S | L | D | G | F |

-continued

```
221  R  A  E  Y  L  H  T  W  G  G  L  L  P  V  I  S  K  L  K  K
241  C  G  T  Y  T  K  N  M  R  P  V  Y  P  T  K  T  F  P  N  H
261  Y  S  I  V  T  G  L  Y  P  E  S  H  G  I  I  D  N  K  M  Y
281  D  P  K  M  N  A  S  F  S  L  K  S  K  E  K  F  N  P  E  W
301  Y  K  G  E  P  I  W  V  T  A  K  Y  Q  G  L  K  S  G  T  F
321  F  W  P  G  S  D  V  E  I  N  G  I  F  P  D  I  Y  K  M  Y
341  N  G  S  V  P  F  E  E  R  I  L  A  V  L  Q  W  L  Q  L  P
361  K  D  E  R  P  H  F  Y  T  L  Y  L  E  E  P  D  S  S  G  H
381  S  Y  G  P  V  S  S  E  V  I  K  A  L  Q  R  V  D  G  M  V
401  G  M  L  M  D  G  L  K  E  L  N  L  H  R  C  L  N  L  I  L
421  I  S  D  H  G  M  E  Q  G  S  C  K  K  Y  I  Y  L  N  K  Y
441  L  G  D  V  K  N  I  K  V  I  Y  G  P  A  A  R  L  R  P  S
461  D  V  P  D  K  Y  Y  S  F  N  Y  E  G  I  A  R  N  L  S  C
481  R  E  P  N  Q  H  F  K  P  Y  L  K  H  F  L  P  K  R  L  H
501  F  A  K  S  D  R  I  E  P  L  T  F  Y  L  D  P  Q  W  Q  L
521  A  L  N  P  S  E  R  K  Y  C  G  S  G  F  H  G  S  D  N  V
541  F  S  N  M  Q  A  L  F  V  G  Y  G  P  G  F  K  H  G  I  E
561  A  D  T  F  E  N  I  E  V  Y  N  L  M  C  D  L  L  N  L  T
581  P  A  P  N  N  G  T  H  G  S  L  N  H  L  L  K  N  P  V  Y
601  T  P  K  H  P  K  E  V  H  P  L  V  Q  C  P  F  T  R  N  P
621  R  D  N  L  G  C  S  C  N  P  S  I  L  P  I  E  D  F  Q  T
641  Q  F  N  L  T  V  A  E  E  K  I  I  K  H  E  T  L  P  Y  G
661  R  P  R  V  L  Q  K  E  N  T  I  C  L  L  S  Q  H  Q  F  M
681  S  G  Y  S  Q  D  I  L  M  P  L  W  T  S  Y  T  V  D  R  N
701  D  S  F  S  T  E  D  F  S  N  C  L  Y  Q  D  F  R  I  P  L
721  S  P  V  H  K  C  S  F  Y  K  N  N  T  K  V  S  Y  G  F  L
741  S  P  P  Q  L  N  K  N  S  S  G  I  Y  S  E  A  L  L  T  T
761  N  I  V  P  M  Y  Q  S  F  Q  V  I  W  R  Y  F  H  D  T  L
781  L  R  K  Y  A  E  E  R  N  G  V  N  V  V  S  G  P  V  F  D
801  F  D  Y  D  G  R  C  D  S  L  E  N  L  R  Q  K  R  R  V  I
821  R  N  Q  E  I  L  I  P  T  H  F  F  I  V  L  T  S  C  K  D
841  T  S  Q  T  P  L  H  C  E  N  L  D  T  L  A  F  I  L  P  H
861  R  T  D  N  S  E  S  C  V  H  G  K  H  D  S  S  W  V  E  E
881  L  L  M  L  H  R  A  R  I  T  D  V  E  H  I  T  G  L  S  F
901  Y  Q  Q  R  K  E  P  V  S  D  I  L  K  L  K  T  H  L  P  T
921  F  S  Q  E  D
```

Singly Underlined: residues swapped with NPP2 residues 1-27 to afford cleavage at transition position (**); Doubly Underlined: NPP1 protein (beginning and end).

NPP121-Fc Amino Acid Sequence (SEQ ID NO: 16)

```
  1  M E R D G C A G G G S R G G E G G R A P

21  R E G P A G N G R D R G R S H A A E A P
```

-continued

```
 41    G  D  P  Q  A  A  A  S  L  L  A  P  M  D  V  G  E  E  P  L
 61    E  K  A  A  R  A  R  T  A  K  D  P  N  T  Y  K  I  I  S  L
 81    F  T  F  A  V  G  V  N  I  C  L  G**F  T  A  G  L  K  P  S
101    C  A  K  E  V  K  S  C  K  G  R  C  F  E  R  T  F  G  N  C
121    R  C  D  A  A  C  V  E  L  G  N  C  C  L  D  Y  Q  E  T  C
141    I  E  P  E  H  I  W  T  C  N  K  F  R  C  G  E  K  R  L  T
161    R  S  L  C  A  C  S  D  D  C  K  D  K  G  D  C  C  I  N  Y
181    S  S  V  C  Q  G  E  K  S  W  V  E  E  P  C  E  S  I  N  E
201    P  Q  C  P  A  G  F  E  T  P  P  T  L  L  F  S  L  D  G  F
221    R  A  E  Y  L  H  T  W  G  G  L  L  P  V  I  S  K  L  K  K
241    C  G  T  Y  T  K  N  M  R  P  V  Y  P  T  K  T  F  P  N  H
261    Y  S  I  V  T  G  L  Y  P  E  S  H  G  I  I  D  N  K  M  Y
281    D  P  K  M  N  A  S  F  S  L  K  S  K  E  K  F  N  P  E  W
301    Y  K  G  E  P  I  W  V  T  A  K  Y  Q  G  L  K  S  G  T  F
321    F  W  P  G  S  D  V  E  I  N  G  I  F  P  D  I  Y  K  M  Y
341    N  G  S  V  P  F  E  E  R  I  L  A  V  L  Q  W  L  Q  L  P
361    K  D  E  R  P  H  F  Y  T  L  Y  L  E  E  P  D  S  S  G  H
381    S  Y  G  P  V  S  S  E  V  I  K  A  L  Q  R  V  D  G  M  V
401    G  M  L  M  D  G  L  K  E  L  N  L  H  R  C  L  N  L  I  L
421    I  S  D  H  G  M  E  Q  G  S  C  K  K  Y  I  Y  L  N  K  Y
441    L  G  D  V  K  N  I  K  V  I  Y  G  P  A  A  R  L  R  P  S
461    D  V  P  D  K  Y  Y  S  F  N  Y  E  G  I  A  R  N  L  S  C
481    R  E  P  N  Q  H  F  K  P  Y  L  K  H  F  L  P  K  R  L  H
501    F  A  K  S  D  R  I  E  P  L  T  F  Y  L  D  P  Q  W  Q  L
521    A  L  N  P  S  E  R  K  Y  C  G  S  G  F  H  G  S  D  N  V
541    F  S  N  M  Q  A  L  F  V  G  Y  G  P  G  F  K  H  G  I  E
561    A  D  T  F  E  N  I  E  V  Y  N  L  M  C  D  L  L  N  L  T
581    P  A  P  N  N  G  T  H  G  S  L  N  H  L  L  K  N  P  V  Y
601    T  P  K  H  P  K  E  V  H  P  L  V  Q  C  P  F  T  R  N  P
621    R  D  N  L  G  C  S  C  N  P  S  I  L  P  I  E  D  F  Q  T
641    Q  F  N  L  T  V  A  E  E  K  I  I  K  H  E  T  L  P  Y  G
661    R  P  R  V  L  Q  K  E  N  T  I  C  L  L  S  Q  H  Q  F  M
681    S  G  Y  S  Q  D  I  L  M  P  L  W  T  S  Y  T  V  D  R  N
701    D  S  F  S  T  E  D  F  S  N  C  L  Y  Q  D  F  R  I  P  L
721    S  P  V  H  K  C  S  F  Y  K  N  N  T  K  V  S  Y  G  F  L
741    S  P  P  Q  L  N  K  N  S  S  G  I  Y  S  E  A  L  L  T  T
761    N  I  V  P  M  Y  Q  S  F  Q  V  I  W  R  Y  F  H  D  T  L
781    L  R  K  Y  A  E  E  R  N  G  V  N  V  V  S  G  P  V  F  D
801    F  D  Y  D  G  R  C  D  S  L  E  N  L  R  Q  K  R  R  V  I
821    R  N  Q  E  I  L  I  P  T  H  F  F  I  V  L  T  S  C  K  D
841    T  S  Q  T  P  L  H  C  E  N  L  D  T  L  A  F  I  L  P  H
```

```
 861  R T D N S E S C V H G K H D S S W V E E
 881  L L M L H R A R I T D V E H I T G L S F
 901  Y Q Q R K E P V S D I L K L K T H L P T
 921  F S Q E D L I N D K T H T C P P C P A P
 941  E L L G G P S V F L F P P K P K D T L M
 961  I S R T P E V T C V V V D V S H E D P E
 981  V K F N W Y V D G V E V H N A K T K P R
1001  E E Q Y N S T Y R V V S V L T V L H Q D
1021  W L N G K E Y K C K V S N K A L P A P I
1041  E K T I S K A K G Q P R E P Q V Y T L P
1061  P S R E E M T K N Q V S L T C L V K G F
1081  Y P S D I A V E W E S N G Q P E N N Y K
1101  T T P P V L D S D G S F F L Y S K L T V
1121  D K S R W Q Q G N V F S C S V M H E A L
1141  H N H Y T Q K S L S L S P G K
```

Singly Underlined: residues swapped with NPP2 residues 1-27 to afford cleavage at transition position (**); Doubly Underlined: NPP1 protein (beginning and end); Bold: hIgG1 (Fc)

NPP71 Amino Acid Sequence (SEQ ID NO: 17)

```
   1  MRGPAVLLTV ALATLLAPGA GAGLKPSCAK EVKSCKGRCF ERTFGNCRCD
  51  AACVELGNCC LDYQETCIEP EHIWTCNKFR CGEKRLTRSL CACSDDCKDK
 101  GDCCINYSSV CQGEKSWVEE PCESINEPQC PAGFETPPTL LFSLDGFRAE
 151  YLHTWGGLLP VISKLKKCGT YTKNMRPVYP TKTFPNHYSI VTGLYPESHG
 201  IIDNKMYDPK MNASFSLKSK EKFNPEWYKG EPIWVTAKYQ GLKSGTFFWP
 251  GSDVEINGIF PDIYKMYNGS VPFEERILAV LQWLQLPKDE RPHFYTLYLE
 301  EPDSSGHSYG PVSSEVIKAL QRVDGMVGML MDGLKELNLH RCLNLILISD
 351  HGMEQGSCKK YIYLNKYLGD VKNIKVIYGP AARLRPSDVP DKYYSFNYEG
 401  IARNLSCREP NQHFKPYLKH FLPKRLHFAK SDRIEPLTFY LDPQWQLALN
 451  PSERKYCGSG FHGSDNVFSN MQALFVGYGP GFKHGIEADT FENIEVYNLM
 501  CDLLNLTPAP NNGTHGSLNH LLKNPVYTPK HPKEVHPLVQ CPFTRNPRDN
 551  LGCSCNPSIL PIEDFQTQFN LTVAEEKIIK HETLPYGRPR VLQKENTICL
 601  LSQHQFMSGY SQDILMPLWT SYTVDRNDSF STEDFSNCLY QDFRIPLSPV
 651  HKCSFYKNNT KVSYGFLSPP QLNKNSSGIY SEALLTTNIV PMYQSFQVIW
 701  RYFHDTLLRK YAEERNGVNV VSGPVFDFDY DGRCDSLENL RQKRRVIRNQ
 751  EILIPTHFFI VLTSCKDTSQ TPLHCENLDT LAFILPHRTD NSESCVHGKH
 801  DSSWVEELLM LHRARITDVE HITGLSFYQQ RKEPVSDILK LKTHLPTFSQ
 851  ED
```

Singly Underlined: NPP7; Doubly Underlined: NPP1 protein (beginning and end).

NPP71-Fc Amino Acid Sequence (SEQ ID NO: 18)

```
   1  MRGPAVLLTV ALATLLAPGA GAGLKPSCAK EVKSCKGRCF ERTFGNCRCD
  51  AACVELGNCC LDYQETCIEP EHIWTCNKFR CGEKRLTRSL CACSDDCKDK
 101  GDCCINYSSV CQGEKSWVEE PCESINEPQC PAGFETPPTL LFSLDGFRAE
```

```
151    YLHTWGGLLP VISKLKKCGT YTKNMRPVYP TKTFPNHYSI VTGLYPESHG

201    IIDNKMYDPK MNASFSLKSK EKFNPEWYKG EPIWVTAKYQ GLKSGTFFWP

251    GSDVEINGIF PDIYKMYNGS VPFEERILAV LQWLQLPKDE RPHFYTLYLE

301    EPDSSGHSYG PVSSEVIKAL QRVDGMVGML MDGLKELNLH RCLNLILISD

351    HGMEQGSCKK YIYLNKYLGD VKNIKVIYGP AARLRPSDVP DKYYSFNYEG

401    IARNLSCREP NQHFKPYLKH FLPKRLHFAK SDRIEPLTFY LDPQWQLALN

451    PSERKYCGSG FHGSDNVFSN MQALFVGYGP GFKHGIEADT FENIEVYNLM

501    CDLLNLTPAP NNGTHGSLNH LLKNPVYTPK HPKEVHPLVQ CPFTRNPRDN

551    LGCSCNPSIL PIEDFQTQFN LTVAEEKIIK HETLPYGRPR VLQKENTICL

601    LSQHQFMSGY SQDILMPLWT SYTVDRNDSF STEDFSNCLY QDFRIPLSPV

651    HKCSFYKNNT KVSYGFLSPP QLNKNSSGIY SEALLTTNIV PMYQSFQVIW

701    RYFHDTLLRK YAEERNGVNV VSGPVFDFDY DGRCDSLENL RQKRRVIRNQ

751    EILIPTHFFI VLTSCKDTSQ TPLHCENLDT LAFILPHRTD NSESCVHGKH

801    DSSWVEELLM LHRARITDVE HITGLSFYQQ RKEPVSDILK LKTHLPTFSQ

851    EDLINDKTHT CPPCPAPELL GGPSVFLFPP KPKDTLMISR TPEVTCVVVD

901    VSHEDPEVKF NWYVDGVEVH NAKTKPREEQ YNSTYRVVSV LTVLHQDWLN

951    GKEYKCKVSN KALPAPIEKT ISKAKGQPRE PQVYTLPPSR EEMTKNQVSL

1001   TCLVKGFYPS DIAVEWESNG QPENNYKTTP PVLDSDGSFF LYSKLTVDKS

1051   RWQQGNVFSC SVMHEALHNH YTQKSLSLSP GK
```
Singly Underlined: NPP7; Doubly Underlined: NPP1 protein
(beginning and end); Bold: hIgG1 (Fc).

(NPP71 lacking NPP1 N-Terminus GLK) Amino Acid Sequence (SEQ ID NO: 19)

```
  1    MRGPAVLLTV ALATLLAPGA GA   PSCAK EVKSCKGRCF ERTFGNCRCD

51    AACVELGNCC LDYQETCIEP EHIWTCNKFR CGEKRLTRSL CACSDDCKDK

101    GDCCINYSSV CQGEKSWVEE PCESINEPQC PAGFETPPTL LFSLDGFRAE

151    YLHTWGGLLP VISKLKKCGT YTKNMRPVYP TKTFPNHYSI VTGLYPESHG

201    IIDNKMYDPK MNASFSLKSK EKFNPEWYKG EPIWVTAKYQ GLKSGTFFWP

251    GSDVEINGIF PDIYKMYNGS VPFEERILAV LQWLQLPKDE RPHFYTLYLE

301    EPDSSGHSYG PVSSEVIKAL QRVDGMVGML MDGLKELNLH RCLNLILISD

351    HGMEQGSCKK YIYLNKYLGD VKNIKVIYGP AARLRPSDVP DKYYSFNYEG

401    IARNLSCREP NQHFKPYLKH FLPKRLHFAK SDRIEPLTFY LDPQWQLALN

451    PSERKYCGSG FHGSDNVFSN MQALFVGYGP GFKHGIEADT FENIEVYNLM

501    CDLLNLTPAP NNGTHGSLNH LLKNPVYTPK HPKEVHPLVQ CPFTRNPRDN

551    LGCSCNPSIL PIEDFQTQFN LTVAEEKIIK HETLPYGRPR VLQKENTICL

601    LSQHQFMSGY SQDILMPLWT SYTVDRNDSF STEDFSNCLY QDFRIPLSPV

651    HKCSFYKNNT KVSYGFLSPP QLNKNSSGIY SEALLTTNIV PMYQSFQVIW

701    RYFHDTLLRK YAEERNGVNV VSGPVFDFDY DGRCDSLENL RQKRRVIRNQ

751    EILIPTHFFI VLTSCKDTSQ TPLHCENLDT LAFILPHRTD NSESCVHGKH

801    DSSWVEELLM LHRARITDVE HITGLSFYQQ RKEPVSDILK LKTHLPTFSQ

851    ED
```
Singly Underlined: NPP7; Doubly Underlined: NPP1 protein
(beginning and end) (first 3-amino acids at the N-terminus
of NPP1, GLK, are omitted).

-continued (NPP71 lacking NPP1 N-Terminus GLK)-Fc Amino Acid Sequence
(SEQ ID NO: 20)

```
   1    MRGPAVLLTV ALATLLAPGA GA    PSCAK EVKSCKGRCF ERTFGNCRCD
  51    AACVELGNCC LDYQETCIEP EHIWTCNKFR CGEKRLTRSL CACSDDCKDK
 101    GDCCINYSSV CQGEKSWVEE PCESINEPQC PAGFETPPTL LFSLDGFRAE
 151    YLHTWGGLLP VISKLKKCGT YTKNMRPVYP TKTFPNHYSI VTGLYPESHG
 201    IIDNKMYDPK MNASFSLKSK EKFNPEWYKG EPIWVTAKYQ GLKSGTFFWP
 251    GSDVEINGIF PDIYKMYNGS VPFEERILAV LQWLQLPKDE RPHFYTLYLE
 301    EPDSSGHSYG PVSSEVIKAL QRVDGMVGML MDGLKELNLH RCLNLILISD
 351    HGMEQGSCKK YIYLNKYLGD VKNIKVIYGP AARLRPSDVP DKYYSFNYEG
 401    IARNLSCREP NQHFKPYLKH FLPKRLHFAK SDRIEPLTFY LDPQWQLALN
 451    PSERKYCGSG FHGSDNVFSN MQALFVGYGP GFKHGIEADT FENIEVYNLM
 501    CDLLNLTPAP NNGTHGSLNH LLKNPVYTPK HPKEVHPLVQ CPFTRNPRDN
 551    LGCSCNPSIL PIEDFQTQFN LTVAEEKIIK HETLPYGRPR VLQKENTICL
 601    LSQHQFMSGY SQDILMPLWT SYTVDRNDSF STEDFSNCLY QDFRIPLSPV
 651    HKCSFYKNNT KVSYGFLSPP QLNKNSSGIY SEALLTTNIV PMYQSFQVIW
 701    RYFHDTLLRK YAEERNGVNV VSGPVFDFDY DGRCDSLENL RQKRRVIRNQ
 751    EILIPTHFFI VLTSCKDTSQ TPLHCENLDT LAFILPHRTD NSESCVHGKH
 801    DSSWVEELLM LHRARITDVE HITGLSFYQQ RKEPVSDILK LKTHLPTFSQ
 851    EDLINDKTHT CPPCPAPELL GGPSVFLFPP KPKDTLMISR TPEVTCVVVD
 901    VSHEDPEVKF NWYVDGVEVH NAKTKPREEQ YNSTYRVVSV LTVLHQDWLN
 951    GKEYKCKVSN KALPAPIEKT ISKAKGQPRE PQVYTLPPSR EEMTKNQVSL
1001    TCLVKGFYPS DIAVEWESNG QPENNYKTTP PVLDSDGSFF LYSKLTVDKS
1051    RWQQGNVFSC SVMHEALHNH YTQKSLSLSP GK
```

Singly Underlined: NPP7; Doubly Underlined: NPP1 protein (beginning and end) (first 3-amino acids at the N-terminus of NPP1 are omitted); Bold: hIgG1 (Fc).

NPP121-ALB Amino Acid Sequence
(SEQ ID NO: 21)

***MERDGCAGGGSRGGEGGRAPREGPAGNGRDRGRSHAAEA*APGDPQAAASLLAPM*DVGEEPLEKAARAR**

TAKDPNTYKIIS<u>LFTFAVGVNICLG</u>\*\*<u>FTAGLK</u>PSCAKEVKSCKGRCFERTFGNCRCDAACVELGNC

CLDYQETCIEPEHIWTCNKFRCGEKRLTRSLCACSDDCKDKGDCCINYSSVCQGEKSWVEEPCESIN

EPQCPAGFETPPTLLFSLDGFRAEYLHTWGGLLPVISKLKKCGTYTKNMRPVYPTKTFPNHYSIVTG

LYPESHGIIDNKMYDPKMNASFSLKSKEKFNPEWYKGEPIWVTAKYQGLKSGTFFWPGSDVEINGIF

PDIYKMYNGSVPFEERILAVLQWLQLPKDERPHFYTLYLEEPDSSGHSYGPVSSEVIKALQRVDGMV

GMLMDGLKELNLHRCLNLILISDHGMEQGSCKKYIYLNKYLGDVKNIKVIYGPAARLRPSDVPDKYY

SFNYEGIARNLSCREPNQHFKPYLKHFLPKRLHFAKSDRIEPLTFYLDPQWQLALNPSERKYCGSGF

HGSDNVFSNMQALEVGYGPGFKHGIEADTFENTEVYNLMCDLLNLTPAPNNGTHGSLNHLLKNPVYT

PKHPKEVHPLVQCPFTRNPRDNLGCSCNPSILPIEDFQTQFNLTVAEEKIIKHETLPYGRPRVLQKE

NTICLLSQHQFMSGYSQDILMPLWTSYTVDRNDSFSTEDFSNCLYQDFRIPLSPVHKCSFYKNNTKV

SYGFLSPPQLNKNSSGIYSEALLTTNIVPMYQSFQVIWRYFHDTLLRKYAEERNGVNVVSGPVFDFD

YDGRCDSLENLRQKRRVIRNQEILIPTHFFIVLTSCKDTSQTPLHCENLDTLAFILPHRTDNSESCV

HGKHDSSWVEELLMLHRARITDVEHITGLSFYQQRKEPVSDILKLKTHLPTFSQED<u>RSGSGGSMKWV</u>

TFLLLLLFVSGSAFSRGVFRREAHKSEIAHRYNDLGEQHFKGLVLIAFSQYLQKCSYDEHAKLVQEVT

-continued

DFAKTCVADESAANCDKSLHTLFGDKLCAIPNLRENYGELADCCTKQEPERNECFLQHKDDNPSLPP

FERPEAEAMCTSFKENPTTFMGHYLHEVARRHPYFYAPELLYYAEQYNEILTQCCAEADKESCLTPK

LDGVKEKALVSSVRQRMKCSSMQKFGERAFKAWAVARLSQTFPNADFAEITKLATDLTKVNKECCHG

DLLECADDRAELAKYMCENQATISSKLQTCCDKPLLKKAHCLSEVEHDTMPADLPAIAADFVEDQEV

CKNYAEAKDVFLGTFLYEYSRRHPDYSVSLLLRLAKKYEATLEKCCAEANPPACYGTVLAEFQPLVE

EPKNLVKTNCDLYEKLGEYGFQNAILVRYTQKAPQVSTPTLVEAARNLGRVGTKCCTLPEDQRLPCV

EDYLSAILNRVCLLHEKTPVSEHVTKCCSGSLVERRPCFSALTVDETYVPKEFKAETFTFHSDICTL

PEKEKQIKKQTALAELVKHKPKATAEQLKTVMDDFAQFLDTCCKAADKDTCFSTEGPNLVTRCKDAL

ARSWSHPQFEK

Bold Italics: NPP1 cytoplasmic and transmembrane; Singly Underlined: Swapped residues with NPP2 residues 1-27 to give cleavage at transition position (**); Doubly Underlined: NPP1 transmembrane; Plain: NPP1 Extracellular Domain; Bold Underlined: Linker; Bold: Albumin (NPP71 lacking NPP1 N-Terminus GLK)-ALB Amino Acid Sequence
(SEQ ID NO: 22)

MRGPAVLLTVALATLLAPGAGAPSCAKEVKSCKGRCFERTEGNCRCDAACVELGNCCLDYQETCIEP

EHIWTCNKFRCGEKRLTRSLCACSDDCKDKGDCCINYSSVCQGEKSWVEEPCESINEPQCPAGFETP

PTLLFSLDGFRAEYLHTWGGLLPVISKLKKCGTYTKNMRPVYPTKTFPNHYSIVTGLYPESHGIIDN

KMYDPKMNASFSLKSKEKFNPEWYKGEPIWVTAKYQGLKSGTFFWPGSDVEINGIFPDIYKMYNGSV

PFEERILAVLQWLQLPKDERPHFYTLYLEEPDSSGHSYGPVSSEVIKALQRVDGMVGMLMDGLKELN

LHRCLNLILISDHGMEQGSCKKYIYLNKYLGDVKNIKVIYGPAARLRPSDVPDKYYSFNYEGIARNL

SCREPNQHFKPYLKHFLPKRLHFAKSDRIEPLTFYLDPQWQLALNPSERKYCGSGEHGSDNVESNMQ

ALFVGYGPGFKHGIEADTFENIEVYNLMCDLLNLTPAPNNGTHGSLNHLLKNPVYTPKHPKEVHPLV

QCPFTRNPRDNLGCSCNPSILPIEDFQTQFNLTVAEEKIIKHETLPYGRPRVLQKENTICLLSQHQF

MSGYSQDILMPLWTSYTVDRNDSFSTEDFSNCLYQDFRIPLSPVHKCSFYKNNTKVSYGFLSPPQLN

KNSSGIYSEALLTTNIVPMYQSFQVIWRYFHDTLLRKYAEERNGVNVVSGPVFDFDYDGRCDSLENL

RQKRRVIRNQEILIPTHFFIVLTSCKDTSQTPLHCENLDTLAFILPHRTDNSESCVHGKHDSSWVEE

LLMLHRARITDVEHITGLSFYQQRKEPVSDILKLKTHLPTFSQEDRSGSGGSMKWVTFLLLLEVSGS

AFSRGVFRREAHKSEIAHRYNDLGEQHFKGLVLIAFSQYLQKCSYDEHAKLVQEVTDFAKTCVADES

AANCDKSLHTLFGDKLCAIPNLRENYGELADCCTKQEPERNECFLQHKDDNPSLPPFERPEAEAMCT

SFKENPTTFMGHYLHEVARRHPYFYAPELLYYAEQYNEILTQCCAEADKESCLTPKLDGVKEKALVS

SVRQRMKCSSMQKFGERAFKAWAVARLSQTFPNADFAEITKLATDLTKVNKECCHGDLLECADDRAE

LAKYMCENQATISSKLQTCCDKPLLKKAHCLSEVEHDTMPADLPAIAADFVEDQEVCKNYAEAKDVF

LGTFLYEYSRRHPDYSVSLLLRLAKKYEATLEKCCAEANPPACYGTVLAEFQPLVEEPKNLVKTNCD

LYEKLGEYGFQNAILVRYTQKAPQVSTPTLVEAARNLGRVGTKCCTLPEDQRLPCVEDYLSAILNRV

CLLHEKTPVSEHVTKCCSGSLVERRPCFSALTVDETYVPKEFKAETFTFHSDICTLPEKEKQIKKQT

ALAELVKHKPKATAEQLKTVMDDFAQFLDTCCKAADKDTCFSTEGPNLVTRCKDALARSWSHPQFEK

Doubly Underlined: NPP7; Plain Text: NPP1; Bold: spacer sequence; Singly Underlined: albumin (SEQ ID NO: 23)

IISLFTFAVGVNICLGFTA

NPP51 Amino Acid Sequence (SEQ ID NO: 24)

MTSKFLLVSFILAALSLSTIFSLQPSCAKEVKSCKGRCFERTFSNCRCDAACVSLGNCCLDFQETCV

EPTHIWTCNKFRCGEKRLSRFVCSCADDCKTHNDCCINYSSVCQDKKSWVEETCESIDTPECPAEFE

```
SPPTLLFSLDGFRAEYLHTWGGLLPVISKLKNCGTYTKNMRPMYPTKTFPNHYSIVTGLYPESHGII

DNKMYDPKMNASFSLKSKEKENPLWYKGQPIWVTANHQEVKSGTYFWPGSDVEIDGILPDIYKVYNG

SVPFEERILAVLEWLQLPSHERPHFYTLYLEEPDSSGHSHGPVSSEVIKALQKVDRLVGMLMDGLKD

LGLDKCLNLILISDHGMEQGSCKKYVYLNKYLGDVNNVKVVYGPAARLRPTDVPETYYSFNYEALAK

NLSCREPNQHFRPYLKPFLPKRLHFAKSDRIEPLTFYLDPQWQLALNPSERKYCGSGEHGSDNLFSN

MQALFIGYGPAFKHGAEVDSFENIEVYNLMCDLLGLIPAPNNGSHGSLNHLLKKPIYNPSHPKEEGF

LSQCPIKSTSNDLGCTCDPWIVPIKDFEKQLNLTTEDVDDIYHMTVPYGRPRILLKQHRVCLLQQQQ

FLTGYSLDLLMPLWASYTFLSNDQFSRDDFSNCLYQDLRIPLSPVHKCSYYKSNSKLSYGFLTPPRL

NRVSNHIYSEALLTSNIVPMYQSFQVIWHYLHDTLLQRYAHERNGINVVSGPVFDFDYDGRYDSLEI

LKQNSRVIRSQEILIPTHFFIVLTSCKQLSETPLECSALESSAYILPHRPDNIESCTHGKRESSWVE

ELLTLHRARVTDVELITGLSFYQDRQESVSELLRLKTHLPIFSQED
```
Underlined: NPP5; Plain: NPP1

NPP51-ALB Amino Acid Sequence
(SEQ ID NO: 25)
```
MTSKELLVSFILAALSLSTIFSLQPSCAKEVKSCKGRCFERTFSNCRCDAACVSLGNCCLDFQETCV

EPTHIWTCNKFRCGEKRLSRFVCSCADDCKTHNDCCINYSSVCQDKKSWVEETCESIDTPECPAEFE

SPPTLLFSLDGFRAEYLHTWGGLLPVISKLKNCGTYTKNMRPMYPTKTFPNHYSIVTGLYPESHGII

DNKMYDPKMNASFSLKSKEKFNPLWYKGQPIWVTANHQEVKSGTYFWPGSDVEIDGILPDIYKVYNG

SVPFEERILAVLEWLQLPSHERPHFYTLYLEEPDSSGHSHGPVSSEVIKALQKVDRLVGMLMDGLKD

LGLDKCLNLILISDHGMEQGSCKKYVYLNKYLGDVNNVKVVYGPAARLRPTDVPETYYSFNYEALAK

NLSCREPNQHFRPYLKPFLPKRLHFAKSDRIEPLTFYLDPQWQLALNPSERKYCGSGEHGSDNLFSN

MQALFIGYGPAFKHGAEVDSFENIEVYNLMCDLLGLIPAPNNGSHGSLNHLLKKPIYNPSHPKEEGF

LSQCPIKSTSNDLGCTCDPWIVPIKDFEKQLNLTTEDVDDIYHMTVPYGRPRILLKQHRVCLLQQQQ

FLTGYSLDLLMPLWASYTFLSNDQFSRDDFSNCLYQDLRIPLSPVHKCSYYKSNSKLSYGFLTPPRL

NRVSNHIYSEALLTSNIVPMYQSFQVIWHYLHDTLLQRYAHERNGINVVSGPVFDFDYDGRYDSLEI

LKQNSRVIRSQEILIPTHFFIVLTSCKQLSETPLECSALESSAYILPHRPDNIESCTHGKRESSWVE

ELLTLHRARVTDVELITGLSFYQDRQESVSELLRLKTHLPIFSQEDGGSGGSMKWVTFLLLLFVSGS

AFSRGVFRREAHKSEIAHRYNDLGEQHFKGLVLIAFSQYLQKCSYDEHAKLVQEVTDFAKTCVADES

AANCDKSLHTLFGDKLCAIPNLRENYGELADCCTKQEPERNECFLQHKDDNPSLPPFERPEAEAMCT

SFKENPTTFMGHYLHEVARRHPYFYAPELLYYAEQYNEILTQCCAEADKESCLTPKLDGVKEKALVS

SVRQRMKCSSMQKFGERAFKAWAVARLSQTFPNADFAEITKLATDLTKVNKECCHGDLLECADDRAE

LAKYMCENQATISSKLQTCCDKPLLKKAHCLSEVEHDTMPADLPAIAADFVEDQEVCKNYAEAKDVF

LGTFLYEYSRRHPDYSVSLLLRLAKKYEATLEKCCAEANPPACYGTVLAEFQPLVEEPKNLVKTNCD

LYEKLGEYGFQNAILVRYTQKAPQVSTPTLVEAARNLGRVGTKCCTLPEDQRLPCVEDYLSAILNRV

CLLHEKTPVSEHVTKCCSGSLVERRPCFSALTVDETYVPKEFKAETFTFHSDICTLPEKEKQIKKQT

ALAELVKHKPKATAEQLKTVMDDFAQFLDTCCKAADKDTCFSTEGPNLVTRCKDALARSWSHPQFEK
```
Doubly Underlined: NPP5; Plain: NPP1; Bold: Spacer; Singly Underlined: Albumin Human IgG Fc domain, Fc
(SEQ ID NO: 26)
```
DKTHTCPPCPAPELLGGPSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVDKSRWQQGN
```

-continued

```
VFSCSVMHEALHNHYTQKSLSLSPGK

ALB
                                                              (SEQ ID NO: 27)
MKWVTFLLLLEVSGSAFSRGVERREAHKSEIAHRYNDLGEQHFKGLVLIAFSQYLQKCSYDEHAKLV

QEVTDFAKTCVADESAANCDKSLHTLFGDKLCAIPNLRENYGELADCCTKQEPERNECFLQHKDDNP

SLPPFERPEAEAMCTSFKENPTTFMGHYLHEVARRHPYFYAPELLYYAEQYNEILTQCCAEADKESC

LTPKLDGVKEKALVSSVRQRMKCSSMQKFGERAFKAWAVARLSQTFPNADFAEITKLATDLTKVNKE

CCHGDLLECADDRAELAKYMCENQATISSKLQTCCDKPLLKKAHCLSEVEHDTMPADLPAIAADFVE

DQEVCKNYAEAKDVFLGTFLYEYSRRHPDYSVSLLLRLAKKYEATLEKCCAEANPPACYGTVLAEFQ

PLVEEPKNLVKTNCDLYEKLGEYGFQNAILVRYTQKAPQVSTPTLVEAARNLGRVGTKCCTLPEDQR

LPCVEDYLSAILNRVCLLHEKTPVSEHVTKCCSGSLVERRPCFSALTVDETYVPKEFKAETFTFHSD

ICTLPEKEKQIKKQTALAELVKHKPKATAEQLKTVMDDFAQFLDTCCKAADKDTCFSTEGPNLVTRC

KDALARSWSHPQFEK (SEQ ID NO: 28)
LIN (SEQ ID NO: 29)
GGSGGS (SEQ ID NO: 30)
RSGSGGS
```

Example 1: ENPP1-asj PXE Mouse Model

Certain polypeptides of the invention (such as ENPP1-Fc) were tested in mouse models of PXE and osteoarthritis (OA). The PXE mice present the loss of function mutation in the multi-pass membrane transporter ABCC6, in a similar fashion to humans with PXE. ANK mice were used as a mammalian model for OA.

Heterozygous ENPP1-asj/+ breeding pairs were maintained on the "acceleration diet" (TD00.442, Harlan Laboratories, Madison Wis.) throughout the entire experiment to generate ENPP1-WT and ENPP1-asj/asj sibling pairs that had been exposed to the acceleration diet in utero. Liters were genotyped on day 8 and weaned at day 21. Following weaning, sibling pairs were divided into experimental cohorts and all experimental animals were maintained on the acceleration diet through completion of the study. Selected polypeptides of the invention were administered to study animals, as described herein, and bones are analyzed.

Figure 7:
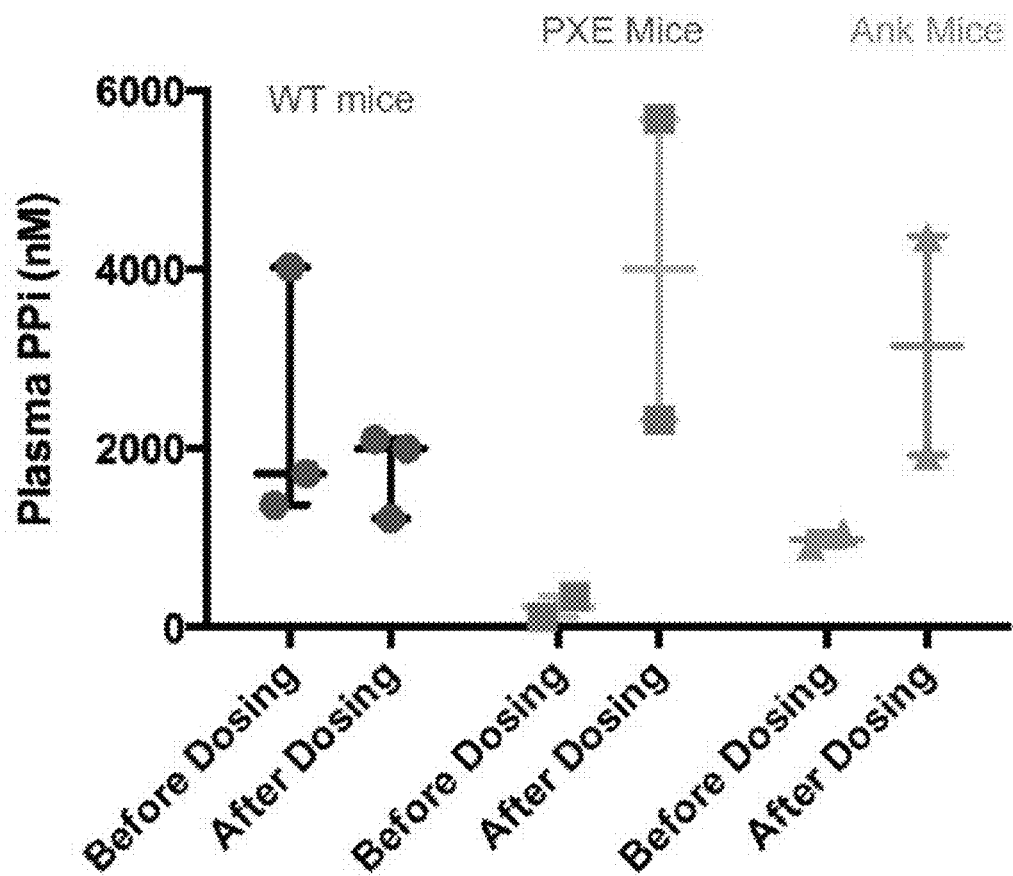
FIG. 7 is a graph illustrating measured plasma PPi levels in mice treated with ENPP1-Fc as described in Example 1.
Figure 8:
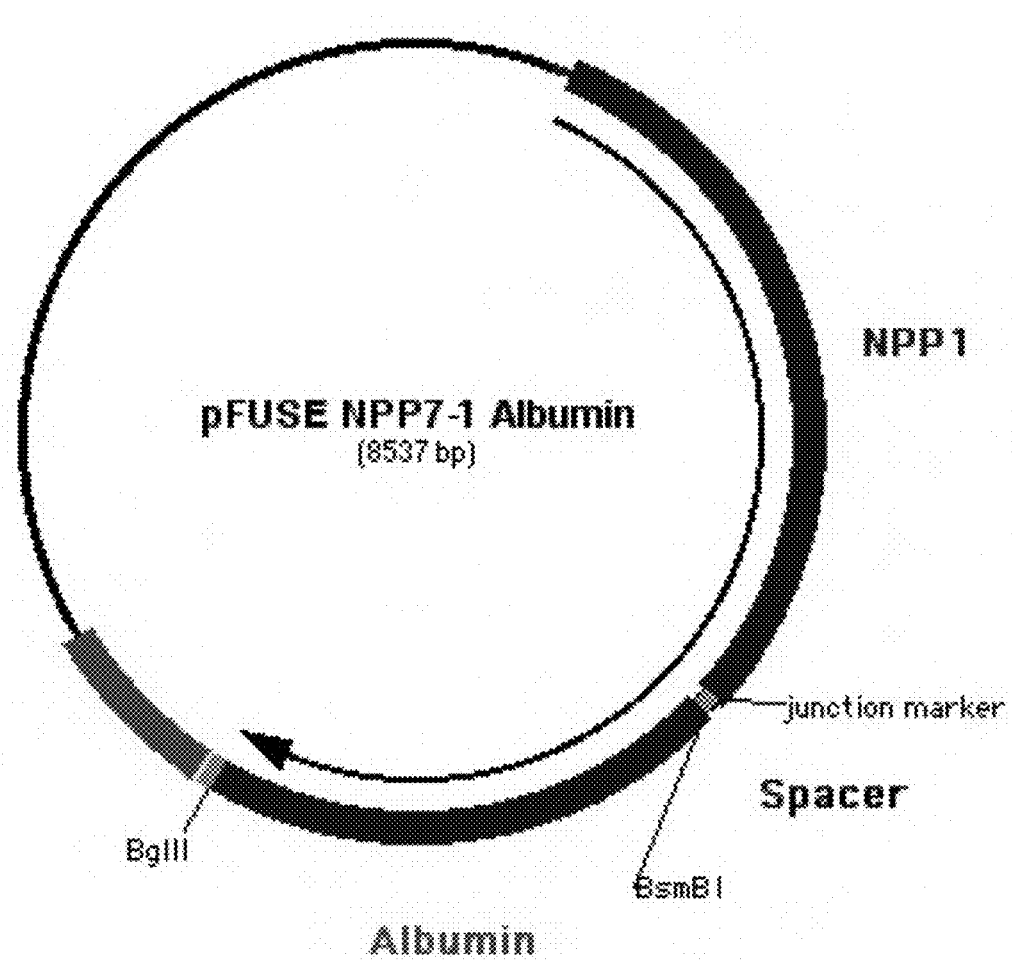
FIG. 8 is a schematic illustration of a plasmid used to express SEQ ID NO:22.
Figure 9:
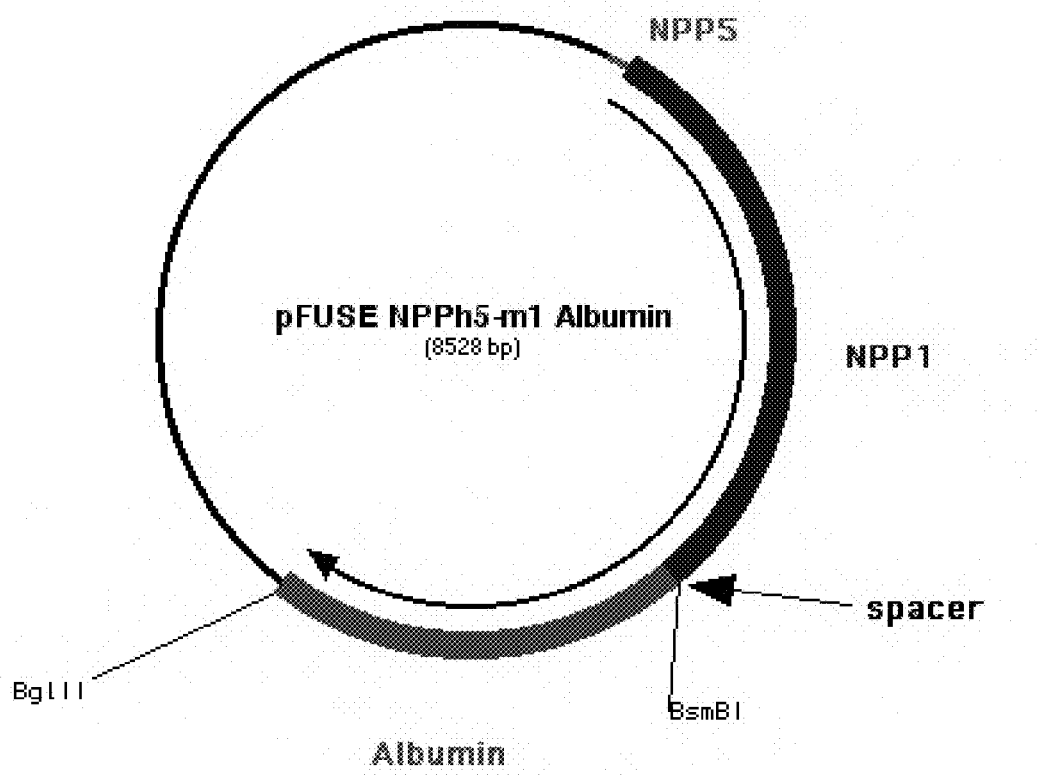
FIG. 9 is a schematic illustration of a plasmid used to express SEQ ID NO:25.

As illustrated in FIG. 7, both PXE and ANK mice initially have low PPi, a biomarker that is reported in the literature to account for the pathogenesis of PXE (Jansen, et al., 2014, Arterioscler. Thromb. Vasc. Biol. 34:1985-1989).

Two PXE mice were dosed for one week with ENPP1-Fc, and the mean plasma PPi in these animals increased to about 4 µM. This indicates that administration of the polypeptides of the invention to mammals raises their extracellular levels of PPi and treats PXE.

The polypeptide's ability to elevate PPi was not expected, because the biological mechanism for low PPi was thought to be associated with low ATP concentrations (Jansen, et al., 2013, PNAS USA 110(50):20206-20211). In fact, it was proposed in the prior art that correction of plasma PPi in PXE is sufficient to treat the disease (Jansen, et al., 2013, PNAS USA 110(50):20206-20211). Based on the prior art at the time of the invention, one skilled in the art would contemplate that ENPP1 enzyme is not able to generate PPi in the setting of PXE due to lack of sufficient substrate in the extracellular space. As demonstrated herein, this is clearly not the case.

Example 2

Figure 1D:
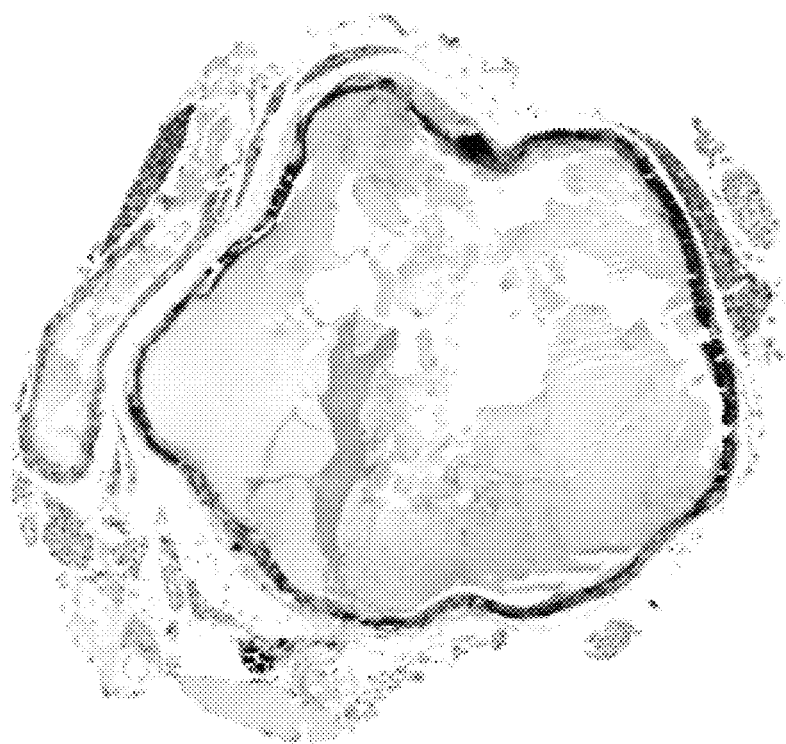
Figure 1E:
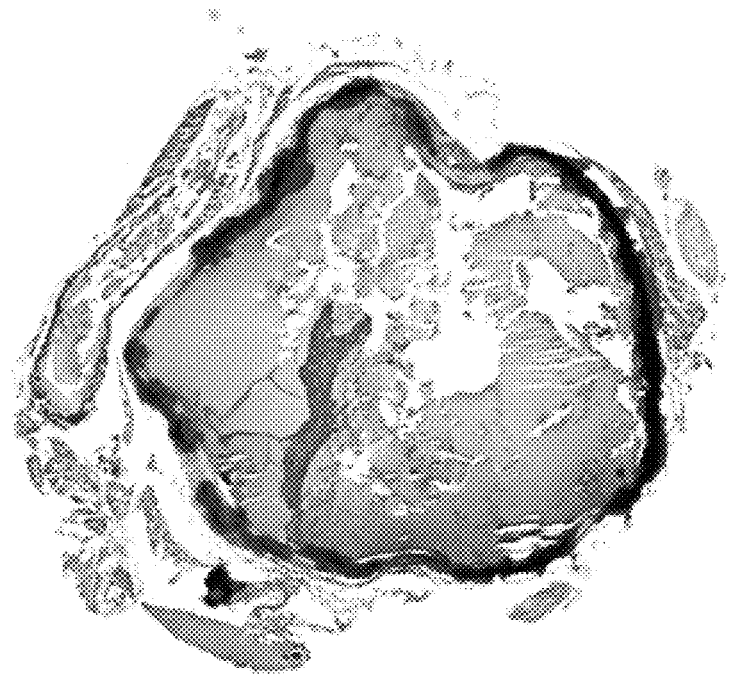
Figure 1F:
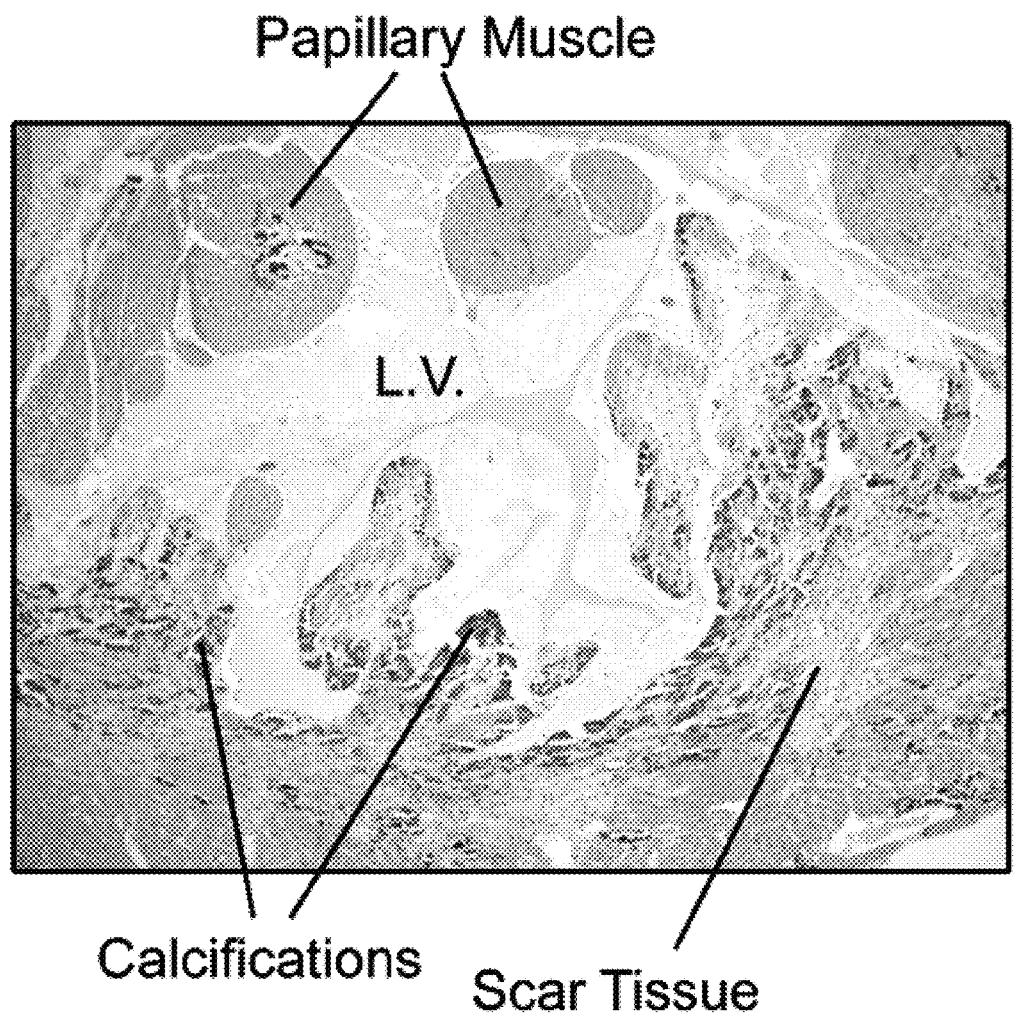
Figure 1G:
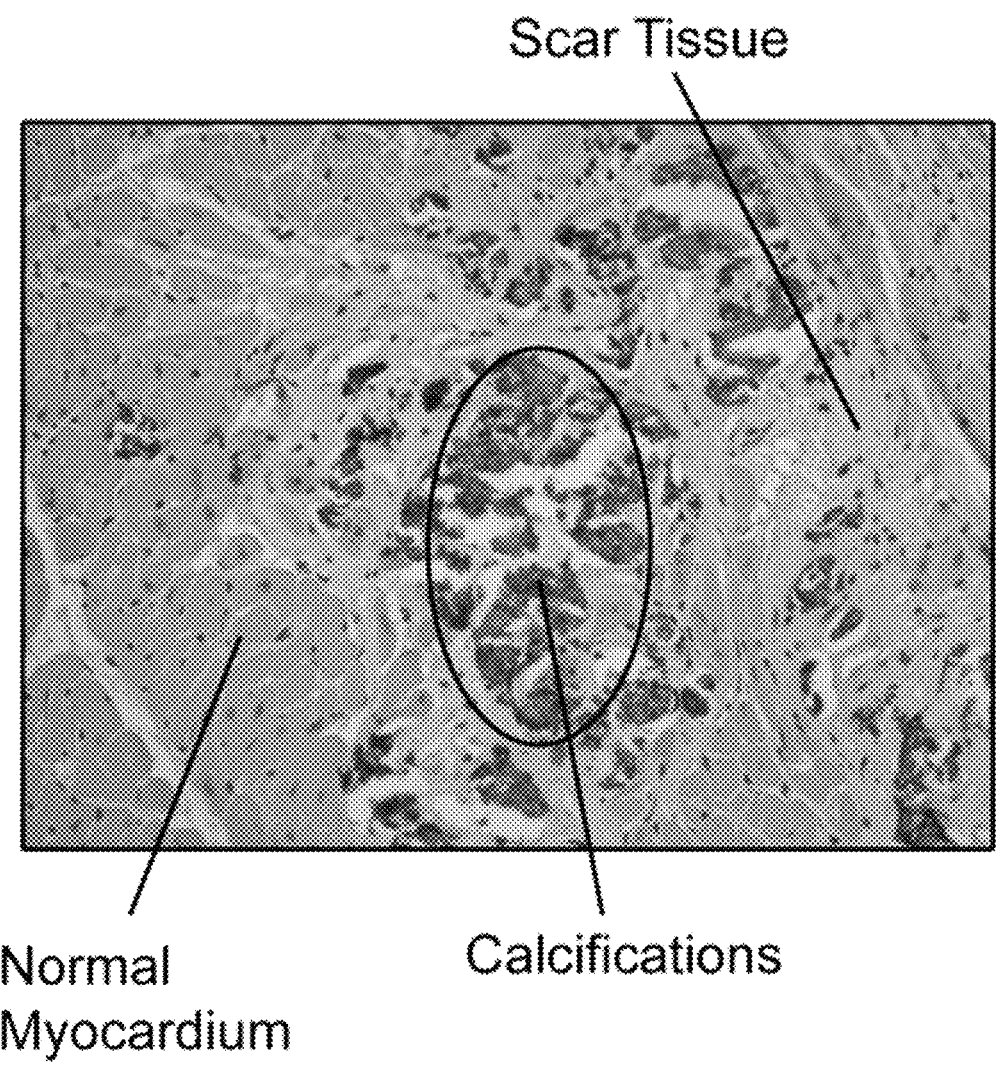

When fed an acceleration diet, the daily weights of ENPP1-asj/asj mice diverged from WT siblings pairs at day 26, when the ENPP1-asj/asj mice experienced a "failure to thrive" event and began to lose weight (FIG. 1A). After day 26 the ENPP1-asj/asj animals displayed progressive stiffness and reductions in physical activity. All of the ENPP1-asj/asj animals died between days 35-71, with a median lifespan of 58 days (FIG. 1G). The presence of calcifications in ENPP1-asj/asj and ENPP1-WT mice was evaluated post mortem by micro-CT scans and histologic sections taken from the heart, aorta, and kidneys. Approximately one-third of the ENPP1-asj/asj mice had visible calcifications in their hearts, and two-thirds had visible calcifications in their aortas, by micro-CT imaging (Table 2). These percentages increased to 100% upon histologic examination, which also showed that many of the animals had dramatic nearly circumferential calcifications in their aortic walls (FIGS. 1D-1E). Histologic examination also revealed that 100% of the coronary arteries possessed arterial wall calcifications, and that 70% of the animals had focal or confluent areas of myocardial necrosis consistent with myocardial infarction (FIGS. 1F-1G). Conversely, the ENPP1-WT mice displayed none of these abnormalities. These findings demonstrate that the animal model recapitulates GACI in humans, which is characterized by prominent calcifications of the large and medium sized arteries and a cardiac demise.

Figure 2A:
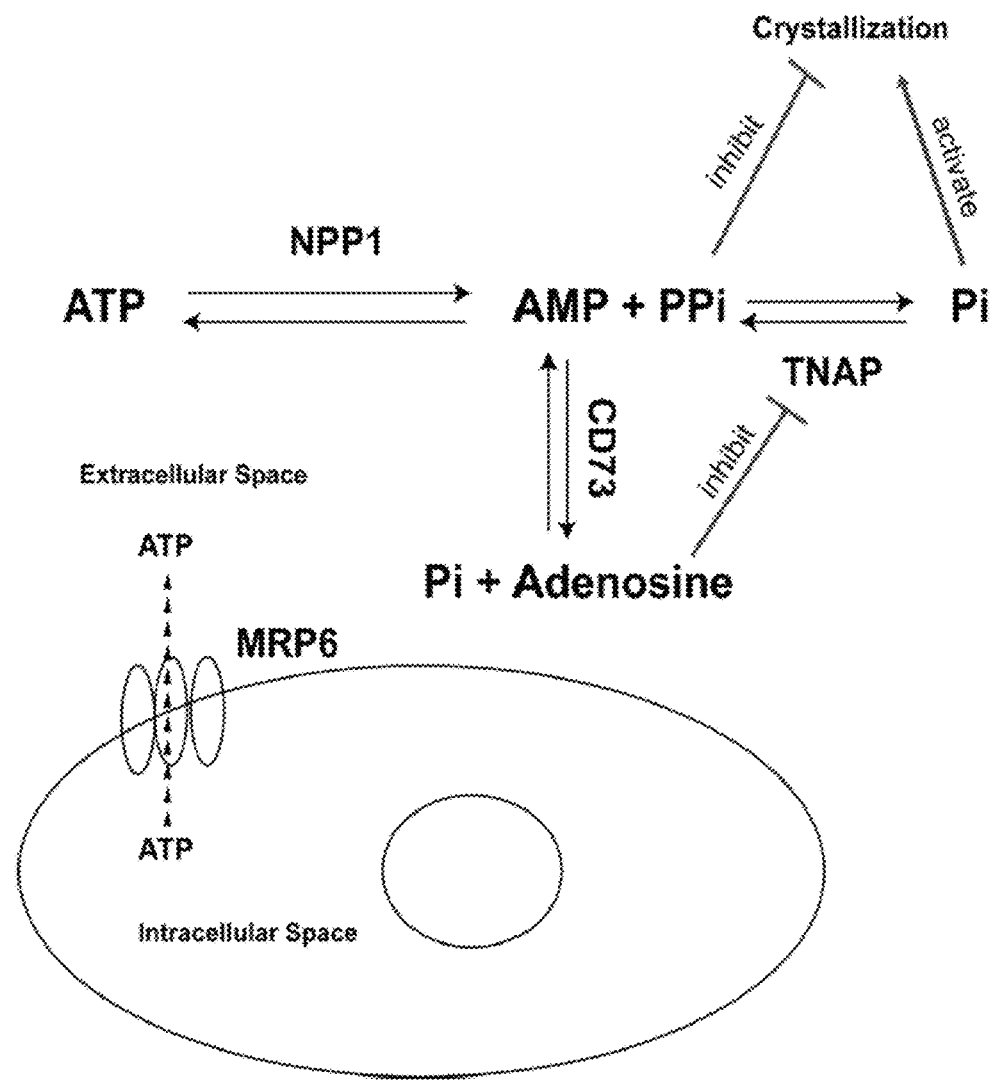
Figure 2D:
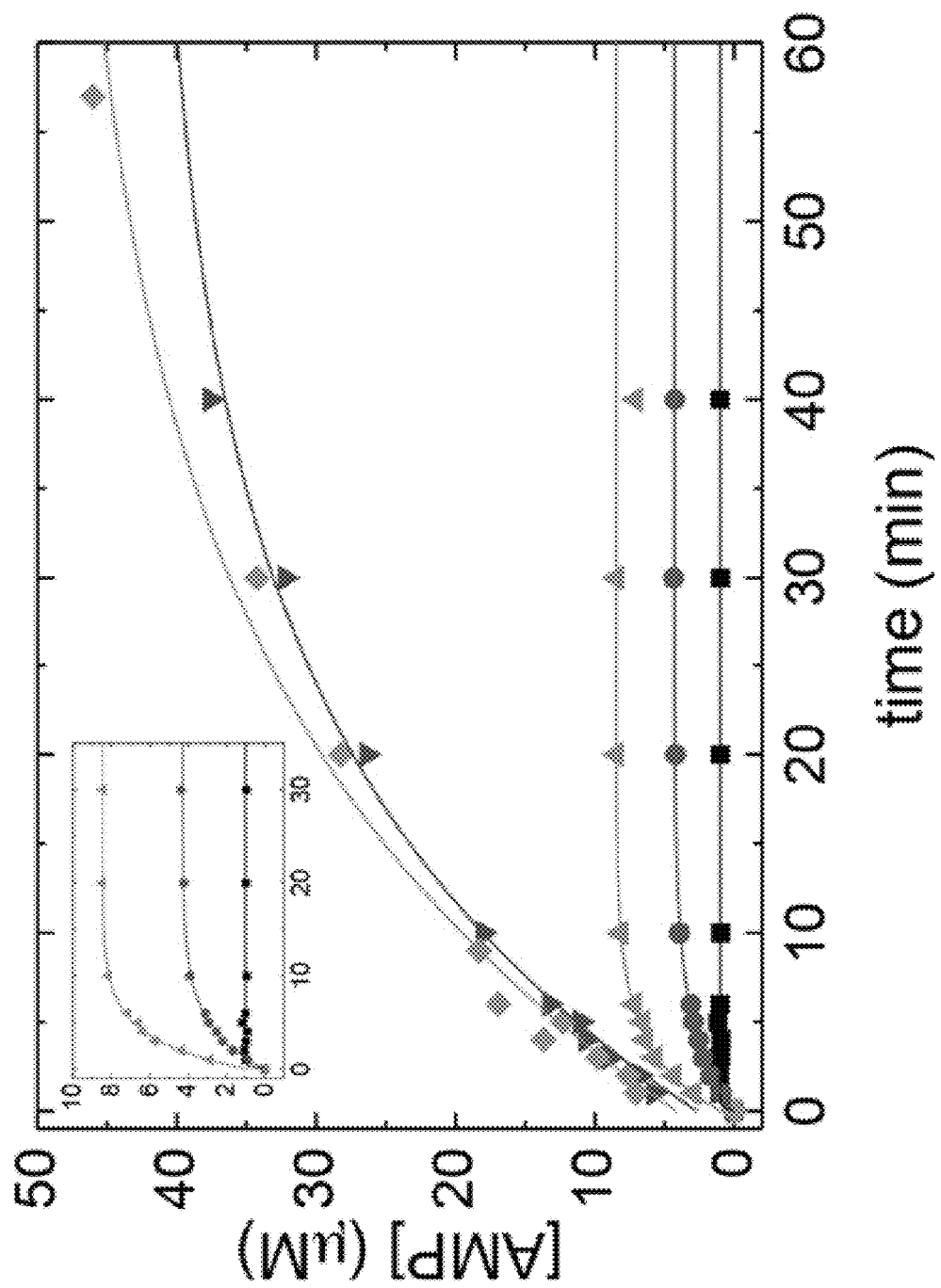
Figure 2E:
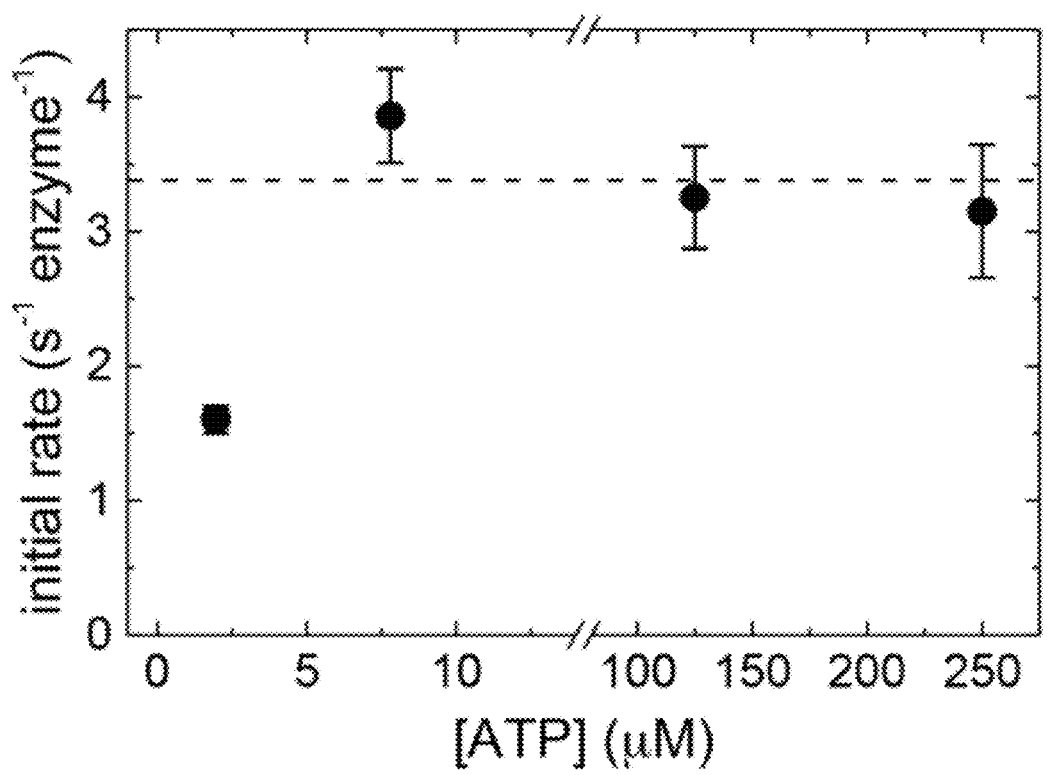

To produce soluble, recombinant ENPP1 for in vivo use, ENPP1 was fused to the Fc domain of IgG1 (hereafter referred to as ENPP1-Fc, FIG. 2B) and the fusion protein was expressed in stable mammalian (HEK293) cell lines. The combined effect of switching protein expression from insect cells to mammalian cells and fusion of ENPP1 to the Fc domain of IgG1 altered the Michaelis Menton kinetics by increasing the affinity of ENPP1 for ATP substrate by over two orders of magnitude, while also reducing the $K_{cat}$ by a factor of 3-4 (FIGS. 2C-2E). The activity of ENPP1-Fc was noted to diminish over a 30 day period when stored at 4° C. but the enzyme could be frozen at −80° C. and retain nearly complete activity upon thawing (FIG. 2C). The enzyme was therefore stored as a frozen stock solution after purification until needed.

Following purification, ENPP1-Fc was dialyzed into PBS supplemented with Zn and Mg ($PBS_{plus}$) concentrated to between 5 and 7 mg/ml, and frozen at −80° C. in aliquots of 200-500 µl. Aliquots were thawed immediately prior to use and the specific activity of the solution was adjusted to 31.25 au/ml (or about 0.7 mg/ml depending on the preparation) by dilution in $PBS_{plus}$.

Dosing was performed according to activity units (au) per Kg animal weight to account for variations in specific activity in different protein preparations. The specific activity of the enzyme varied with each protein preparation, and because the clinical response was noted to be highly dependent on enzyme specific activity, protein preparations with specific activities of less than 40 au/mg were rejected. To establish initial dosing levels for the proof of concept study, dose escalation trials were performed in limited numbers of animals (1-2 per dose level). While both the human and mouse version ENPP1 was used in the dose escalation trials, the proof of concept study was performed with the mouse isoform of ENPP1-Fc (mENPP1-Fc). ENPP1-asj/asj mice were dosed daily on the $14^{th}$ day of life with subcutaneous injections of mENPP1-Fc and weekly with intra-peritoneal (I.P.) injections of GK 1.5, the latter added to minimize immune rejection of recombinant protein. Subcutaneous doses of mEnpp1-Fc at 500 au/Kg qD demonstrated a strong early response in weight with an absence of the observed "failure to thrive" crisis observed in undosed ENPP1-asj/asj animals.

Figure 3B:
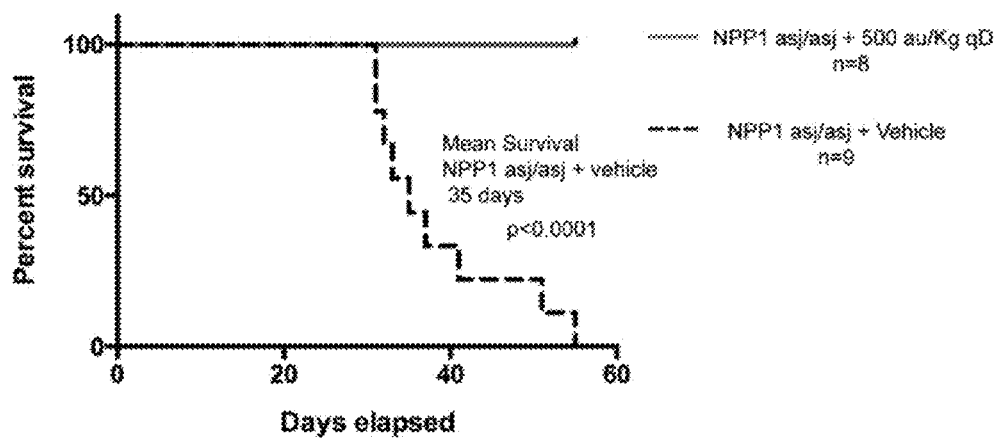
Figure 3C:
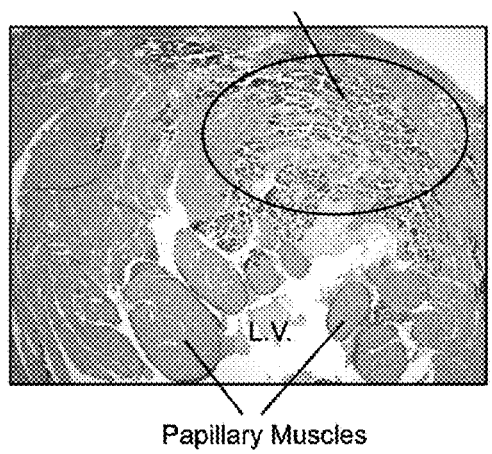
Figure 3D:
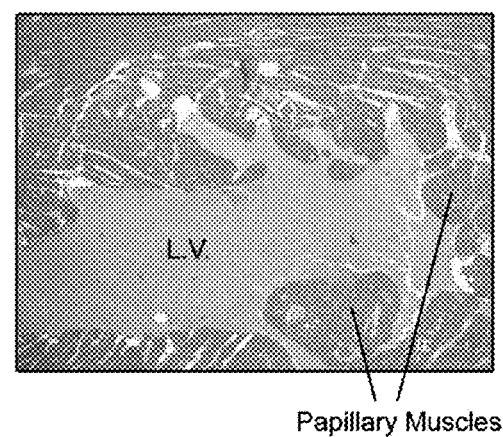

Based on the results of the dose escalation trials, a cohort of 8 NPP1-asj/asj animals was dosed with mNPP1-Fc at 500 au/Kg qD and weekly IP injections with GK1.5 (FIG. 3). A control group (NPP1-WT+vehicle and NPP1-asj/asj+vehicle) was dosed daily with vehicle and weekly with GK1.5 in an identical manner as the dosed cohort, and the study duration was shortened to 55 days. All 8 treated ENPP1-asj/asj animals survived the full 55 days of the trial, with a dramatic clinical response observed in treated, while the median life span of the untreated NPP1 asj/asj animals decreased from 58 days to 37 days in the therapeutic trial, perhaps resulting from the weekly IP injections of the GK1.5 immunosuppressive. The untreated ENPP1-asj/asj animals also all experienced a failure to thrive crisis day 26, characterized by weight loss and mobility restriction progressing variably to paralysis and death over the next 30 days. All but one untreated ENPP1-asj/asj animal expired over the 55 day trial, while in contrast all treated ENPP1-asj/asj mice gained weight comparable to the ENPP1-WT mice and displayed no signs of reduced mobility or stiffness.

Figure 4D:
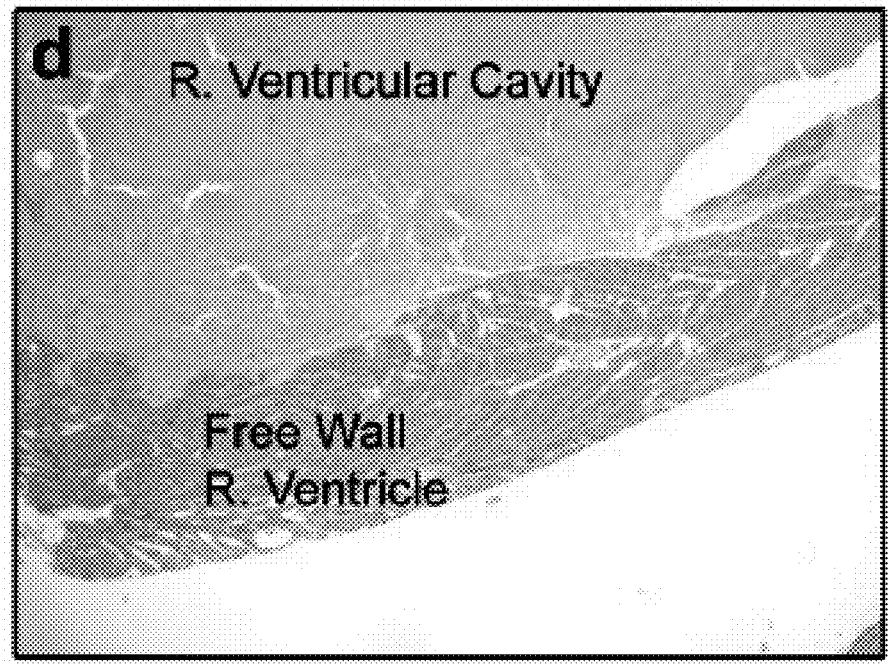
Figure 4E:
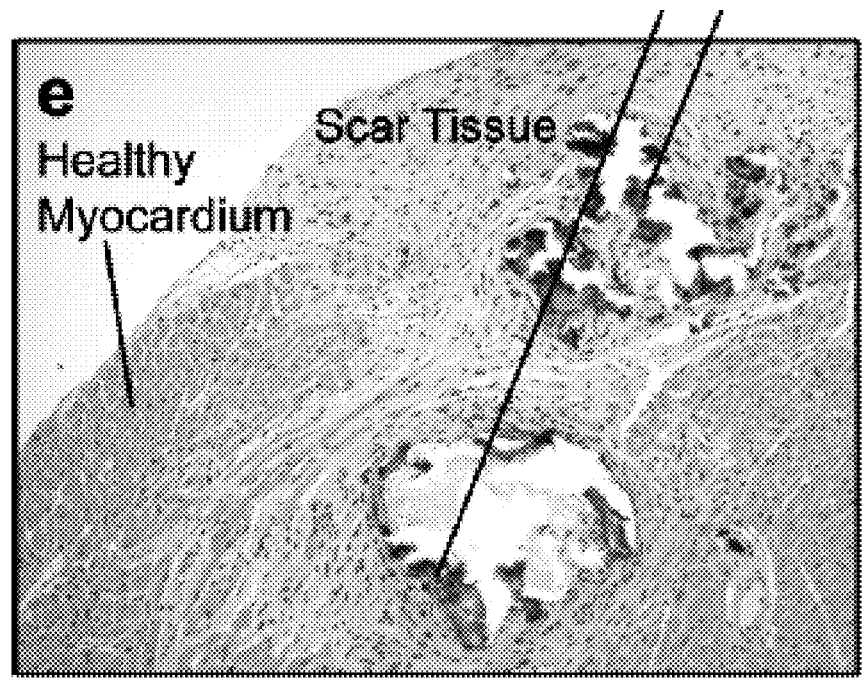
Figure 4F:
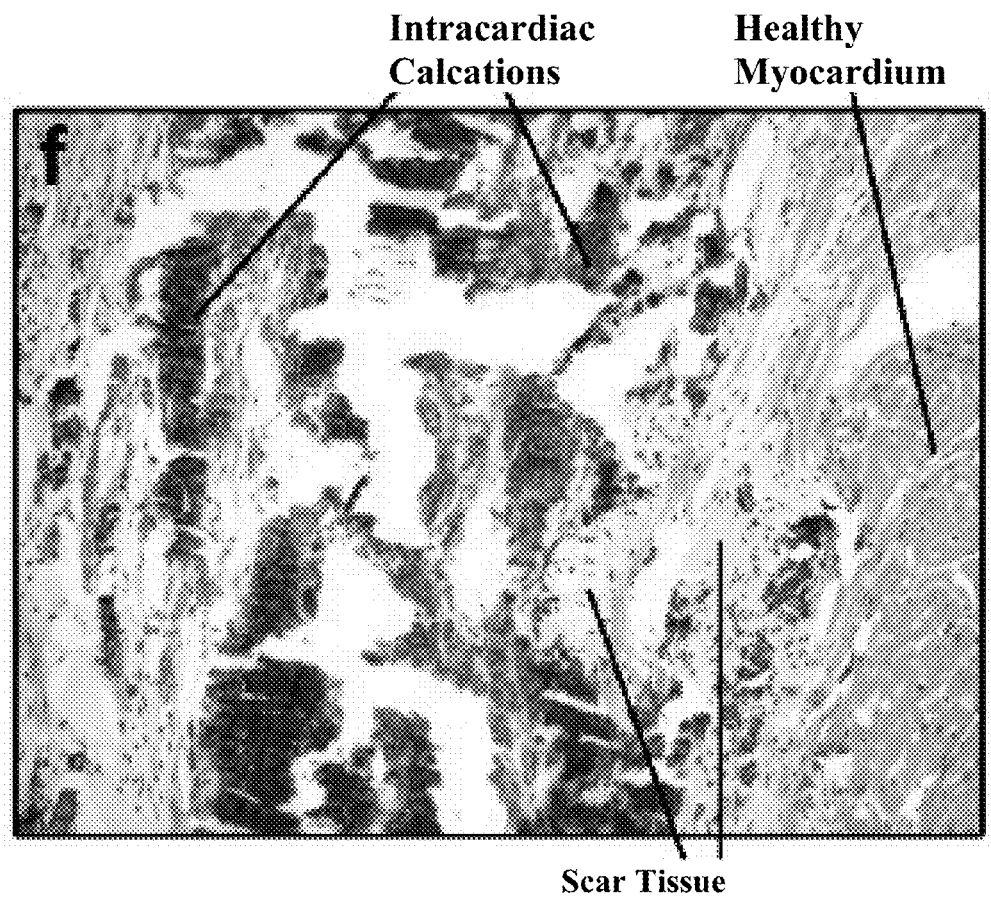
Figure 4G:
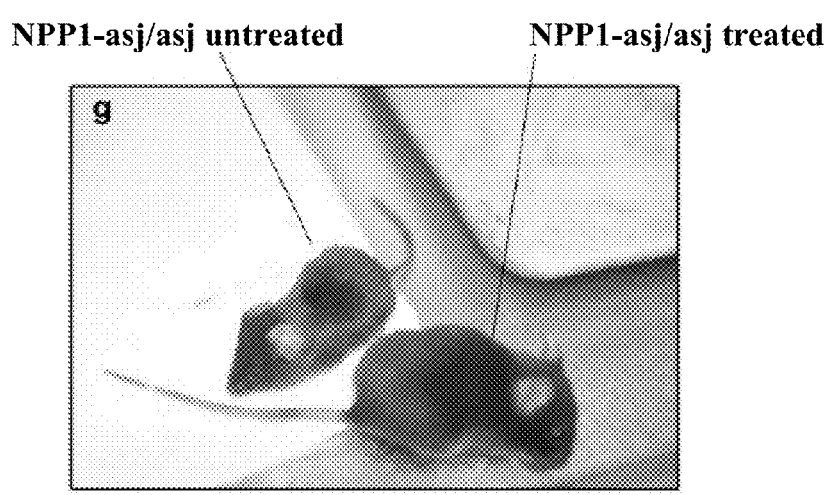

At the conclusion of the study, 100% of the ENPP1-asj/asj mice treated with vehicle displayed calcifications in their hearts, aortas, and coronary arteries, and 77% of the animals displayed histologic evidence of myocardial infraction (Table 1). In most cases this took the form of small areas of myocardial cell necrosis and drop out in the vicinity of the cardiac calcifications (FIGS. 3C-3D, FIGS. 4C-4E), but in two animals (22%) there were large, full thickness myocardial infarctions in the free wall of the right ventricle (FIGS. 4C-4D). Myocardial fibrosis in myocardial tissue adjacent to coronary artery calcifications was a common finding (FIG. 4E), illustrating that ischemia from coronary artery calcification likely accounts for the myocardial disease. In contrast, none of the ENPP1-asj/asj animals treated with ENPP1-Fc displayed cardiac, arterial, or aortic calcification on histology or post-mortem micro-CT (Table 1, and FIGS. 3D and 4D).

In addition to survival, daily animal weights, and terminal histology, treatment response was also assessed via post-mortem high resolution micro-CT scans to image vascular calcifications, plasma [PPi] concentrations, and Tc99 PPi ($^{99m}$PYP) uptake (FIG. 5 and Table 1). The biochemical and physiologic response was complete as measured by all of these parameters. None of the WT or treated ENPP1-asj/asj animals were noted to possess any vascular calcifications via micro-CT, in contrast to the dramatic calcifications noted in the aortas, coronary arteries, and hearts of the untreated ENPP1-asj/asj cohort (FIG. 5A. In addition, serum PPi concentrations of treated ENPP1-asj/asj animals were elevated above WT animals (about 30 µM in the treated ENPP1-asj/asj vs. about 10 µM in WT), and well above untreated ENPP1-asj/asj levels (<0.5 µM) (FIG. 5B). In addition, serum PPi concentrations of treated ENPP1-asj/asj animals (about 30 µM) were elevated well above untreated ENPP1-asj/asj levels (<0.5 µM), and above that of WT animals (about 10 µM) (FIG. 5B).

Figure 5A:
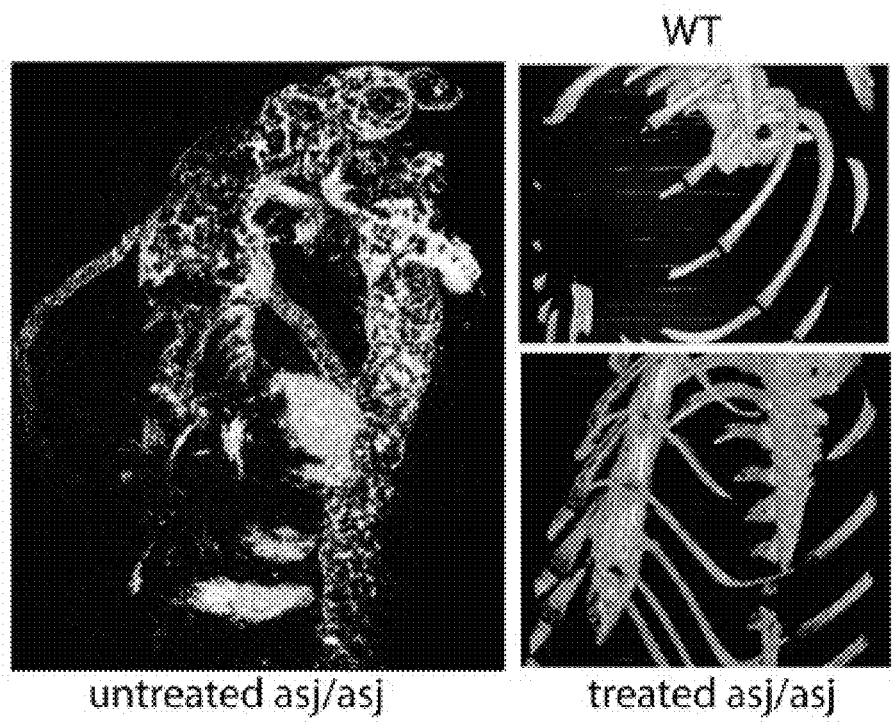
FIGS. 5A-5F comprise a set of images and graphs illustrating biomarkers of disease response.
Figure 5B:
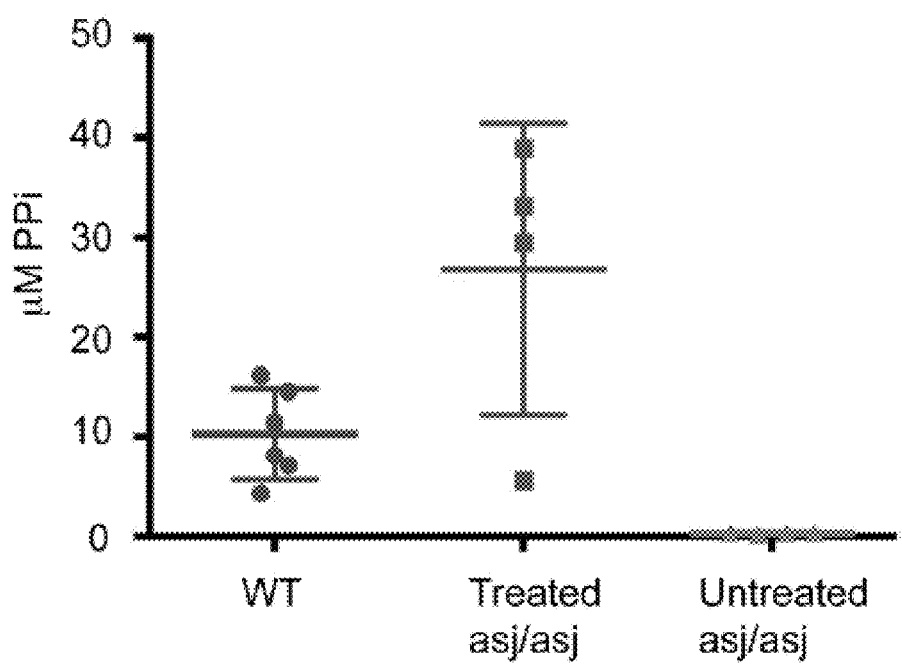
Figure 5C:
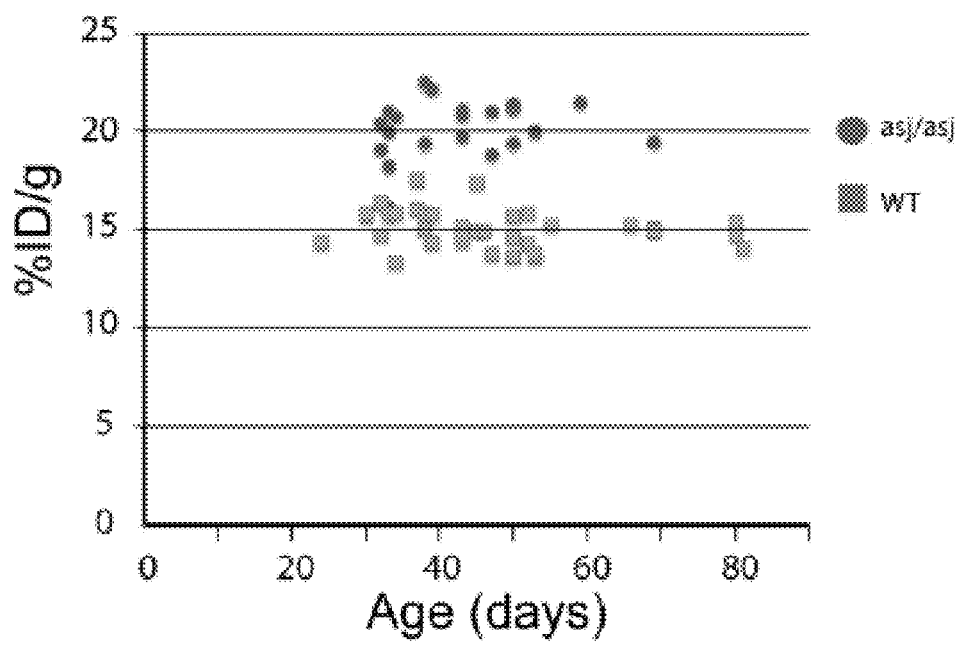
Figure 5D:
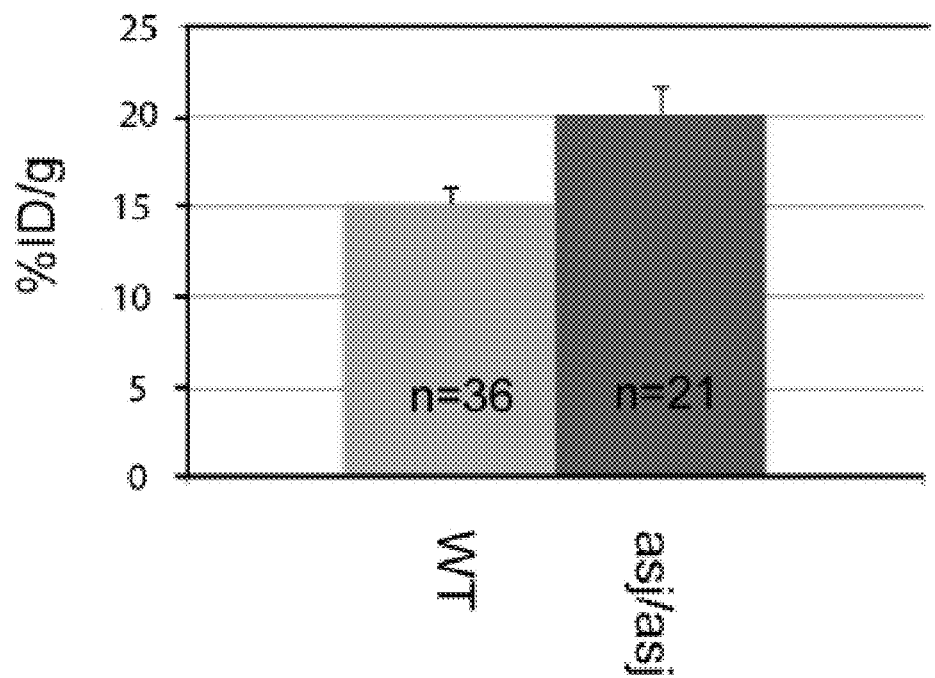
Figure 5E:
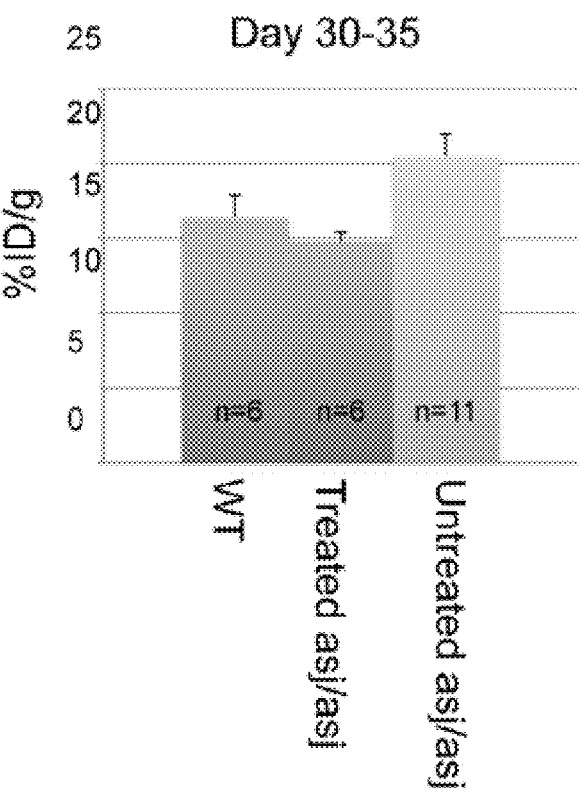
Figure 5F:
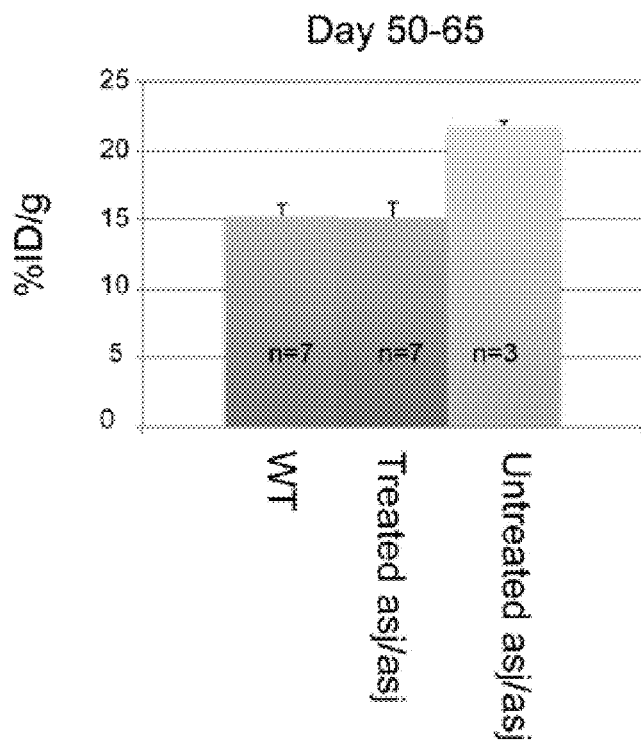
Figure 6:
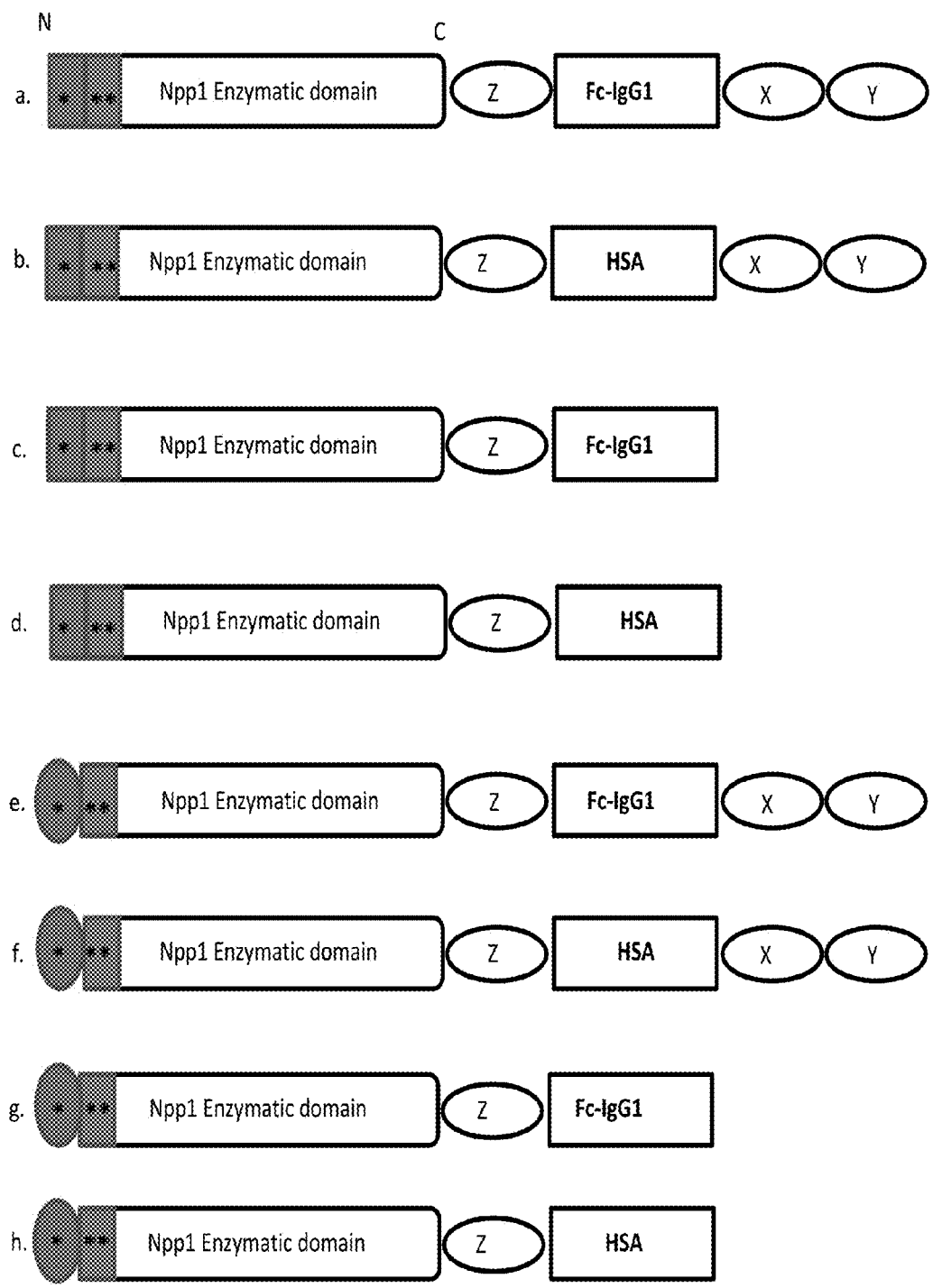
FIG. 6, comprising panels a-h, illustrates certain non-limiting constructs of NPP1 fusion proteins. X and Y are optional peptides in some embodiments. Z is an optional linker that connects either Fc domain or HSA domain to the C terminus of NPP1 protein. The N and C terminal regions of NPP1 protein are depicted as N and C in FIG. 6. Panels a-d illustrate fusion proteins comprising transmembrane domain of NPP2 (marked as '*') and NPP1 (marked as '**') along with NPP1 enzymatic domain. The enzymatic domain of NPP1 begins as PSCAKE amino acid sequence and ends at QED amino acid sequence. Panels e-h illustrate fusion proteins comprising signal peptide of NPP2 (marked as '*') and transmembrane domain of NPP1 (marked as '**') along with NPP1 enzymatic domain.

$^{99m}$PYP, an imaging agent typically employed in cardiac imaging and bone remodeling, was used as a marker for treatment response because one would expect that $^{99m}$PYP uptake in animals lacking functional ENPP1 should be increased as they would be expected to have reduce plasma [PPi] and more 'open' PPi binding sites at sites of ectopic mineralization. To test this hypothesis, in vivo $^{99m}$PYP imaging was performed weekly in ENPP1-WT and undosed ENPP1-asj/asj animals to detect differences in PYP uptake between the sibling pairs (FIGS. 5C-5D). Analysis of $^{99m}$PYP uptake was limited to the head, which is comprised of both enchondral bone (skull) and soft tissue (vibrissae), which are known sites of ectopic calcification in mouse models of this GACI. In addition, the analysis was limited to the head to simplify data collection, as the head does not overlap with internal organs showing transient $^{99m}$PYP uptake (such as the bladder, heart, and diaphragm) during the 180° camera rotation that occurs during data collection.

Weekly serial imaging of ENPP1-WT and untreated ENPP1-asj/asj animals demonstrated that the percent uptake of the injected dose of $^{99m}$PYP in skulls was greater in ENPP1-asj/asj animals than in ENPP1-WT animals and changes in $^{99m}$PYP uptake within experimental groups did not vary significantly over the course of the study (FIGS. 5C-5D). $^{99m}$PYP Uptake in treated and untreated ENPP1-asj/asj animals was compared at two time points—days 30-35 and at the completion of the study (days 50-65). Comparison of these experimental groups demonstrates that ENPP1-Fc treatment returned $^{99m}$PYP uptake in GACI mice to WT levels (FIGS. 5E-5F), suggesting that ENPP1-Fc treatment is able to abrogate unregulated tissue and skull mineralization in ENPP1-asj/asj mice by saturating open PPi binding sites with 'cold' PPi, which presumably originates from increased plasma PPi concentrations induced by the therapeutic.

TABLE 1

Cardiovascular Pathology, Proof of Concept Study

| | WT + Vehicle | asj/asj + vehicle | asj/asj + mENPP1-Fc |
|---|---|---|---|
| Calcifications Heart (CT/Histology) | 0/0 | 55%/100% | 0/0 |
| Calcifications Aorta (CT/Histology) | 0/0 | 66%/100% | 0/0 |
| Calcifications in Coronary Arteries (CT/histology) | 0/0 | 43%/100% | 0/0 |
| % myocardial infarction (Histology) | 0/0 | 77% | 0 |

TABLE 2

Cardiovascular Pathology, Natural History Study

| | WT | asj/asj |
|---|---|---|
| % Calcifications in heart (CT/histology) | 0/0 | 37%/100% |
| Calcifications in Aorta (CT/histology) | 0/0 | 62%/100% |
| Calcifications in Coronary Arteries (Histology) | 0/0 | 100% |
| % myocardial infarction (Histology) | 0 | 70% |

Example 3: Expression of Albumin Fusion Protein

Human serum albumin (HSA), a protein of 585 amino acids, is responsible for a significant proportion of the osmotic pressure of serum and also functions as a carrier of endogenous and exogenous ligands. At present, HSA for clinical use is produced by extraction from human blood. Production of recombinant HSA (rHSA) in microorganisms has been disclosed in EP 0 330 451 and EP 0 361 991.

The role of albumin as a carrier molecule and its inert nature are desirable properties for use as a stabilizer and transporter of polypeptides. Use of albumin as a component of a fusion protein for stabilizing other proteins has been disclosed in WO 93/15199, WO 93/15200, and EP 0 413 622. The use of N-terminal fragments of HSA for fusions to polypeptides has also been disclosed (EP 0 399 666). Fusion to the polypeptide is achieved by genetic manipulation, such that the DNA coding for HSA, or a fragment thereof, is joined to the DNA coding for the polypeptide. A suitable host is then transformed or transfected with the fused nucleotide sequences, so arranged on a suitable plasmid as to express a fusion polypeptide. Nomura, et al., 1995, Biosci. Biotechnol. Biochem. 59(3):532-4 attempted to express human apolipoprotein E in *S. cerevisae* as a fusion protein with HSA or fragments of HSA, using the HSA pre-sequence to direct secretion. Whilst fusion to full length HSA resulted in the secretion of low levels of the protein into the medium (maximum yield of 6.3 mg per liter), fusion to HSA (1-198) or HSA (1-390) did not result in secretion into the medium.

The human serum albumin may be a variant of normal HSA (termed hereinafter "HSA"). As used herein, "variants" include insertions, deletions and substitutions, either conservative or non-conservative, where such changes do not, substantially alter one or more of the oncotic, useful ligand-binding and non-immunogenic properties of albumin. In particular, "variants" include naturally-occurring polymorphic variants of human albumin and fragments of human albumin, for example those fragments disclosed in EP 0 322 094 (namely HA (1-n), where n is 369 to 419). The albumin or growth hormone (GH) may be from any vertebrate, especially any mammal, for example human, cow, sheep, pig, hen or salmon. The albumin and GH parts of the fusion may be from differing animals.

By "conservative substitutions" is intended swaps within groups such as Gly/Ala; Val/Ile/Leu; Asp/Glu; Asn/Gln; Ser/Thr; Lys/Arg; and Phe/Tyr. The variant usually has at least 75% (such as at least 80%, 90%, 95% or 99%) sequence identity with a length of normal HSA that is the same length as the variant and that is more identical thereto than any other length of normal HSA, once the allowance is made for deletions and insertions as is customary in this art. Generally speaking, an HSA variant is at least 100 amino acids long, in some embodiments at least 150 amino acids long. The HSA variant may consist of or comprise at least one whole domain of HSA, for example domains 1 (1-194), 2 (195-387), 3 (388-585), 1+2 (1-387), 2+3 (195-585) or 1+3 (1-194, +388-585). Each domain is itself made up of two homologous subdomains namely 1-105, 120-194, 195-291, 316-387, 388-491 and 512-585, with flexible inter-subdomain linker regions comprising residues Lys106 to Glu199, Glu292 to Val315 and Glu492 to Ala511. In some embodiments, the HSA part of the NPP1 fusion comprises at least one subdomain or domain of HA or conservative modifications thereof.

Many expression systems are known, including bacteria (for example *E. coli* and *Bacillus subtilis*), yeasts (for example *Saccharomyces cerevisiae, Kluyveromyces lactis* and *Pichia pastoris*), filamentous fungi (for example *Aspergillus*), plant cells, animal cells and insect cells.

The desired protein can be produced in conventional ways, for example from a coding sequence inserted in the host chromosome or on a free plasmid.

The yeasts can be transformed with a coding sequence for the desired protein in any of the usual ways, for example electroporation. Methods for transformation of yeast by electroporation are disclosed in Becker & Guarente, 1990, Methods Enzymol. 194:182. Successfully transformed cells, i.e., cells that contain a DNA construct of the present invention, can be identified by well-known techniques. For example, cells resulting from the introduction of an expression construct can be grown to produce the desired polypeptide. Cells can be harvested and lysed and their DNA content examined for the presence of the DNA using a method, such as that described by Southern, 1975, J. Mol. Biol. 98:503 and/or Berent, et al., 1985, Biotech 3:208. Alternatively, the presence of the protein in the supernatant can be detected using antibodies.

Useful yeast plasmid vectors include pRS403-406 and pRS413-416 and are generally available from Stratagene Cloning Systems, La Jolla, Calif., USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or E. coli DNA polymerase I, which are enzymes that remove protruding, 3'-single-stranded termini with their 3'-5'-exonucleolytic activities, and fill in recessed 3'-ends with their polymerizing activities.

The combination of these activities thus generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA in accordance with the invention, if, for example HA variants are to be prepared, is to use the polymerase chain reaction as disclosed by Saiki, et al., 1988, Science 239:487-491. In this method the DNA to be enzymatically amplified is flanked by two specific oligonucleotide primers that themselves become incorporated into the amplified DNA. The specific primers may contain restriction endonuclease recognition sites which can be used for cloning into expression vectors using methods known in the art.

ENPP1-ALB Design:

Modified, human and mouse NPP1 (Human: NCBI accession NP_006199; Mouse: NCBI accession NP_03839) modified to express soluble, recombinant protein is fused to human serum albumin (HSA) by sub cloning into pFUSE plasmids (InvivoGen, San Diego Calif.), respectively.

Protein Production:

Shaking Flasks:

Stable transfections of the ENPP1-ALB are established in HEK293 cells under zeocin selection, and adherent HEK293 cells can be adapted for suspension growth. Adapted cells are used to seed liquid culture growths in FreeStyle medium (Gibco #12338-018) in shaker flasks at 37° C. and 5% $CO_2$, agitated at 120 rpm with high humidity. The culture is gradually expanded to the desired target volume and then maintained for another 12 days to accumulate extracellular protein. During the maintenance phase, cultures are supplemented with CD EfficientFeed C AGT (Gibco #A13275-05) to enhance protein production.

Bioreactor:

Cells are propagated in a 10 liter bioreactor equipped with dissolved oxygen and pH control. Dissolved oxygen is kept at 40% air saturation by supplying the culture with mixture of air and oxygen not exceeding 3 liter per minute at an agitation rate of 80 RPM. pH ias controlled at 7.4 by sparging $CO_2$ when the pH ise higher than 7.4. Culture growth is followed by measuring cell number, cell viability, glucose and lactate concentrations.

Protein Purification:

The liquid cultures are centrifuged at 4300×g for 15 min and the supernatants are filtered through a 0.2 μm membrane and concentrated via tangential flow using a Pellicon®3 0.11 m2 Ultracell® 30 kD cassette (Millipore, Billerica Mass.). The concentrated supernatant is loaded onto a protein-AG column and can be eluted with a buffer comprising 50 mM Sodium Citrate, 150 mM NaCl, 3 mM $ZnCl_2$, 3 mM $CaCl_2$, pH=3.5. Fractions containing enzymatic activity are pooled and dialyzed against IX PBS buffer pH 7.4, 11 μM $ZnCl_2$, 20 μM $CaCl_2$, then concentrated to 6 mg/ml, distributed into small aliquots and stored at −80° C.

The resulting protein samples are tested with Pierce LAL Chromogenic Endotoxin Quantitation Kit (cat. 88282) to verify that all are free of endotoxin.

Enzymology

The NPP1-albumin fusion protein after purification are characterized following the experimental protocols discussed in Examples 1 and 2, described elsewhere herein.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing or preventing progression of at least one disease selected from the group consisting of chronic kidney disease (CKD), end stage renal disease (ESRD), calcific uremic arteriolopathy (CUA), and calciphylaxis in a subject diagnosed with the at least one disease, the method comprising administering to the subject a therapeutically effective amount of a polypeptide comprising a soluble ecto-nucleotide pyrophosphatase/phosphodiesterase-I (ENPP1) polypeptide, wherein the soluble ENPP1 polypeptide lacks a negatively-charged bone-targeting domain, whereby the at least one disease is reduced or its progression is prevented in the subject.

2. The method of claim 1, wherein the soluble ENPP1 polypeptide comprises a somatomedin B domain, an ENPP1 catalytic domain, and an ENPP1 nuclease domain.

3. The method of claim 1, wherein the soluble ENPP1 polypeptide comprises residues 96-925 of human ENPP1 [NCBI#006199, SEQ ID NO: I].

4. The method of claim 1, wherein the soluble ENPP1 polypeptide is a secreted product of a precursor polypeptide expressed in a mammalian cell, wherein the precursor polypeptide comprises a signal sequence and ENPP1, wherein the precursor polypeptide undergoes proteolytic processing to the soluble ENPP1 polypeptide.

5. The method of claim 4, wherein the soluble ENPP1 polypeptide is a secreted product of a precursor polypeptide expressed in a mammalian cell, wherein the precursor polypeptide comprises an ENPP2 signal sequence, which is fused to the N-terminus of a polypeptide comprising a somatomedin B domain, an ENPP1 catalytic domain, and an ENPP1 nuclease domain, wherein the precursor polypeptide undergoes proteolytic processing to the soluble ENPP1 polypeptide.

6. The method of claim 5, wherein the soluble ENPP1 polypeptide is a secreted product of a precursor polypeptide expressed in a mammalian cell, wherein the precursor polypeptide comprises residues 1-76 of ENPP1 (SEQ ID NO: 1), residues 12-30 of NPP2 (NCBI accession no. NP_001124335, SEQ ID NO: 2), and residues 96-925 of ENPP1 (SEQ ID NO: 1), wherein the precursor polypeptide undergoes proteolytic processing to the soluble ENPP1 polypeptide.

7. The method of claim 1, wherein the soluble ENPP1 polypeptide is a secreted product of a precursor polypeptide expressed in a cell, wherein the precursor polypeptide lacks residues 77-98 of the ENPP1 transmembrane domain and comprises a signal sequence, wherein the precursor polypeptide undergoes proteolytic processing to the soluble ENPP1 polypeptide.

8. The method of claim 1, wherein the soluble ENPP1 polypeptide lacks a polyaspartic acid domain.

9. The method of claim 1, wherein the polypeptide is administered locally, regionally, parenterally, systemically, acutely or chronically to the subject.

10. The method of claim 1, wherein the subject is human.

11. The method of claim 1, wherein the polypeptide is administered in a dosage range from about 0.01 and 50 mg/kg of body weight.

12. The method of claim 1, wherein the polypeptide is administered in a dosage range from about 1 ng/kg and 500 mg/kg of body weight.

13. The method of claim 1, wherein the polypeptide is administered daily to the subject.

14. The method of claim 1, wherein the polypeptide is administered more than once per day to the subject.

15. The method of claim 1, wherein the polypeptide is administered every other day to the subject.

16. The method of claim 1, wherein the polypeptide is administered weekly or biweekly to the subject.

17. The method of claim 1, wherein the polypeptide is administered monthly to the subject.

18. The method of claim 1, wherein the polypeptide is administered to the subject as a pharmaceutical composition further comprising at least one excipient.

19. The method of claim 4, wherein the signal sequence comprises NPP5 signal sequence or NPP7 signal sequence.

20. The method of claim 1, wherein the polypeptide is administered to the subject as a pharmaceutical composition further comprising at least one pharmaceutically acceptable carrier.

21. The method of claim 1, wherein the soluble ENPP1 polypeptide is a fusion protein comprising a stability domain, wherein the stability domain is located at the C terminus of the ENPP1 polypeptide.

22. The method of claim 21, wherein the stability domain is selected from a group consisting of albumin and IgG Fc.

* * * * *